US008343509B2

(12) United States Patent
Stritzker et al.

(10) Patent No.: US 8,343,509 B2
(45) Date of Patent: Jan. 1, 2013

(54) METHODS AND COMPOSITIONS FOR DETECTION OF BACTERIA AND TREATMENT OF DISEASES AND DISORDERS

(75) Inventors: Jochen Harald Stritzker, Kissing (DE); Aladar A. Szalay, Highland, CA (US)

(73) Assignee: Genelux Corporation, San Diego, CA (US)

( * ) Notice: Subject to any disclaimer, the term of this patent is extended or adjusted under 35 U.S.C. 154(b) by 0 days.

(21) Appl. No.: 13/199,567

(22) Filed: Sep. 1, 2011

(65) Prior Publication Data
US 2012/0020883 A1 Jan. 26, 2012

Related U.S. Application Data

(62) Division of application No. 12/319,640, filed on Jan. 9, 2009.

(60) Provisional application No. 61/010,768, filed on Jan. 11, 2008.

(51) Int. Cl.
*A61K 39/108* (2006.01)
*A61K 39/02* (2006.01)
*C12Q 1/00* (2006.01)

(52) U.S. Cl. .... 424/241.1; 424/9.1; 424/9.2; 424/234.1; 424/4; 424/8; 424/29

(58) Field of Classification Search ................... 424/9.1, 424/9.2, 234.1, 241.1; 435/4, 8, 29
See application file for complete search history.

(56) References Cited

U.S. PATENT DOCUMENTS

| | | | | |
|---|---|---|---|---|
| 4,912,199 | A | 3/1990 | Lown et al. | 530/331 |
| 6,150,170 | A | 11/2000 | Powell et al. | 435/455 |
| 6,447,784 | B1 | 9/2002 | Bermudes et al. | 424/235.1 |
| 6,491,905 | B1 | 12/2002 | Sorscher et al. | 435/325 |
| 6,962,696 | B1 | 11/2005 | Bermudes et al. | 424/93.4 |
| 7,015,027 | B1 | 3/2006 | Redshaw | 435/252.3 |
| 7,247,296 | B2 | 7/2007 | Redshaw | 424/93.1 |
| 7,763,420 | B2 | 7/2010 | Stritzker et al. | 435/4 |
| 7,820,184 | B2 | 10/2010 | Stritzker et al. | 424/241.1 |
| 8,021,662 | B2 | 9/2011 | Szalay et al. | 424/138.1 |
| 8,052,968 | B2 | 11/2011 | Szalay et al. | 424/199.1 |
| 8,066,984 | B2 | 11/2011 | Szalay et al. | 424/93.21 |
| 8,137,904 | B2 | 3/2012 | Szalay et al. | 435/4 |
| 8,221,769 | B2 | 7/2012 | Szalay et al. | 424/232.1 |
| 2002/0054865 | A1 | 5/2002 | Fujimori et al. | 424/93.21 |
| 2003/0059400 | A1 | 3/2003 | Szalay | 424/93.2 |
| 2003/0161788 | A1 | 8/2003 | Zhao et al. | 424/9.6 |
| 2003/0228261 | A1 | 12/2003 | Szalay et al. | 424/93.34 |
| 2004/0213741 | A1 | 10/2004 | Szalay et al. | 424/9.6 |
| 2004/0234455 | A1 | 11/2004 | Szalay et al. | 424/9.6 |
| 2005/0025745 | A1 | 2/2005 | Fujimori | 424/93.2 |
| 2005/0031643 | A1 | 2/2005 | Szalay et al. | 424/199.1 |
| 2005/0069491 | A1 | 3/2005 | Yu et al. | 424/1.11 |
| 2005/0249670 | A1 | 11/2005 | Szalay et al. | 424/93.2 |
| 2005/0255088 | A1 | 11/2005 | Bermudes et al. | 424/93.2 |
| 2006/0051370 | A1 | 3/2006 | Szalay et al. | 424/199.1 |
| 2007/0025981 | A1 | 2/2007 | Szalay et al. | 424/130.1 |
| 2007/0202572 | A1 | 8/2007 | Szalay et al. | 435/69.1 |
| 2007/0212727 | A1 | 9/2007 | Szalay et al. | 435/6 |
| 2008/0193373 | A1 | 8/2008 | Stritzker et al. | 424/1.17 |
| 2009/0053244 | A1 | 2/2009 | Chen et al. | 424/174.1 |
| 2009/0081639 | A1 | 3/2009 | Hill et al. | 435/5 |
| 2009/0117047 | A1 | 5/2009 | Szalay et al. | 424/9.3 |
| 2009/0117048 | A1 | 5/2009 | Szalay et al. | 424/9.3 |
| 2009/0117049 | A1 | 5/2009 | Szalay et al. | 424/9.3 |
| 2009/0123382 | A1 | 5/2009 | Szalay et al. | 424/9.6 |
| 2009/0136917 | A1 | 5/2009 | Szalay et al. | 435/5 |
| 2009/0155287 | A1 | 6/2009 | Chen et al. | 424/158.1 |
| 2009/0162288 | A1 | 6/2009 | Chen et al. | 424/9.3 |
| 2009/0180955 | A1 | 7/2009 | Stritzker et al. | 424/1.73 |
| 2009/0180987 | A1 | 7/2009 | Stritzker et al. | 424/93.2 |
| 2010/0008946 | A1 | 1/2010 | Szalay et al. | 424/199.1 |
| 2010/0062016 | A1 | 3/2010 | Szalay et al. | 424/199.1 |
| 2010/0196325 | A1 | 8/2010 | Szalay et al. | 424/93.6 |
| 2010/0233078 | A1 | 9/2010 | Szalay et al. | 424/1.17 |
| 2011/0293527 | A1 | 12/2011 | Chen et al. | 424/9.3 |
| 2011/0300176 | A1 | 12/2011 | Szalay | 424/199.1 |
| 2012/0052003 | A9 | 3/2012 | Szalay | 424/1.11 |

FOREIGN PATENT DOCUMENTS

| | | |
|---|---|---|
| DE | 102 09 958 | 9/2003 |
| EP | 1 281 767 | 2/2003 |
| EP | 1 281 772 | 2/2003 |
| EP | 1 512 746 | 3/2005 |
| EP | 1 526 185 | 4/2005 |
| JP | 2002-97144 | 4/2002 |

(Continued)

OTHER PUBLICATIONS

Soghomonyan, S.A., et al., Cancer Gene Therapy, vol. 12, No. 1, pp. 101-108, 2005.*
Yu, Y.A., et al., Nature Biotechnology, vol. 22, No. 3, pp. 313-320, 2004.*
Abdui-Tahrani et al., "Ferritin mutants of *Escherichia coli* are iron deficient and growth impaired, and fur mutants and iron deficient," J. Bacteriol. 181(5):1415-1428 (1999).
Akita et al., "identification of oligopeptides binding to peritoneal tumors of gastric cancer," Cancer Sci. 97(10):1075-1081 (2006).
Altenbrunn et al., "Scintographic tumor localization in mice with radioiodinated anti-clostridium antibodies," Int. J. Nucl. Med. Biol. 8(1):90-93 (1981).

(Continued)

*Primary Examiner* — Rodney P. Swartz
(74) *Attorney, Agent, or Firm* — McKenna Long & Aldridge LLP; Stephanie Seidman

(57) ABSTRACT

Described herein are methods for detecting a bacteria in a subject and methods for detecting, imaging or diagnosing a site, disease, disorder or condition in a subject using bacteria. The methods can be used in conjunction with methods for treating a disease, disorder or condition. Such sites, diseases and disorders include sites of cellular proliferation, such as tumors, tumor tissues, metastases, areas of inflammation, immunoprivileged sites or tissues, wounds and infections. Further described are bacteria for use in the methods and compositions, combinations and kits, including diagnostic and pharmaceutical compositions, containing a bacterium. Bacteria described herein include those that bind, sequester or accumulate radiolabeled compounds by expression of an endogenous gene product that binds to the radiolabeled compound. Additional imaging and therapeutic agents and methods also are described.

10 Claims, No Drawings

FOREIGN PATENT DOCUMENTS

| WO | WO 84/00381 | 2/1984 |
|---|---|---|
| WO | WO 99/13053 | 3/1999 |
| WO | WO 01/14579 | 3/2001 |
| WO | WO 01/24637 | 4/2001 |
| WO | WO 01/25397 | 4/2001 |
| WO | WO 01/25399 | 4/2001 |
| WO | WO 03/045153 | 6/2003 |
| WO | WO 03/057007 | 7/2003 |
| WO | WO 03/063593 | 8/2003 |
| WO | WO 2004/030631 | 4/2004 |
| WO | WO 2008/073148 | 6/2008 |
| WO | WO 2008/099001 | 8/2008 |
| WO | WO 2009/126189 | 10/2009 |

OTHER PUBLICATIONS

Altenhoefer et al., "The probiotic *Escherichia coli* strain Nissle 1917 interferes with invasion of human intestinal epithelial cells by different enteroinvasive bacterial pathogens," FEMS Immunol. Med. Microbiol. 40(3):223-229 (2004).

Balbas and Bolivar, "Back to basics: pBR322 and protein expression systems in *E. coli*," P. Methods Mol. Biol. 267:77-90 (2004).

Bennett et al., "Positron emission tomography imaging for herpes virus infection: Implications for oncolytic viral treatments of cancer," Nat. Med 7(7):859-863 (2001).

Bereswill et al., "Regulation of Ferritin-Mediated Cytoplasmic Iron Storage by the Ferric Uptake Regulator Homolog (Fur) of *Helicobacter pylori*" J. Bacteriol. 182(21):5948-5953 (2000).

Bermudes et al., "Live bacteria as anticancer agents and tumor-selective protein delivery vectors," Curr. Opin. Drug Disc. 5(2):194-199 (2002).

Bettegowda et al., "Imaging bacterial infections with radiolabeled 1-(2'-deoxy-2'-fluoro-beta-D-arabinofuranosyl)-5-iodouracil," Proc. Natl. Acad. Sci. USA 102(4):1145-1150 (2005).

Bevis and Glick, "Rapidly maturing variants of the discosoma red fluorscent protein (DsRed)," Nat. Biotechnol. 20:83-87 (2002).

Blum et al., "intravenous iron supplementation for the treatment of the anemia of moderate to severe chronic renal failure patients not receiving dialysis," Infection 23(4):234-236 (1996).

Boudeau et al., "Inhibitory effect of probiotic *Escherichia coli* strain Nissle 1917 on adhesion to and invasion of intestinal epithelial cells by adherent-invasive *E. coli* strains isolated from patients with Crohn's disease," Aliment. Pharm. Therap. 18(1):45-56 (2003).

Brader et al., "*Escherichia coli* Nissle 1917 facilitates tumor detection by positron emission tomography and optical imaging," Clin. Cancer Res. 14(8):2295-2302 (2008).

Buursma et al., "I8F-FEAU as a radiotracer for herpes simplex virus thymidine kinase gene expression:in-vitro comparison with other PET tracers," Nucl. Med. Commun.27:25-30 (2006).

Certified English translation of DE 102 09 958 entitled "The use of *Escherichia coli* as antiphlogistic," published Sep. 25, 2003, Inventor: Hibi et al., (10 pages).

Cheadle and Jackson, "Bugs as drugs for cancer," Immunol. 107:10-19 (2002).

Chen and Morse, "*Neisseria gonorrhoeae* bacterioferritin: structural heterogeneity, involvement in iron storage and protection against oxidative stress," Microbiol. 145(Pt. 10):2967-2975 (1999).

Clairmont et al., "Enhanced antitumor activity from tumor-targeting *Salmonella* expressing endostatin," American Association for Cancer Research: 91st Annual Meeting of the AACR, Apr. 1-5, 2000, 41:732 Abstract 190 4653 (2000).

Collins and Wurst, "Suppression of SV40 tumors after immunization with group A *Streplococcus pyogenes* and *Bordetella pertussis*," Cancer Res. 34(5):932-937 (1974).

Condeelis and Segall, "Intravital imaging of cell movement in tumours," Nat. Rev. cancer 3:921-930 (2003).

de Boer et al., "The tac prometer: a functional hybrid derived from the trp and lac prometers," Proc. Natl. Acad. Sci. USA 80:21-25 (1983).

Dietrich et al., "Delivery of antigen-encoding plasmid DNA ino the cytosol of macrophages by attenuated suicide *Listeria monocytogenes*," Nat. Biotechnol. 16(2):181-185 (1998).

Ding et al., "Zinc-dependent dimers observed in crystals of human endostatin," Proc. Natl. Acad. Sci. USA 95:10443-10448 (1998).

Djeha et al., "Expression of *Escherichia coli* B nitroreductase in established human tumor xenografts in mice results in potent antitumoral and bystander effects upon systemic administration of the prodrug CB1954," Cancer Gene Ther. 7(5):721-731 (2000).

Farkas-Himsley et al., "The bacterial colicin active against tumor cells in vitro and in vivo is verotoxin 1," Proc. Natl. Acad. Sci. USA 92(15):6996-7000 (1995).

Forbes et al., "Sparse initial entrapment of systematically injected *Salmonella typhimurium* leads to heterogenous accumulation within tumors," Cancer Res. 63:5188-5193 (2003).

Forbes Lab Website, www.ecs.umass.edu/che/faculty/forbes.html, accessed on Feb. 6, 2006. [2 pages].

Fox et al., Erratum to "Anaerobic bacteria as a delivery system for cancer gene therapy: in vitro activiation of 5-fluorocytosine by genetically engineered clostridia," Gene Ther. 3(8):741 (1996).

Fox et al., "Anaerobic bacteria as a delivery system for cancer gene therapy: in vitro activation of 5-fluorocytosine by genetically engineered clostridia," Gene Ther. 3(2):173-178 (1996).

Francis et al., "Monitoring bioluminescent *Staphyloccus aureus* infections in living mice using a novel luxABCDE construct," Infect. Immun. 68(6):3594-3600 (2000).

Gambhir et al., "Imaging transgene expression with radionuclide imaging technologies," Neoplasia 2(1-2):118-138 (2000).

Grabherr and Bayer, "Impact of targeted vector design on Co/E1 plasmid replication," Trends Biotechnol. 20(6):257-260 (2002).

Grozdanov et al., "Analysis of the genome structure of the nonpathogenic probiotic *Escherichia coli* strian Nissle 1917," J. Bacteriol. 186(16):5432-5441 (2004).

Hockertz, S., "Immunomodulating effect of killed, apathogenic *Escherichia coli*, strain Nissle 1917, on the macrophage system," Arzneimittelforschung. 41(10):1108-1112 (1991). [article in German language with a English language abstract].

Jacobs et al., "Positron-emission tomography of vector-mediated gene expression in gene therapy for gliomas," Lancet 358:727-729 (2001).

Jadvar et al., "Molecular imaging update: Personalized imaging for improved diagnosis and treatment decisions," Highlights of Soc. Nuc. Med. 52nd Ann. Meeting (2005) (www.medscape.com/viewarticle/510976 accessed on Jul. 5, 2007). [5 pages].

Jain and Forbes, "Can engineered bacteria help control cancer?" Proc. Natl. Acad. Sci. USA 98(26):14748-14750 (2001).

Jung and Lee, "RNases in ColE1 DNA metabolism," Mol. Biol. Rep. 22(2-3):195-200 (1995-1996).

Kawamura et al., "Expression of *Escherichia coli* uracil phosphoribosyltransferase gene in murine colon carcinoma cells augements the antitumoral effect of 5-fluorouracil and induces protective immunity," Cancer Gene Ther. 7(4):637-643 (2000).

Khalil et al., "Mechanism of action tubulysin, an antimitotic peptide from myxobacteria," Chembiochem. 7(4):678-683 (2006).

Kimura et al., "Selective localization and growth of *Bifidobacterium bifidum* in mouse tumors, following intravenous administration," Cancer Res. 40(6):2061-2068 (1980).

Kok et al., "Biodistribution and imaging of FDG in rats with LS174T carcinoma xenografts and focal *Escherichia coli* infection," Cancer Biother. Radio. 20(3):310-315 (2005).

Kozak, M., "Structural features in Eukaryotic mRNAs that modulate the Initiation of Translation," J. Biol. Chem. 266:19867-19870 (1991).

Kruis W., "Review article: antibiotics and probiotics in inflammatory bowel disease," Pharmacol. Ther. 20 (Suppl 4):75-78 (2004).

Larson et al., "Triumph over mischance: a role for nuclear medicine in gene therapy," J. Nucl. Med. 38(8):1230-1233 (1997).

Lemmon et al., "Anaerobic bacteria as a gene delivery system that is controlled by the tumor microenvironment,"Gene Ther. 4:791-796 (1997).

Lemmon et al., "Anaerobic bacteria as a gene delivery system to tumors," Proceedings of the 85th Annual Meeting of the American Association for Cancer Research, San Francisco, CA Apr. 10-13, 1994, published in: Proc. Am. Cancer Research Assn 35:374 (1994).

Liegregts et al. "Effect of *E. Coli* Nissle 1917 on post-inflammatory visceral sensory function in a rat model," Neurogastroent. Motil. 17(3):410-414 (2005).

Liu et al., "Anticancer efficacy of systemically delivered anaerobic bacteria as gene therapy vectors targeting tumor hypoxia/necrosis," Gene Ther. 9(4):291-296 (2002).

Liu et al., "A highly efficient recombineering-based method for generating conditional knockout mutations," Genome Res. 13(3):476-484 (2003).

Liu et al., "Visualizing and quantifying protein secretion using a *Renilla luciferas*-GFP fusion protein," Luminescence 15(1):45-49 (2000).

Loessner et al., "Remote control of tumour-targeted *Salmonella enterica* serovar Typhimurium by the use of L-arabinose as inducer of bacterial gene expression in vivo," Cell. Microbiol. 9(6):1529-1537 (2007).

Love et al., "Radionuclide imaging of Infection," J. Nucl. Med. Technol. 32(2):47-57; quiz 58-59 (2004).

Macintyre and Cymet, "Probitoics: the benefits of bacterial cultures," Compr. Ther. 31(3):181-185 (2005).

Matz et al., "Fluorescent proteins from nonbioluminescent anthozoa species," Nat.Biotech. 17:969-973 (1999).

McDonald, D. and P. Choyke, "Imaging of angiogenesis: from microscope to clinic," Nat. Med. 9(6):713-725 (2003).

"*MUTAFLOR, The probiotic drug for life!*" http://www.ardeypharm.de/downlaod/php?id=10000, (downloaded on Apr. 16, 2008). [12 pages ].

Nagai et al., "A variant of yellow fluorescent protein with fast and efficient maturation for cell-biological applications," Nat. Biotechnol. 20(1):87-90 (2002).

NCBI Nucleotide AF188737 (Accessed on Apr. 30, 2008) (3 pages).
NCBI Nucleotide AJ586887 (Accessed on Apr. 30, 2008) (67 pages).
NCBI Nucleotide AJ586888 (Accessed on Apr. 30, 2008) (64 pages).
NCBI Nucleotide AJ586889 (Accessed on April 30, 2008) (28 pages).

Nguyen and Daugherty, "Evolutionary optimization of fluorescent proteins for intracellular FRET," Nat. Biotechnol. 23(3):355-360 (2005).

Parish, "Cancer immunotherapy: The past, the present and the future," Immunol. Cell Biol. 81:106-113 (2003).

Pawelek et al., "Bacteria as tumour-targeting vectors," Lancet Oncol. 4:548-556 (2003).

Pilcher, "GM Bug activates cancer drug: Bacteria targets medicine to shrivel mouse tumours," news @ nature.com, Published online: Apr. 22, 2004; http://www.nature.com/news/2004/040419/full/040419-9.html, (accessed on Nov. 18, 2004) (3 pages).

"Vion and Memorial Sloan-Kettering Cancer Center Present Data on Tapet's Potential to Enhance Imaging of Solid Tumors," Press Release, Vion Pharmaceuticals, Inc. (2000) (2 pages).

Rao et al., "Toward a live microbial microbicide for HIV: Commensal bacteria secreting an HIV fusion inhibitor peptide," Proc. Natl. Acad. Sci. 102(34):11993-11998 (2005).

Riedel et al., "Improved luciderase tagging system for listeria monocytogenes allows real-time monitoring in vivo and in vitro," Appl. Environ. Microbiol. 73:3091-3094 (2007).

Rizzo et al., "An improved cyan fluorescent protein variant useful for FRET," Nat. Biotechnol. 22(4):445-449 (2004).

Rothenberg et al., "Improving the evaluation of new cancer treatments: challenges and opportunities," Nat. Rev. Cancer 3:303-309 (2003).

Sartor, "Probiotic therapy of intestinal inflammation and infections," Curr. Opin. Gastroenterol. 21(1):44-50 (2005).

Schnetz, "Silencing of *Escherichia coli* bgl promoter by flanking sequence elements," EMBO J. 14(11):2545-2550 (1995).

Schoen et al., "Bacterial delivery of functional messenger RNA to mammalian cells," Cell Microbiol. 7(5):709-724 (2005).

Schultz et al., "Green fluorescent protein for detection of the probiotic microorganism *Escherichia coli* strain Nissle 1917 (EcN) in vivo," J. Microbiol. Methods 61(3):389-398 (2005).

Schultz et al., "Preventive effects of *Escherichia coli* strain Nissle 1917 on acute and chronic intestinal inflammation in two different murine models of colitis," Clin. Diag. Lab. Immunol. 11(2):372-378 (2004).

Serganova et al., "Molecular imaging of temporal dynamics and spatial heterogeneity of hypoxia-inducible factor -1 signal transduction activity in tumors in living mice," Cancer Res. 64:6101-6108 (2004).

Shaner et al., "A guide to choosing fluorescent proteins," Nat. Methods. 2(12):905-909 (2005).

Shkrob et al., "Far-red fluorescent proteins envolved from a blue chromoprotein from actinia euine," Biochem. J. 392(Pt 3):649-654 (2005).

Soghomonyan et al., "Positron emission tomography (PET) imaging of tumor-localized *Salmonella* expressing HSVI-TK" Cancer Gene Ther. 12(1):101-108 (2005).

Sorscher et al., "Tumor cell bystander killing in colonic carcinoma utilizing the *Escherichia coli* DeoD gene to generate toxic purines," Gene Ther. 1(4):233-238 (1994).

Springer et al., "Bacteria in cancer therapy" Microbiol. Today 56:113-115 (2005).

Stentebjerg-Olsen et al., "Type I fimbriation and phase switching in a natural *Escherichia coli* fimB Null strain, Nissle 1917," J. Bacteriol. 181(24):7470-7478 (1999).

Stritzker and Szalay, "*E. coli* Nissle 1917: Vom Kriegsveteran weiterentwickelt zum aktiven Kämpfer gegen Tumoren? [*E. coli* Nissle 1917: From War Veteran to Genetically-Directed Tumor Fighter" GenomXpress, 4.07, 12-14. (2007) Review.Full text [German].

Stritzker et al., "Tumor-specific colonization, tissue distribution, and gene induction by probiotic *Escherichia coli* Nissle 1917 in live mice," Int. J. Med. Microbiol. 297(3):151-162 (2007).

Sturm et al., "*Escherichia coli* Nissle 1917 distinctively modulates T-Cell cycling and expansion via toll-like receptor 2 signaling," Infect. Immun. 73(3):1452-1465 (2005).

Sun et al., "Genomic peculiarity of coding seuences and metabolic potential of probiotic *Escherichia coli* Nissle 1917 inferred from raw genome data," J. Biotech. 117:147-161 (2005).

Theys et al., "Specific targeting of cytosine deaminase to solid tumors by engineered *Clostridium acetobutylicum*," Cancer Gene Ther. 8(4):294-297 (2001).

Theys et al., "Tumor-specific gene delivery using genetically engineered bacteria," Curr. Gene Ther. 3(3):207-221 (2003).

Tjuvajev et al., "Imaging the Expression of Transfected Genes in Vivo," Cancer Res. 55(24):6126-6132 (1995).

Tjuvajev et al., "*Salmonella*-based tumor-targeted cancer therapy: tumor amplifies protein expression therapy (TAPET™) for diagnostic imaging," J. Control. Release 74:313-315 (2001).

Tjuvajev et al., "Comparison of radiolabeled nucleoside probes (FIAU, FHBG, and FHPG) for PET imaging of HSV1-tk gene expression," J. Nucl. Med. 43:1072-1083 (2002).

Toso et al., "Phase I study of the intravenous administration of attenuated *Salmonella typhimurium* to patients with metastatic melanoma," J. Clin. Oncol. 20(1):142-152 (2002).

Ukena et al., "The host response to the probiotic *Escherichia coli* strain Nissle 1917: specific up-regulation of the proinflammatory chemokine MCP-1," BMC Med. Genetics 6:43 (2005).

Waider et al., "Essential role of ferritin Pfr in *Helicobacter pylori* iron metabolism and gastric colonization" Infec. Immun. 70(7):3923-3929 (2002).

Wang et al., "Evolution of new nonantibody proteins via iterative somatic hypermutation," Proc. Natl. Acad. Sci. USA 101(48):16745-16749 (2004).

Watson et al., Molecular Biology of the Gene, 4th Edition, The Benjamin/Cummings Pub. co., p. 224. (1987).

Wehkamp et al., "NF-kappaB- and AP-1-mediated induction of human beta defensin-2 in intestinal epithelial cells by *Escherichia coli* Nissle 1917: a novel effect of a probiotic bacterium," Infect. Immun. 72:5750-5758 (2004).

Weissleder et al., "Molecular imaging," Radiol. 219:316-333 (2001).

Westendorf et al., "Intestinal immunity of *Escherichia coli* Nissle 1917: a safe carrier for therapeutic molecules" FEMS Immunol. Med. Microbiol. 43:373-384 (2005).

Westphal et al., "Containment of tumor-colonizing bacteria by host neutrophils," Cancer Res. 68(8):2952-2960 (2008).

Weibel et al., "Colonization of experimental murine breast tumors by *E. coli* K-12 significantly alters the tumor microenvironment," Cell. Microbiol. 10(6):1235-1248 (2008).

Wiedenmann et al., "A far-red fluorescent protein with fast maturation and reduced oligomerization tendency from *Entacmaea quadicolor* (Anthozoa, Actinaria)," Proc. Natl. Acad. Sci. USA 99(18):11646-11651 (2002).

Yazawa et al., "Current progress in suicide gene therapy for cancer," World J. Surg. 26(7):783-789 (2002).

Yu et al., "Establishment and characterization of conditions required for tumor colonization by intravenously delivered bacteria," Biotechnol.Bioeng. 100(3):567-578 (2008).

Yu et al., "Examinations of bacterium-mediated detection of tumors in mice models". In: Proceedings of teh 14th International Symposium on Bioluminescence & Chemiluminescence: Chemistry, Biology and Applcation. World Scientific: Singapore: 209-212 (2007).

Yu et al., "Optical imaging: bacteria, viruses and mammaliam cells encoding light-emitting proteins reveal the locations of primary tumors and metastases in animals," Anal. Bioanal. Chem. 377(6):964-972 (2003).

Yu et al., "Visualization of tumors and metastases in live animals with bacteria and vaccinia virus encoding light-emitting proteins," Nat. Biotech. 22(3):313-320 (2004).

Loessner et al., "Drug-inducible remote control of gene expression by probiotic *Escherichia coli* Nissle 1917 in intestine, tumor and gall bladder of mice," Microb. Infect. 11(14-15): 1097-1105 (2009).

Stritzker et al, "Enterobacterial tumor colonization in mice depends on bacterial metabolism and macrophages but is independent of chemotaxis and motility," Int. J. Med. Microbiol. 300 (7): 449-456 (2010).

Stritzker et al., "Myristoylation negative msbB-mutants of probiotic *E. coli* Nissle 1917 retain tumor specific colonization properties but show less side effects in immunocompetent mice," Bioengineered Bugs 1(2):139-145 (2010).

International Preliminary Report on Patentability, issued Jan. 29, 2009, in connection with International Patent Application Serial No. PCT/US2007/015829.

International Preliminary Report on Patentability, issued May 27, 2009, in connection with International Patent Application Serial No. PCT/US2007/015829.

International Search Report and the Written Opinion of the International Searching Authority, issued Sep. 17, 2009, in connection with International Patent Application Serial No. PCT/US2009/000148.

International Preliminary Report on Patentablility, issued Apr. 26, 2010, in connection with International Patent Application Serial No. PCT/US2009/000148.

Office Action, issued Oct. 5, 2011, in connection with corresponding U.S. Patent Application Serial No. 12/319,640, 8 pages.

Hill et al. "Magnetic Resonance Imaging of Tumors Colonized with Bacterial Ferritin-Expressing *Escherichia coli*," PloS One, 20116(10):e25409 (2011).

Office Action, issued Jun. 27, 2012, in connection with corresponding U.S. Appl. No. 12/319,640, 6 pages.

Yu et al., "Real-time imaging of tumors using replication-competent light emitting microorganisms," Methods Mol. Biol. 872: 159-175 (2012).

Appeal Brief Instructions, mailed on Nov. 8, 2011, in connection with related Japenses Patent Application No. 2006-0287210, 7 pages.

Response, mailed Feb. 6, 2012, in connection with related Japanese Patent Application No. 2006-287210, 6 pages.

Decision to Grant, issued Feb. 28, 2012, in connection with related Japanese Patent Application No. 2006-287210, 1 page.

Office Action, issued Dec. 20, 2011, in connection with related Japanese Patent Application No. 2009-136914, with detailed report of Office Action in English, 9 pages.

Office Action, issued Sep. 16, 2011, in connection with related Chinese Patent Application No. 200810130048.9, 16 pages.

Instructions for Response to Office Action dated Sep. 16, 2011, mailed Jan. 18, 2012, in connection with related Chinese Patent Application No. 200810130048.9, 8 pages.

Office Action, issued May 24, 2012, in connection with related Chinese Patent Application No. 200810130048.9, 7 pages.

Office Action, issued Jan. 23, 2012, issued in connection with related Canadian Patent Application 2,488,227, 2 pages.

Office Action, issued Apr. 28, 2012, in connection with related Chinese Patent Application No. 03812787.3, 7 pages.

Office Action, issued Mar. 19, 2009. in connection with related U.S. Appl. No. 11/875,518, 6 pages.

Notice of Allowanoc, issued Feb. 24, 2010, in cotenection with related U.S. Appl. No. 11/827,518, 10 pages.

Internationol Search Report, issued Jan. 13, 2009, in connection with related International Application No. PCT/US07/15829.

European Patent Office Communication pursuant to Rules 161(1) and 162 EPC, issued on Aug. 30, 2010, in connection with corresponding European Patent Application No. 09730017.2, 2 pages.

Response to European Patent Office Communication pursuant to Rules 161(1) and 162 EPC dated Aug. 30, 2010, mailed Oct. 11, 2010, in connection with corresponding European Patent Application No. 09730017.2, 9 pages.

\* cited by examiner

SEQUENCE LISTING

```
<160> NUMBER OF SEQ ID NOS: 2

<210> SEQ ID NO 1
<211> LENGTH: 12455
<212> TYPE: DNA
<213> ORGANISM: Artificial Sequence
<220> FEATURE:
<223> OTHER INFORMATION: pBR322\DEST PBAD-DUAL term

<400> SEQUENCE: 1
attatacata gttgataatt cactggatcg ataagcttta atgcggtagt ttatcacagt     60
taaattgcta acgcagtcag gcaccgtgta tgaaatctaa caatgcgctc atcgtcatcc    120
tcggcaccgt caccctggat gctgtaggca taggcttggt tatgccggta ctgccgggcc    180
tcttgcggga tatcgtccat tccgacagca tcgccagtca ctatggcgtg ctgctagcgc    240
tatatgcgtt gatgcaattt ctatgcgcac ccgttctcgg agcactgtcc gaccgctttg    300
gccgccgccc agtcctgctc gcttcgctac ttggagccac tatcgactac gcgatcatgg    360
cgaccacacc cgtcctgtgg atcctctacg ccggacgcat cgtggccggc atcaccggcg    420
ccacaggtgc ggttgctggc gcctatatcg ccgacatcac cgatggggaa gatcgggctc    480
gccacttcgg gctcatgagc gcttgtttcg gcgtgggtat ggtggcaggc cccgtggccg    540
ggggactgtt gggcgccatc tccttgcatg caccattcct gcggcggcg gtgctcaacg    600 gcctcaacct actactgggc tgcttcctaa tgcaggagtc gcataaggga gagcgtcgac    660
cgatgccctt gagagccttc aacccagtca gctccttccg gtgggcgcgg ggcatgacta    720
tcgtcgccgc acttatgact gtcttcttta tcatgcaact cgtaggacag gtgccggcag    780
cgctctgggt cattttcggc gaggaccgct ttcgctggag cgcgacgatg atcggcctgt    840
cgcttgcggt attcggaatc ttgcacgccc tcgctcaagc cttcgtcact ggtcccgcca    900
ccaaacgttt cggcgagaag caggccatta tcgccggcat ggcggccgac gcgctgggct    960
acgtcttgct ggcgttcgcg acgcgaggct ggatggcctt ccccattatg attcttctcg   1020
cttccggcgg catcgggatg cccgcgttgc aggccatgct gtccaggcag gtagatgacg   1080
accatcaggg acagcttcaa ggatcgctcg cggctcttac cagcctaact tcgatcactg   1140
gaccgctgat cgtcacggcg atttatgccg cctcggcgag cacatggaac gggttggcat   1200
ggattgtagg cgccgccta taccttgtct gcctccccgc gttgcgtcgc ggtgcatgga   1260
gccgggccac ctcgacctga atggaagccg gcggcacctc gctaacggat tcaccactcc   1320
aagaattgga gccaatcaat tcttgcggag aactgtgaat gcgcaaacca acccttggca   1380
gaacatatcc atcgcgtccg ccatctccag cagccgcacg cggcgcatct cgggcagcgt   1440
tgggtcctgg ccacgggtgc gcatgatcgt gctcctgtcg ttgaggaccc ggctaggctg   1500
gcggggttgc cttactggtt agcagaatga atcaccgata cgcgagcgaa cgtgaagcga   1560
ctgctgctgc aaaacgtctg cgacctgagc aacaacatga atggtcttcg gtttccgtgt   1620
```

```
ttcgtaaagt ctggaaacgc ggaagtcagc gccctgcacc attatgttcc ggatctgcat    1680
cgcaggatgc tgctggctac cctgtggaac acctacatct gtattaacga agcgctggca    1740
ttgaccctga gtgattttc tctggtcccg ccgcatccat accgccagtt gtttaccctc     1800
acaacgttcc agtaaccggg catgttcatc atcagtaacc cgtatcgtga gcatcctctc    1860
tcgtttcatc ggtatcatta cccccatgaa cagaaatccc ccttacacgg aggcatcagt    1920
gaccaaacag gaaaaaaccg cccttaacat ggcccgcttt atcagaagcc agacattaac    1980
gcttctggag aaactcaacg agctggacgc ggatgaacag gcagacatct gtgaatcgct    2040
tcacgaccac gctgatgagc tttaccgcag ctgcctcgcg cgtttcggtg atgacggtga    2100
aaacctctga cacatgcagc tcccggagac ggtcacagct tgtctgtaag cggatgccgg    2160
gagcagacaa gcccgtcagg gcgcgtcagc gggtgttggc gggtgtcggg gcgcagccat    2220
gacccagtca cgtagcgata gcggagtgta tactggctta actatgcggc atcagagcag    2280
attgtactga gagtgcacca tatgcggtgt gaaataccgc acagatgcgt aaggagaaaa    2340
taccgcatca ggcgctcttc cgcttcctcg ctcactgact cgctgcgctc ggtcgttcgg    2400
ctgcggcgag cggtatcagc tcactcaaag gcggtaatac ggttatccac agaatcaggg    2460
gataacgcag gaaagaacat gtgagcaaaa ggccagcaaa aggccaggaa ccgtaaaaag    2520
gccgcgttgc tggcgttttt ccataggctc cgcccccctg acgagcatca caaaaatcga    2580
cgctcaagtc agaggtggcg aaacccgaca ggactataaa gataccaggc gtttccccct    2640
ggaagctccc tcgtgcgctc tcctgttccg accctgccgc ttaccggata cctgtccgcc    2700
tttctccctt cgggaagcgt ggcgctttct catagctcac gctgtaggta tctcagttcg    2760
gtgtaggtcg ttcgctccaa gctgggctgt gtgcacgaac ccccgttca gcccgaccgc     2820 tgcgccttat ccggtaacta tcgtcttgag tccaacccgg taagacacga cttatcgcca    2880
ctggcagcag ccactggtaa caggattagc agagcgaggt atgtaggcgg tgctacagag    2940
ttcttgaagt ggtggcctaa ctacggctac actagaagga cagtatttgg tatctgcgct    3000
ctgctgaagc cagttacctt cggaaaaaga gttggtagct cttgatccgg caaacaaacc    3060
accgctggta gcggtggttt ttttgtttgc aagcagcaga ttacgcgcag aaaaaaagga    3120
tctcaagaag atcctttgat cttttctacg gggtctgacg ctcagtggaa cgaaaactca    3180
cgttaaggga ttttggtcat gagattatca aaaaggatct tcacctagat ccttttaaat    3240
taaaaatgaa gttttaaatc aatctaaagt atatatgagt aaacttggtc tgacagttac    3300
caatgcttaa tcagtgaggc acctatctca gcgatctgtc tatttcgttc atccatagtt    3360
gcctgactcc ccgtcgtgta gataactacg atacgggagg gcttaccatc tggccccagt    3420
gctgcaatga taccgcgaga cccacgctca ccggctccag atttatcagc aataaaccag    3480
ccagccggaa gggccgagcg cagaagtggt cctgcaactt tatccgcctc catccagtct    3540
attaattgtt gccgggaagc tagagtaagt agttcgccag ttaatagttt gcgcaacgtt    3600
gttgccattg ctgcaggcat cgtggtgtca cgctcgtcgt ttggtatggc ttcattcagc    3660
tccggttccc aacgatcaag gcgagttaca tgatccccca tgttgtgcaa aaaagcggtt    3720
agctccttcg gtcctccgat cgttgtcaga agtaagttgg ccgcagtgtt atcactcatg    3780
gttatggcag cactgcataa ttctcttact gtcatgccat ccgtaagatg cttttctgtg    3840
actggtgagt actcaaccaa gtcattctga gaatagtgta tgcggcgacc gagttgctct    3900
tgcccggcgt caacacggga taataccgcg ccacatagca gaactttaaa agtgctcatc    3960
attggaaaac gttcttcggg gcgaaaactc tcaaggatct taccgctgtt gagatccagt    4020
```

```
tcgatgtaac ccactcgtgc acccaactga tcttcagcat cttttacttt caccagcgtt    4080
tctgggtgag caaaaacagg aaggcaaaat gccgcaaaaa agggaataag ggcgacacgg    4140
aaatgttgaa tactcatact cttccttttt caatattatt gaagcattta tcagggttat    4200
tgtctcatga gcggatacat atttgaatgt atttagaaaa ataaacaaat aggggttccg    4260
cgcacatttc cccgaaaagt gccacctgac gtctaagaaa ccattattat catgacatta    4320
acctataaaa ataggcgtat cacgaggccc tttcgtcttc aagaattctc atgtttgaca    4380
gcttatcatc gataccatga ttacgccaag ctatcaactt tgtatagaaa agttgttatg    4440
acaacttgac ggctacatca ttcacttttt cttcacaacc ggcacggaac tcgctcgggc    4500
tggccccggt gcattttta aatacccgcg agaatagag ttgatcgtca aaaccaacat    4560
tgcgaccgac ggtggcgata ggcatccggg tggtgctcaa aagcagcttc gcctggctga    4620
tacgttggtc ctcgcgccag cttaagacgc taatccctaa ctgctggcgg aaaagatgtg    4680
acagacgcga cggcgacaag caaacatgct gtgcgacgct ggcgatatca aaattgctgt    4740
ctgccaggtg atcgctgatg tactgacaag cctcgcgtac ccgattatcc atcggtggat    4800
ggagcgactc gttaatcgct tccatgcgcc gcagtaacaa ttgctcaagc agatttatcg    4860
ccagcagctc cgaatagcgc ccttccct gcccggcgtt aatgatttgc ccaaacaggt    4920
cgctgaaatg cggctggtgc gcttcatccg gcgaaagaa ccccgtattg gcaaatattg    4980
acggccagtt aagccattca tgccagtagg cgcgcggacg aaagtaaacc cactggtgat    5040
accattcgcg agcctccgga tgacgaccgt agtgatgaat ctctcctggc gggaacagca    5100
aaatatcacc cggtcggcaa acaaattctc gtccctgatt tttcaccacc ccctgaccgc    5160
gaatggtgag attgagaata taccttttca ttcccagcgg tcggtcgata aaaaaatcga    5220
gataaccgtt ggcctcaatc ggcgttaaac ccgccaccag atgggcatta acgagtatc    5280 ccggcagcag gggatcattt tgcgcttcag ccatactttt catactcccg ccattcagag    5340
aagaaaccaa ttgtccatat tgcatcagac attgccgtca ctgcgtcttt tactggctct    5400
tctcgctaac caaaccggta accccgctta ttaaaagcat tctgtaacaa gcgggacca    5460 aagccatgac aaaaacgcgt aacaaaagtg tctataatca cggcagaaaa gtccacattg    5520
attatttgca cggcgtcaca cttttgctatg ccatagcatt tttatccata agattagcgg    5580
atcctacctg acgctttta tcgcaactct ctactgtttc tccatacccg tttttttggg    5640
ctagcaagtt tgtacaaaaa agcaggctag gaggaataaa aaatgagtaa aggcgaagaa    5700
cttttcactg gagttgtccc aattcttgtt gaattagatg gtgatgttaa tgggcacaaa    5760
ttttctgtca gtggagaggg tgaaggtgat gcaacatacg gaaaacttac ccttaaattt    5820
atttgcacta ctggaaaact acctgttcca tggccaacac ttgtcactac tttcggttat    5880
ggtgttcaat gctttgcgag atacccagat catatgaaac agcatgactt tttcaagagt    5940
gccatgcccg aaggttatgt acaggaaaga actatatttt tcaaagatga cgggaactac    6000
aagacacgtg ctgaagtcaa gtttgaaggt gatacccttg ttaatagaat cgagttaaaa    6060
ggtattgatt ttaaagaaga tggaaacatt cttggacaca attggaata caactataac    6120 tcacacaatg tatacatcat ggcagacaaa caaaagaatg gaatcaaagt aacttcaaa    6180 attagacaca acattgaaga tggaagcgtt caactagcag accattatca acaaaatact    6240
ccaattggcg atggccctgt ccttttacca gacaaccatt acctgtccgc acaatctgcc    6300
ctttcgaaag atcccaacga aaagagagac cacatggtcc ttcttgagtt tgtaacagct    6360
gctgggatta cacatggcat ggatgaacta tacaaataaa tgtgtcgaca ggaggactct    6420
```

```
ctatgaaatt tggaaacttt ttgcttacat accaacctcc ccaatttct caaacagagg    6480 taatgaaacg tttggttaaa ttaggtcgca tctctgagga gtgtggtttt gataccgtat    6540
ggttactgga gcatcatttc acggagtttg gtttgcttgg taaccccttat gtcgctgctg    6600 catatttact tggcgcgact aaaaaattga atgtaggaac tgccgctatt gttcttccca    6660
cagcccatcc agtacgccaa cttgaagatg tgaatttatt ggatcaaatg tcaaaaggac    6720
gatttcggtt tggtatttgc cgagggcttt acaacaagga ctttcgcgta ttcggcacag    6780
atatgaataa cagtcgcgcc ttagcggaat gctggtacgg gctgataaag aatggcgtga    6840
cagagggata tatggaagct gataatgaac atatcaagtt ccataaggta aaagtaaacc    6900
ccgcggcgta tagcagaggt ggcgcaccgg tttatgtggt ggctgaatca gcttcgacga    6960
ctgagtgggc tgctcaattt ggcctaccga tgatattaag ttggattata aatactaacg    7020
aaaagaaagc acaacttgag ctttataatg aagtggctca agaatatggg cacgatattc    7080
ataatatcga ccattgctta tcatatataa catctgtaga tcatgactca attaaagcga    7140
aagagatttg ccggaaattt ctggggcatt ggtatgattc ttatgtgaat gctacgacta    7200
tttttgatga ttcagaccaa acaagaggtt atgatttcaa taaagggcag tggcgtgact    7260
ttgtattaaa aggacataaa gatactaatc gccgtattga ttacagttac gaaatcaatc    7320
ccgtgggaac gccgcaggaa tgtattgaca taattcaaaa agacattgat gctacaggaa    7380
tatcaaatat ttgttgtgga tttgaagcta atggaacagt agacgaaatt attgcttcca    7440
tgaagctctt ccagtctgat gtcatgccat ttcttaaaga aaaacaacgt tcgctattat    7500
attagctaag gagaaagaaa tgaaatttgg attgttcttc cttaacttca tcaattcaac    7560
aactgttcaa gaacaaagta tagttcgcat gcaggaaata acggagtatg ttgataagtt    7620
gaattttgaa cagattttag tgtatgaaaa tcattttca gataatggtg ttgtcggcgc    7680
tcctctgact gtttctggtt ttctgctcgg tttaacagag aaaattaaaa ttggttcatt    7740
aaatcacatc attacaactc atcatcctgt ccgcatagcg gaggaagctt gcttattgga    7800
tcagttaagt gaagggagat ttattttagg gtttagtgat tgcgaaaaaa aagatgaaat    7860
gcattttttt aatcgcccgg ttgaatatca acagcaacta tttgaagagt gttatgaaat    7920
cattaacgat gctttaacaa caggctattg taatccagat aacgatttt atagcttccc    7980 taaaatatct gtaaatcccc atgcttatac gccaggcgga cctcggaaat atgtaacagc    8040
aaccagtcat catattgttg agtgggcggc caaaaaaggt attcctctca tctttaagtg    8100
ggatgattct aatgatgtta gatatgaata tgctgaaaga tataaagccg ctgcggataa    8160
atatgacgtt gacctatcag agatagacca tcagttaatg atattagtta actataacga    8220
agatagtaat aaagctaaac aagagacgcg tgcatttatt agtgattatg ttcttgaaat    8280
gcaccctaat gaaaatttcg aaaataaact tgaagaaata attgcagaaa acgctgtcgg    8340
aaattatacg gagtgtataa ctgcggctaa gttggcaatt gaaaagtgtg gtgcgaaaag    8400
tgtattgctg tcctttgaac caatgaatga tttgatgagc caaaaaaatg taatcaatat    8460
tgttgatgat aatattaaga agtaccacat gaaatatacc taataggtac ccggggatcc    8520
taataggtac caggaggaag gcaaatgtga ctaaaaaaat ttcattcatt attaacggcc    8580
aggttgagat ctttcccgaa ggtgatgatt tagtgcaatc cattaatttt ggtgataata    8640
gtgtttacct gccaatattg aatgactctc atgtaaaaaa cattattgat tgtaatggaa    8700
ataacgaatt acggttgcat aacattgtca atttctcta tacggtaggg caaagatgga    8760
aaaatgaaga atactcaaga cgcaggacat acattcgtga cttaaaaaaa tatatgggat    8820
```

| | |
|---|---|
| attcagaaga aatggctaag ctagaggcca attggatatc tatgatttta tgttctaaag | 8880 |
| gcggccttta tgatgttgta gaaaatgaac ttggttctcg ccatatcatg gatgaatggc | 8940 |
| tacctcagga tgaaagttat gttcgggctt ttccgaaagg taaatctgta catctgttgg | 9000 |
| caggtaatgt tccattatct gggatcatgt ctatattacg cgcaatttta actaagaatc | 9060 |
| agtgcattat aaaaacatcg tcaaccgatc cttttaccgc taatgcatta gcgttaagtt | 9120 |
| ttattgatgt agaccctaat catccgataa cgcgctcttt atctgttata tattggcccc | 9180 |
| accaaggtga tacatcactc gcaaaagaaa ttatgcaaca tgcggatgtt attgtcgctt | 9240 |
| ggggagggcc agatgcgatt aattgggcgg tagagcatgc gccatcttat gctgatgtga | 9300 |
| ttaaatttgg ttctaaaaag agtctttgca ttatcgataa tcctgttgat ttgacgtccg | 9360 |
| cagcgacagg tgcggctcat gatgtttgtt tttacgatca gcgagcttgt ttttctgccc | 9420 |
| aaaacatata ttcatggga aatcattatg aggaatttaa gttagcgttg atagaaaaac | 9480 |
| ttaatctata tgcgcatata ttaccgaatg ccaaaaaaga ttttgatgaa aaggcggcct | 9540 |
| attctttagt tcaaaaagaa agcttgtttg ctggattaaa agtagaggtg atattcatc | 9600 |
| aacgttggat gattattgag tcaaatgcag gtgtggaatt taatcaacca cttggcagat | 9660 |
| gtgtgtacct tcatcacgtc gataatattg agcaaatatt gccttatgtt caaaaaaata | 9720 |
| agacgcaaac catatctatt tttccttggg agtcatcatt taaatatcga gatgcgttag | 9780 |
| cattaaaagg tgcggaaagg attgtagaag caggaatgaa taacatattt cgagttggtg | 9840 |
| gatctcatga cggaacgaga ccgttgcaac gattagtgac atatatttct catgaaaggc | 9900 |
| catctaacta tacggctaag gatgttgcgg ttgaaataga acagactcga ttcctggaag | 9960 |
| aagataagtt ccttgtatt gtcccataat aggtaaaagt atgctagctt gtattttac | 10020 |
| caaggaggaa taaaaatgg aaaatgaatc aaaatataaa accatcgacc acgttatttg | 10080 |
| tgttgaagga ataagaaaa ttcatgtttg ggaaacgctg ccagaagaaa acagcccaaa | 10140 |
| gagaaagaat gccattatta ttgcgtctgg ttttgcccgc aggatggatc attttgctgg | 10200 |
| tctggcggaa tatttatcgc ggaatggatt tcatgtgatc cgctatgatt cgcttcacca | 10260 |
| cgttggattg agttcaggga caattgatga atttacaatg tctataggaa agcagagctt | 10320 |
| gttagcagtg gttgattggt taactacacg aaaaataaat aacttcggta tgttggcttc | 10380 |
| aagcttatct gcgcggatag cttatgcaag cctatctgaa atcaatgctt cgttttaat | 10440 |
| caccgcagtc ggtgttgtta acttaagata ttctcttgaa agagctttag ggtttgatta | 10500 |
| tctcagtcta cccattaatg aattgccgaa taatctagat tttgaaggcc ataaattggg | 10560 |
| tgctgaagtc tttgcgagag attgtcttga ttttggttgg gaagatttag cttctacaat | 10620 |
| taataacatg atgtatcttg atataccgtt tattgctttt actgcaaata cgataattg | 10680 |
| ggtcaagcaa gatgaagtta tcacattgtt atcaaatatt cgtagtaatc gatgcaagat | 10740 |
| atattctttg ttaggaagtt cgcatgactt gagtgaaaat ttagtggtcc tgcgcaattt | 10800 |
| ttatcaatcg gttacgaaag ccgctatcgc gatggataat gatcatctgg atattgatgt | 10860 |
| tgatattact gaaccgtcat ttgaacattt aactattgcg acagtcaatg aacgccgaat | 10920 |
| gagaattgag attgaaaatc aagcaatttc tctgtcttaa aggatcctga ggaggaaaac | 10980 |
| aggtatgact tcatatgttg ataaacaaga aattacagca agctcagaaa ttgatgattt | 11040 |
| gatttttttcg agcgatccat tagtgtggtc ttacgacgag caggaaaaaa tcagaaagaa | 11100 |
| acttgtgctt gatgcatttc gtaatcatta taaacattgt cgagaatatc gtcactactg | 11160 |
| tcaggcacac aaagtagatg acaatattac ggaaattgat gacataccctg tattcccaac | 11220 |

```
atcggttttt aagtttactc gcttattaac ttctcaggaa aacgagattg aaagttggtt    11280
taccagtagc ggcacgaatg gtttaaaaag tcaggtggcg cgtgacagat taagtattga    11340
gagactctta ggctctgtga gttatggcat gaaatatgtt ggtagttggt ttgatcatca    11400
aatagaatta gtcaatttgg gaccagatag atttaatgct cataatattt ggtttaaata    11460
tgttatgagt ttggtggaat tgttatatcc tacgacattt accgtaacag aagaacgaat    11520
agattttgtt aaaacattga atagtcttga acgaataaaa aatcaaggga aagatctttg    11580
tcttattggt tcgccatact ttatttattt actctgccat tatatgaaag ataaaaaaat    11640
ctcattttct ggagataaaa gcctttatat cataaccgga ggcggctgga aaagttacga    11700
aaaagaatct ctgaaacgtg atgatttcaa tcatctttta tttgatactt tcaatctcag    11760
tgatattagt cagatccgag atatatttaa tcaagctgaa ctcaacactt gtttctttga    11820
ggatgaaatg cagcgtaaac atgttccgcc gtgggtatat gcgcgagcgc ttgatcctga    11880
aacgttgaaa cctgtacctg atggaacgcc ggggttgatg agttatatgg atgcgtcagc    11940
aaccagttat ccagcattta ttgttaccca tgatgtcggg ataattagca gagaatatgg    12000
taagtatccc ggcgtgctcg ttgaaatttt acgtcgcgtc aatacgagga cgcagaaagg    12060
gtgtgcttta agcttaaccg aagcgtttga tagttgaacc cagctttctt gtacaaagtg    12120
gaaatcagaa cgcagaagcg gtctgataaa acagaatttg cctggcggca gtagcgcggt    12180
ggtcccacct gaccccatgc cgaactcaga agtgaaacgc cgtagcgccg atggtagtgt    12240
ggggtctccc catgcgagag tagggaactg ccaggcatca aataaaacga aaggctcagt    12300
cgaaagactg ggcctttcgt tttatctgtt gtttgtcggt gaacgctctc ctgagtagga    12360
caaatccgcc gggagcggat ttgaacgttg cgaagcaacg gcccggaggg tggcgggcag    12420
gacgcccgcc ataaactgcc agtttaaaca acttt                              12455

<210> SEQ ID NO 2
<211> LENGTH: 19
<212> TYPE: DNA
<213> ORGANISM: Artificial Sequence
<220> FEATURE:
<223> OTHER INFORMATION: fur consensus sequence

<400> SEQUENCE: 2
gataatgata atcattatc                                                  19
```

METHODS AND COMPOSITIONS FOR DETECTION OF BACTERIA AND TREATMENT OF DISEASES AND DISORDERS

RELATED APPLICATIONS

This application is a divisional of U.S. application Ser. No. 12/319,640, to Jochen H. Stritzker and Aladar A. Szalay, filed on Jan. 9, 2009, entitled "Methods and Compositions for Detection of Bacteria and Treatment of Diseases and Disorders," which claims the benefit of priority under 35 U.S.C. §119(e) to U.S. Provisional Application Ser. No. 61/010,768, to Jochen H. Stritzker and Aladar A. Szalay, filed on Jan. 11, 2008, entitled "Methods and Compositions for Detection of Bacteria and Treatment of Diseases and Disorders." This application is related to International Application No. PCT/US2009/00148 to Jochen H. Stritzker and Aladar A. Szalay, filed on Jan. 9, 2009, entitled "Methods and Compositions for Detection of Bacteria and Treatment of Diseases and Disorders," which also claims priority to U.S. Provisional Application Ser. No. 61/010,768. The subject matter of each of these applications is incorporated by reference in its entirety.

This application is related to U.S. application Ser. No. 11/827,518, now U.S. Pat. No. 7,763,420, filed on Jul. 11, 2007, entitled "Methods and Composition for Detection of Microorganisms and Cells and Treatment of Diseases and Disorders," and to International Application No. PCT/US2007/015829, filed on Jul. 11, 2007, entitled "Methods and Composition for Detection of Microorganisms and Cells and Treatment of Diseases and Disorders."

This application also is related to U.S. application Ser. No. 10/872,156, now U.S. Pat. No. 7,588,767, to Aladar A. Szalay, Tatyana Timiryasova, Yong A. Yu and Qian Zhang, filed on Jun. 18, 2004, entitled "Microorganisms for Therapy," and to International PCT Application Serial No. PCT/USO4/19866, filed on Jun. 18, 2004, entitled "Microorganisms for Therapy."

This application also is related to U.S. application Ser. No. 10/866,606, filed Jun. 10, 2004, entitled "Light emitting microorganisms and cells for diagnosis and therapy of tumors," which is a continuation of U.S. application Ser. No. 10/189,918, filed Jul. 3, 2002, entitled "Light emitting microorganisms and cells for diagnosis and therapy of tumors." This application also is related to International PCT Application PCT/IB02/04767, filed Jul. 31, 2002, entitled "Microorganisms and Cells for Diagnosis and Therapy of Tumors," EP Application No. 01 118 417.3, filed Jul. 31, 2002entitled "Light-emitting microorganisms and cells for tumor diagnosis/therapy," EP Application No. 01 125 911.6, filed Oct. 30, 2001, entitled "Light-emitting microorganism and cells for diagnosis and therapy of tumors"and EP Application No. 02 0794 632.6, filed Jul. 31, 2002, entitled "Vaccinia Virus for Diagnosis and Therapy of Tumors."

This application also is related to U.S. application Ser. No. 10/849,664, filed May 19, 2004, entitled "Light Emitting Microorganisms and Cells for Diagnosis and Therapy of Diseases Associated with Wounded or Inflamed Tissue," which is a continuation of U.S. application Ser. No. 10/163,763, filed Jun. 5, 2002, entitled, "Light Emitting Microorganisms and Cells for Diagnosis and Therapy of Diseases Associated with Wounded or Inflamed Tissue;" International PCT Application PCT/EP03/05907, filed Jun. 5, 2003, entitled, "Light Emitting Microorganisms and Cells for Diagnosis and Therapy of Diseases Associated with Wounded or Inflamed Tissue;" and EP Application No. 02 012 552.2, filed Jun. 5, 2002, entitled "Light Emitting Microorganisms and Cells for Diagnosis and Therapy of Diseases Associated with Wounded or Inflamed Tissue."

The subject matter of each of the above applications, publications and international applications is incorporated by reference in its entirety.

FIELD OF THE INVENTION

Methods of detecting bacteria in a subject and treating diseases and disorders are provided herein. Methods of detecting or diagnosing sites of cellular proliferation associated with diseases, disorders and conditions, such as neoplasms, tumors, neoplastic diseases, cancers, wounds and inflammation, are also provided. Further provided are compositions, combinations and kits containing the bacteria for use in the methods and use in the preparation of diagnostic and therapeutic or pharmaceutical compositions.

BACKGROUND

Targeting of bacteria to solid tumors has been demonstrated for several bacterial species including *Bifidobacterium* spp. (Kimura et al. (1980) *Cancer Res.* 40:2061-8), *Listeria monocytogenes* (Liu et al. (2007) *Cancer Res.* 67:429-32; Riedel et al. (2007) *Appl Environ Microbiol.* 73:3091-4), *Clostridium* spp. Bettegowda et al. (2005) *Proc. Natl. Acad. Sci. U.S.A.* 102:1145-50), *Salmonella* spp. (Toso et al. (2002) *J. Clin. Oncol.* 20:142-52), *Shigella flexneri* (Stritzker et al. (2007) *Int. J. Med Microbiol.* 297:51-62) *Vibrio cholerae* (Yu et al. (2004) *Nat. Biotechnol.* 22:313-20) and *E. coli* (Stritzker et al. (2007) *Int. J. Med. Microbiol.* 297:51-62). The use of certain bacteria for therapy and diagnosis of tumors, however, is often impeded by risks of opportunistic infections and low tumor colonization rates. For example, in clinical trials of *Salmonella* VNP20009, a low percentage of tumor-targeting efficacy was observed (Toso et al. (2002) *J. Clin. Oncol.* 20:142-52). Thus, for bacterial therapy and diagnosis of tumors, there is a need for methods that employ bacteria that are non-toxic to the patient, can be administered at low doses and show a high degree of preferential accumulation in tumors versus normal tissues.

In addition, biopsy is currently the only clinical method available for determining the presence of bacteria in the tumor. A majority of studies on bacterial tumor colonization in tumor-bearing mice have used luciferase- and/or fluorescence-(GFP) imaging for bacterial detection. However, current optical imaging modalities using fluorescent proteins or luciferases are restricted to small animals and cannot be readily translated to patient studies. Hence, there is a need for methods for non-invasive imaging of bacteria-colonized tumors to accurately detect the presence of bacteria in tumors without excision of the respective tissue.

Overexpression of HSV-thymidine kinase in tumors has been used to localize radiolabeled tracers to tumors for tumor imaging by positron emission tomography (PET) (Serganova et al. (2004) *Cancer Res.* 64:6101-8; Tjuvajev et al. (1998) *Cancer Res.* 58:4333-41; Tjuvajev et al. (2002) *J. Nucl. Med.* 43:1072-83; Jacobs et al. (2001) *Lancet* 358:727-9). *Salmonella* bacteria that overexpress HSV-thymidine kinase, *Salmonella* VNP20009, have been employed to image C-38 colon carcinoma and B16-F10 murine melanoma by PET using the radiolabeled tracer [$^{124}$I]-FIAU (Soghomonyan et al. (2005) *Cancer Gene Ther.* 12:101-8). However, gene expression systems that are designed to overexpress proteins can be highly variable, leading to varying amounts of gene expression at the site of accumulation. Such systems are not quantitative and cannot be used to accurately measure the accumulation of the administered bacteria within a tumor over the course of treatment, diagnosis or monitoring of a tumor. Hence, there is a need for methods to accurately measure the amount of bacterial accumulation in a tumor in order to use the bacteria for diagnostic methods, such as monitoring therapeutic treatment and/or optimizing therapeutic regimens and with decreased reliance on foreign protein expression.

SUMMARY

Provided herein are methods of detecting and/or imaging a site of proliferation using a non-pathogenic bacterium that expresses an endogenous thymidine kinase and radiolabeled compound that binds to the thymidine kinase. An exemplary bacterium for use in the methods is the *Escherichia coli* Nissle bacterium. In particular example, the bacterium is *Escherichia coli* Nissle strain 1917. The site of proliferation can be, for example, a tumor, tumor tissue, wound, wound tissue, site of inflammation and inflamed tissue. An exemplary radiolabeled compound is a nucleoside analog. In a particular example, the site of proliferation contains cancerous tissue. The cancerous tissue can be, for example, a tumor or a metastasis. Exemplary cancers to be treated include, but are not limited to, pancreatic cancer, lung cancer, ovarian cancer, breast cancer, cervical cancer, bladder cancer, prostate cancer, glioma cancer, adenocarcinoma, liver cancer, skin cancer or a combination thereof.

Provided herein are methods of detecting and/or imaging a site of proliferation by administering a non-pathogenic bacterium that localizes to the site of proliferation and detecting the accumulation of a radiolabeled compound in the localized bacterium. The radiolabeled can be detected and/or imaged externally to the subject. In an exemplary method, the bacteria express an endogenous thymidine kinase and the radiolabeled compound binds to the thymidine kinase. In some examples the thymidine kinase phosphorylates the radiolabeled compound. In some examples, the radioisotope of the radiolabeled compound directly or indirectly emits gamma radiation. Exemplary radioisotopes include $^{123}$I, $^{124}$I, $^{125}$I, $^{131}$I, $^{18}$F, $^{19}$F, $^{11}$C, $^{13}$C, $^{14}$C, $^{75}$Br, $^{76}$Br and $^{3}$H.

The radiolabeled compounds can be detected and/or imaged by methods such as, but not limited to, positron emission tomography, planar gamma imaging or single photon emission computed tomography. Exemplary radiolabeled compounds include nucleoside analogs, such as, but not limited to, radioloabeled forms of 1-(2'deoxy-2'-fluoro-β-D-arabinofuranosyl)-5-iodouracil (FIAU), 1-(2'deoxy-2'-fluoro-β-D-arabinofuranosyl)-5-ethyluracil (FEAU), 1-(2'-deoxy-2'-fluoro-β-D-arabinofuranosyl)-5-methyluracil (FMAU), 3'-deoxy-3'-fluorothymidine (FLT), 9-[4'-fluoro-3'-(hydroxymethyl)butyl]guanine (FHBG) and 9-[(3'-fluoro-1'-hydroxy-2'-propoxy)methyl]guanine (FHPG). Exemplary radiolabeled nucleoside analogs include, but are not limited to, [$^{125}$I]-1-(2'deoxy-2'-fluoro-β-D-arabinofuranosyl)-5-iodouracil ([$^{125}$I]-FIAU), [$^{124}$I]-1-(2'deoxy-2'-fluoro-β-D-arabinofuranosyl)-5-iodouracil ([$^{124}$I]-FIAU), [$^{18}$F]-1-(2'deoxy-2'-fluoro-β-D-arabinofuranosyl)-5-iodouracil ([$^{18}$F]-FIAU), [$^{18}$F]-1-(2'deoxy-2'-fluoro-β-D-arabinofuranosyl)-5-ethyluracil ([$^{18}$F]-FEAU), [$^{18}$F]-1-(2'-deoxy-2'-fluoro-β-D-arabinofuranosyl)-5-methyluracil ([$^{18}$F]-FMAU), [$^{18}$F]-3'-deoxy-3'-fluorothymidine ([$^{18}$F]-FLT), [$^{18}$F]-9-[4'-fluoro-3'-(hydroxymethyl)butyl]guanine ([$^{18}$F]-FHBG) and [$^{18}$F]-9-[(3'-fluoro-1'-hydroxy-2'-propoxy)methyl]guanine ([$^{18}$F]-FHPG).

In an exemplary method, the bacteria used in the methods provided herein can be administered systemically, such as intravenously or intraperitoneally. In an exemplary method, the radiolabeled compound used in the methods provided herein is administered systemically or orally. The bacteria and the radiolabeled compound can be administered sequentially, simultaneously or intermittently.

Provided herein are methods of detecting and/or imaging a site of proliferation using two or more detection methods. In one example, a site of proliferation, such as a tumor, is detected and/or imaged by administering a non-pathogenic bacterium that localizes to the site of proliferation and detecting/imaging the accumulation of a radiolabeled compound in the localized bacterium using a method such as positron emission tomography, planar gamma imaging, single photon emission computed tomography, where the site of proliferation, such as a tumor, also is detected and/or imaged by a second imaging method. The second imaging method, for example, can be selected from among magnetic resonance imaging, computed tomography (CT), magnetic resonance imaging (MRI), X-ray, fluorescence imaging or bioluminescence imaging. Where two or more imaging methods are employed, the imaging can be performed sequentially or simultaneously with the detection/imaging of the radiolabeled compound.

The bacteria for use in the methods can be modified. For example, the bacterial DNA can be modified by insertion, deletion or replacement of nucleic acid. The nucleic acid can be endogenous or exogenous to the bacterium. In some examples, the bacterium is modified so that does not express lipopolysaccharide (LPS) or expresses LPS that lacks the myristic acid moiety of lipid A. In some examples, the msbB gene is modified, such as by mutation, deletion, or replacement. In other examples, the bacterium can be cured of one or more extrachromosomal plasmids. For example, where the bacterium is a Nissle bacterium, one or both of the extrachromosomal plasmids, pMut1 and pMut2, can be removed from the bacterium.

In some examples, the bacteria contain a heterologous nucleic acid that encodes a detectable protein or a protein that induces a detectable signal. The heterologous nucleic acid can be operably linked to an inducible promoter. Such promoters can be induced in vivo, for example, by administration of an inducer molecule by a method of administration, such as orally, for example, by feeding, or injected, such as by intravenous injection. An exemplary inducible promoter is a sugar-inducible promoter, such as an arabinose- or xylose-inducible promoter.

Provided herein are methods of detecting and/or imaging a site of proliferation by administering a non-pathogenic bacterium that localizes to the site of proliferation and detecting the accumulation of a radiolabeled compound in the localized bacterium using a method such as position emission tomography, planar gamma imaging, single photon emission computed tomography, where the site of proliferation, such as a tumor, also is detected and/or imaged by detecting/imaging detectable protein or a signal induced by a bacterially expressed protein. Exemplary of detectable proteins or proteins that induce a detectable signal are fluorescent proteins, luminescent proteins or proteins that can bind a contrast agent, chromophore or a compound or ligand for visualization.

Provided herein are methods of treatment of a subject that has a site of proliferation or a proliferative condition where the site of proliferation is imaged and/or detected by administering a non-pathogenic bacterium that localizes to the site of proliferation and detecting/imaging the accumulation of a radiolabeled compound in the localized bacterium and the subject is administered a therapeutic agent for the treatment of the site of proliferation or proliferative condition. In some examples the subject has a tumor or metastasis and the therapeutic agent is, for example, an anti-tumor or anti-cancer agent. The therapeutic agent can be administered sequentially or simultaneously with the non-pathogenic bacteria. Exemplary therapeutic agents include, but are not limited to, cytokines, growth factors, photosensitizing agents, radionuclides, toxins, anti-metabolites, signaling modulators, anti-cancer antibiotics, anti-cancer antibodies, angiogenesis inhibitors, and chemotherapeutic compounds.

Provided herein are methods of treatment of a subject that has a site of proliferation or a proliferative condition where the site of proliferation is imaged and/or detected by administering a non-pathogenic bacterium that localizes to the site of proliferation and detecting/imaging the accumulation of a radiolabeled compound in the localized bacterium and the bacterium contain a heterologous nucleic acid that encodes a product for therapy of a tumor, tumor tissue, wound, wound tissue, site of inflammation and inflamed tissue. Exemplary therapeutic products include, but are not limited to, cell-surface receptors, cytokines, chemokines, apoptotic proteins, antimitotic oligopeptides, toxins, tumor antigens, prodrug converting enzymes and therapeutic RNA molecules.

Provided herein are uses of a radiolabeled compound in combination with Escherichia coli Nissle strain bacterium for formulation of a medicament for detection of a site of proliferation in a subject, wherein the radiolabeled compound is a radiolabeled nucleoside analog. Exemplary radiolabeled compounds contain a radioisotope selected from among $^{123}$I, $^{124}$I, $^{125}$I, $^{131}$I, $^{18}$F, $^{19}$F, $^{11}$C, $^{13}$C, $^{14}$C, $^{75}$Br, $^{76}$Br, and $^{3}$H. Exemplary nucleoside analogs for use in the preparation of medicament include 1-(2'deoxy-2'-fluoro-β-D-arabinofuranosyl)-5-iodouracil (FIAU), 1-(2'deoxy-2'-fluoro-β-D-arabinofuranosyl)-5-ethyluracil (FEAU), 1-(2'-deoxy-2'-fluoro-β-D-arabinofuranosyl)-5-methyluracil (FMAU), 3'-deoxy-3'-fluorothymidine (FLT), 9-[4'-fluoro-3'-(hydroxymethyl)butyl]guanine (FHBG) and 9-[(3'-fluoro-1'-hydroxy-2'-propoxy)methyl]guanine (FHPG). Exemplary the radiolabeled compound for use in the preparation of medicament include, but are not limited to [$^{125}$I]-1-(2'deoxy-2'-fluoro-β-D-arabinofuranosyl)-5-iodouracil ([$^{125}$I]-FIAU), [$^{124}$I]-1-(2'deoxy-2'-fluoro-β-D-arabinofuranosyl)-5-iodouracil ([$^{124}$I]-FIAU), [$^{18}$F]-1-(2'deoxy-2'-fluoro-β-D-arabinofuranosyl)-5-iodouracil ([$^{18}$F]-FIAU), [$^{18}$F]-1-(2'-deoxy-2'-fluoro-β-D-arabinofuranosyl)-5-ethyluracil ([$^{18}$F]-FEAU), [$^{18}$F]-1-(2'-deoxy-2'-fluoro-β-D-arabinofuranosyl)-5-methyluracil ([$^{18}$F]-FMAU), [$^{18}$F]-3'-deoxy-3'-fluorothymidine ([$^{18}$F]-FLT), [$^{18}$F]-9-[4'-fluoro-3'-(hydroxymethyl)butyl]guanine ([$^{18}$F]-FHBG) and [$^{18}$F]-9-[(3'-fluoro-1'-hydroxy-2'-propoxy)methyl]guanine ([$^{18}$F]-FHPG). In some examples, the radiolabeled compound and bacterium are formulated separately. In some examples, the bacterium and the radiolabeled compound are formulated in a single composition. In some examples, bacterium and/or the radiolabeled compound are formulated for systemic administration. In some examples, the medicament contains an anti-tumor or anti-cancer agent. Exemplary anti-tumor or anti-cancer agents include, but are not limited to, cytokines, growth factors, photosensitizing agents, radionuclides, toxins, anti-metabolites, signaling modulators, anti-cancer antibiotics, anti-cancer antibodies, angiogenesis inhibitors, and chemotherapeutic compounds. In some examples, the bacterium contained in the medicament encodes a product for therapy of a tumor, tumor tissue, wound, wound tissue, site of inflammation and inflamed tissue. Exemplary therapeutic products include, but are not limited to cell-surface receptors, cytokines, chemokines, apoptotic proteins, antimitotic oligopeptides, toxins, tumor antigens, prodrug converting enzymes and therapeutic RNA molecules.

Provided herein are combinations containing a composition containing an Escherichia coli Nissle strain bacterium and a composition containing a radiolabeled nucleoside analog. In such combinations, the composition containing an Escherichia coli Nissle strain bacterium can contain an amount of bacteria sufficient for the bacteria to replicate in a tumor or metastasis in a subject. In such combinations, the composition containing a radiolabeled nucleoside analog contains an amount of the nucleoside analog sufficient to produce a detectable signal in a subject. In some examples, the combination contains $1\times10^3$ or about $1\times10^3$ cfu colony forming units (cfu), $1\times10^4$ or about $1\times10^4$ cfu, $1\times10^4$ or about $1\times10^5$ cfu, $1\times10^6$ or about $1\times10^6$ cfu, $1\times10^7$ or about $1\times10^7$ cfu, $5\times10^7$ or about $5\times10^7$ cfu, $1\times10^8$ or about $1\times10^8$ cfu, $1\times10^9$ or about $1\times10^9$ cfu, $1\times10^{10}$ or about $1\times10^{10}$ cfu, $5\times10^{10}$ or about $5\times10^{10}$ cfu, $1\times10^{11}$ or about $1\times10^{11}$ cfu or $5\times10^{11}$ or about $5\times10^{11}$ cfu of the bacterium. In some examples, the combination contains about or 1 mg, about or 10 mg, about or 50 mg, about or 100 mg, about or 200 mg, about or 300 mg, about or 400 mg, about or 500 mg, about or 600 mg, about or 700 mg, about or 800 mg, about or 900 mg, about or 1000 mg, about or 1500 mg, about or 2000 mg or about or 2500 mg of the nucleoside analog. In some examples, the Nissle bacteria express an endogenous thymidine kinase and the radiolabeled nucleoside analog binds to the thymidine kinase. In some examples, the thymidine kinase phosphorylates the radiolabeled nucleoside analog. In some examples, the radioisotope of the radiolabeled nucleoside analog directly or indirectly emits gamma radiation. Exemplary radioisotopes include $^{123}$I, $^{124}$I, $^{125}$I, $^{131}$I, $^{18}$F, $^{19}$F, $^{11}$C, $^{13}$C, $^{14}$C, $^{75}$Br, $^{76}$Br, and $^{3}$H. Exemplary nucleoside analogs in such combinations include, but are not limited to, radioloabeled forms of 1-(2'deoxy-2'-fluoro-β-D-arabinofuranosyl)-5-iodouracil (FIAU), 1-(2'deoxy-2'-fluoro-β-D-arabinofuranosyl)-5-ethyluracil (FEAU), 1-(2'-deoxy-2'-fluoro-β-D-arabinofuranosyl)-5-methyluracil (FMAU), 3'-deoxy-3'-fluorothymidine (FLT), 9-[4'-fluoro-3'-(hydroxymethyl)butyl]guanine (FHBG) and 9-[(3'-fluoro-1'-hydroxy-2'-propoxy)methyl]guanine (FHPG). Exemplary radiolabeled nucleoside analogs in such combinations include, but are not limited to, [$^{125}$I]-1-(2'deoxy-2'-fluoro-β-D-arabinofuranosyl)-5-iodouracil ([$^{125}$I]-FIAU), [$^{124}$I]-1-(2'deoxy-2'-fluoro-β-D-arabinofuranosyl)-5-iodouracil ([$^{124}$I]-FIAU), [$^{18}$F]-1-(2'deoxy-2'-fluoro-β-D-arabinofuranosyl)-5-iodouracil ([$^{18}$F]-FIAU), [$^{18}$F]-1-(2'deoxy-2'-fluoro-β-D-arabinofuranosyl)-5-ethyluracil ([$^{18}$F]-FEAU), [$^{18}$F]-1-(2'-deoxy-2'-fluoro-β-D-arabinofuranosyl)-5-methyluracil ([$^{18}$F]-FMAU), [$^{18}$F]-3'-deoxy-3'-fluorothymidine ([$^{18}$F]-FLT), [$^{18}$F]-9-[4'-fluoro-3'-(hydroxymethyl)butyl]guanine ([$^{18}$F]-FHBG) and [$^{18}$F]-9-[(3'-fluoro-1'-hydroxy-2'-propoxy)methyl]guanine ([$^{18}$F]-FHPG). Provided herein are kits that contain a combination containing a composition containing an Escherichia coli Nissle strain bacterium and a composition containing a radiolabeled nucleoside analog.

DETAILED DESCRIPTION

Outline
A. Definitions
B. Methods and Compositions for Detection and Therapy
C. Bacteria for Use in the Methods
 1. Non-pathogenic
 2. Accumulation in tumors and other immunoprivileged sites
 3. Expression of endogenous proteins for detection D. Modifications of Bacteria for Use in the Methods
1. Expression of Exogenous Genes
2. Inactivation of Genes
E. Imaging
1. Administration for detection and/or monitoring treatment
2. Dosages for detection and/or monitoring treatment
F. Therapy
1. Administration
   a. Steps prior to administering the bacteria
   b. Mode of administration
   c. Dosage
   d. Number of administrations
2. Co-administrations
   a. Other therapeutic agents, compounds and gene products
   b. Therapeutic gene product expression
3. State of subject
4. Monitoring tumor size
5. Monitoring general health diagnostics
G. Pharmaceutical compositions, Combinations and Kits
1. Pharmaceutical compositions
2. Combinations
3. Kits
H. Examples

A. DEFINITIONS

Unless defined otherwise, all technical and scientific terms used herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, the term "microorganism" or "microbe" refers to a life form or organism of small size, generally microscopic in size. Thus, for example, the term "microorganism" includes organisms, such as bacteria, archaea, fungi and protists, and viruses. Microorganisms include eukaryotic and prokaryotic organisms and can be unicellular or multicellular. Although the term "microorganism" as used herein includes unicellular organisms, it does not include a single cell that is not an organism per se but that rather is a cell that occurs in nature as a part of a larger multicellular organism.

As used herein, the term "cell" refers to the basic unit of structure and function of a living organism as is commonly understood in the biological sciences. A cell can be a unicellular organism that is self-sufficient and that can exist as a functional whole independently of other cells. A cell can also be one that, when not isolated from the environment in which it occurs in nature, is part of a multicellular organism made up of more than one type of cell. Such a cell, which can be thought of as a "non-organism" or "non-organismal" cell, generally is specialized in that it performs only a subset of the functions performed by the multicellular organism as whole. Thus, this type of cell is not a unicellular organism. Such a cell can be a prokaryotic or eukaryotic cell, including animal cells such as mammalian cells, human cells and non-human animal cells or non-human mammalian cells. Animal cells include any cell of animal origin that can be found in an animal. Thus, animal cells include, for example, cells that make up the various organs, tissues and systems of an animal.

As used herein, the term "tissue" refers to a group, collection or aggregate of similar cells generally acting to perform a specific function within an organism.

As used herein, the terms immunoprivileged cells and tissues refer to cells and tissues, such as solid tumors and wounded tissues, which are sequestered from the immune system. Generally, administration of a bacteria elicits an immune response that clears the bacteria; immunoprivileged sites, however, are shielded or sequestered from the immune response, permitting the bacteria to survive and generally to replicate. Immunoprivileged tissues include inflamed tissues, wounded tissues, and proliferating tissues, such as tumor tissues.

As used herein, the term "detect," "detecting" or "detection" with reference to a composition such as, for example, a bacterium, includes any process whereby the presence of the composition is determined. For example, detection of the composition can be direct or indirect. Direct detection involves using a directly detectable feature of the composition itself as a basis for determining its presence. One example of direct detection is detection of light emitted by a composition, such as bacteria that express a fluorescent or luminescent protein. Indirect detection is not based on detecting a directly detectable feature of the composition but rather can involve detection of any detectable feature that is specifically associated with the presence of the composition. For example, indirect detection can involve detection of a detectably labeled ligand that interacts with or binds to the composition (e.g., a bacterium) or can involve detection of a biochemical or physiological effect of the presence of the composition in a subject. Detection can involve any manner of techniques, including use of a signal, such as magnetic resonance imaging, ultrasound signal, X-rays, gamma rays (after annihilation of a positron and an electron in PET scanning), fluorescence or absorption.

As used herein, the recitation that a compound interacts with an endogenous bacterial protein is intended to refer to the binding of the compound to the protein. In some examples, the endogenous bacterial protein is an enzyme, such as a bacterial thymidine kinase. In such examples, the compound can bind to and be phosphorylated by the kinase.

As used herein, "modified" with reference to a gene refers to a deleted gene or a gene having one or more truncations, mutations, insertions or deletions. A gene modification can be such that it results in truncation, mutation, an insertion or a deletion of a part or all of a gene product encoded by the gene. A gene modification can be accompanied by a change in function of the gene product and/or a property of the bacteria.

As used herein, to attenuate toxicity of a bacterium means to reduce or eliminate deleterious or toxic effects to a host upon administration of the bacterium compared to an unattenuated bacterium. As used herein, a bacterium with low toxicity means that upon administration, the bacterium does not accumulate in organs and tissues in the host to an extent that results in damage or harm to organs, or that impacts survival of the host to a greater extent than the disease being treated does.

As used herein, accumulation of bacteria in a targeted tissue refers to the distribution of the bacteria throughout the organism after a time period long enough for the microbes to infect the host's organs or tissues. As one skilled in the art will recognize, the time period for infection of a microbe will vary depending on the microbe, the targeted organ(s) or tissue(s), the immunocompetence of the host, and dosage. Generally, accumulation can be determined at time point from about less than 1 day, about 1 day to about 1 week, about 1 week to about 2, 3 or 4 weeks, about 1 month to about 2, 3, 4, 5, 6 months or longer after infection with the microbes. For purposes herein, the bacteria preferentially accumulate in the target tissue, such as a tumor, but are cleared from other tissues and organs in the host to the extent that toxicity of the bacteria is mild or tolerable and at most not fatal. As used herein, preferential accumulation refers to accumulation of bacteria at a first location at a higher level than accumulation at a second location. Thus, bacteria that preferentially accumulates in immunoprivileged tissue such as tumor relative to normal tissues or organs refers to bacteria that accumulate in immunoprivileged tissue, such as tumor, at a higher level (concentration) than the bacteria accumulate in normal tissues or organs.

As used herein, a compound produced in a tumor or other immunoprivileged site refers to any compound that is produced in the tumor or tumor environment by virtue of the presence of an introduced bacterium, generally a recombinant bacterium, expressing one or more gene products. For example, a compound produced in a tumor can be, for example, a metabolite, an encoded polypeptide or RNA, or compound that is generated by a recombinant polypeptide (e.g., cell-surface receptor, a siderophore, a ferritin, an enzyme) and the cellular machinery of the tumor or immunoprivileged tissue or cells.

As used herein, "commensal" when used in reference to an association between two organisms, is a particular association in which one member of the association benefits from the association while the other member is essentially unaffected. In a commensal association of organisms, none of the members of the association is significantly harmed by the presence of the other member. Two organisms can form a commensal association under particular, but not necessarily all, conditions. In such cases, as long as an organism is capable of forming a commensal association with the other organism under at least one set of conditions, the organism is considered to be one that can form a commensal association with the other organism.

As used herein, "mutual" when used in reference to an association between two or more organisms, is a particular association which is advantageous to both members of the association. In a mutual association of organisms, none of the members of the association is significantly harmed by the presence of the other member. Two organisms can form a mutual association under particular, but not necessarily all, conditions. In such cases, as long as an organism is capable of forming a mutual association with the other organism under at least one set of conditions, the organism is considered to be one that can form a mutual association with the other organism.

As used herein, a probiotic bacterium refers to a bacterium that confers a benefit to a host in which it can occur. The benefit can be, for example, an overall health benefit to the host, such as preventing, maintaining remission of, preventing recurrence of, reversing or reducing the symptoms or detrimental effects of a disorder or disease of the host. Such disorders/diseases include, but are not limited to, infectious diseases, inflammation, diarrhea (e.g., antibiotic-induced diarrhea, infectious diarrhea and traveler's diarrhea), inflammatory bowel disease, Crohn's disease, pouchitis and colitis. The benefit conferred by a probiotic bacterium can be stabilization of the host microbiota or microecology, for example, by improving the microbial balance of the indigenous microflora (Kruis W. (2004) *Pharmacol. Ther.* 20 (Suppl 4): 75-78).

Probiotic bacteria can exert their effects in a number of ways. For example, probiotic bacteria can interfere with harmful properties of other pathogenic bacteria that can occur through the production of antimicrobial substances by the probiotic bacteria and interference with bacterial attachment/penetration to/into host cells. A probiotic bacterium also can stimulate a host to produce antimicrobial molecules, alter a host's immune response, stimulate mucosal barrier function or alter immunoregulation, such as by decreasing pro-inflammatory molecules and promoting protective molecules (Sartor R B. (2005) *Curr. Opin. Gastroenterol.* 21(1): 44-50). Exemplary probiotic bacteria include, but are not limited to, *E. coli* strain Nissle 1917 (O6:K5:H1; Mutaflor; Ardeypharm GmbH, Germany; Schultz et al. *J Microbiol. Methods* 61(3): 389-398 (2005)). *E. coli* strain Nissle 1917 lacks defined virulence factors such as alpha-hemolysin, other toxins, and mannose-resistant hemagglutinating adhesins (Blum et al. *Infection.* 23(4):234-236 (1996)), P-fimbrial adhesins, and the semirough lipopolysaccharide phenotype and expresses fitness factors such as microcins, ferritins, six different iron uptake systems, adhesins, and proteases, which support its survival and successful colonization of the human gut (Grozdanov et al. (2004) *J Bacteriol.* 186(16): 5432-5441). *E. coli* Nissle 1917 interferes with bacterial invasion of other bacteria cells via a secreted component (Altenhoefer et al. (2004) *FEMS Immunol. Med. Microbiol.* 40(3): 223-9). *E. coli Nissle* 1917 can have plasmids (Mutaflor O6:K5:H1, DSM 6601 by Medipharm, Kä geröd, Sweden) or no plasmids (i.e. can be cured of plasmids).

As used herein, angiogenesis is encompasses the totality of processes directly or indirectly involved in the establishment and maintenance of new vasculature (neovascularization), including, but not limited to, neovascularization associated with tumors and neovascularization associated with wounds.

As used herein, "disease or disorder" refers to a pathological condition in an organism resulting from, for example, infection or genetic defect, and characterized by identifiable symptoms.

As used herein, neoplasia refers to the process of abnormal growth, for example, of a cell, tissue or organ. The growth is abnormal in that it is an uncontrolled, generally unrestrained and progressive multiplication of cells typically under conditions that would not normally induce growth and/or that normally would prevent growth. Such abnormal growth can result in the generation of an abnormal mass, referred to as a neoplasm or tumor, which can be benign or malignant. Unlike hyperplasia, neoplastic proliferation persists even in the absence of the original stimulus.

As used herein, neoplastic disease refers to any disease or disorder associated with neoplasia, whether benign or malignant. Examples of such diseases or disorders include, but are not limited to, malignant neoplastic diseases or disorders involving cancer, including tumor development, growth, metastasis and progression. For example, hematological malignancies affecting blood, bone marrow and/or lymph nodes, including leukemia, lymphoma and multiple myeloma, are types of neoplastic diseases or disorders.

As used herein, malignant, as it applies to tumors, refers to primary tumors that have the capacity to invade surrounding tissues and metastasize with loss of growth control and positional control. In contrast, benign tumors do not invade surrounding tissues or metastasize to other areas of an organism.

As used herein, metastasis refers to a growth of abnormal or neoplastic cells distant from the site primarily involved by the morbid process. For example, in the metastatic process, malignant cells can spread from the site of the primary tumor in which they arose and move into lymphatic and blood vessels which transport the cells to normal tissues elsewhere in an organism where the cells continue to proliferate.

As used herein, cancer is a general term for diseases caused by or characterized by any type of malignant tumor. Exemplary cancers include, but are not limited to carcinoma, sarcoma, mesothelioma, and, in particular, pancreatic cancer, lung cancer, ovarian cancer, breast cancer, cervical cancer, bladder cancer, prostate cancer, colorectal cancer, glioma tumors, adenocarcinomas, liver cancer and skin cancer.

As used herein, the term "proliferative condition" refers to any abnormal condition that includes proliferation and/or recruitment of cells. While the condition is abnormal, the cellular proliferation that occurs in the condition can be considered normal or abnormal. For example, the cellular proliferation can be a transient increase in cell numbers such as might occur in typically normal physiological processes including, but not limited to, wound healing and immune responses, for example as occurs in the inflammatory response. The cellular proliferation can be abnormal, such as occurs in neoplasia (both benign and malignant), excessive, misdirected and/or inappropriate immune responses and hyperplasia. An area in which such a proliferative condition occurs is referred to herein as a proliferative site or site of proliferation.

As used herein, hyperplasia refers to an increase in the number of cells of an organ or tissue and generally is associated with an increase in size of the organ or tissue. Examples of hyperplasia include, but are not limited to, polycystic ovary syndrome, congenital adrenal hyperplasia, benign prostatic hyperplasia and hyperplasia of the breast (e.g., benign ductal or lobular hyperplasia).

As used herein, inflammation refers to a condition normally arising due to an immune response to a stimulus, such as, an external or internal insult, for example, an infection (e.g., fungal, parasitic, bacterial or viral), foreign substance or irritation. Inflammation can be local or systemic within an organism and is often characterized by swelling, pain, redness as well as organ dysfunction. Inflammation involves the movement of fluid and cells (e.g., white blood cells or leukocytes, neutrophils, monocytes and T- and B-cells) into the affected area, site or tissue. In some instances, the immune system can trigger an inflammatory response in the absence of a typical insult. Such excessive, misdirected and/or inappropriate immune inflammatory responses can lead to damage of normal, healthy body tissues and are associated with certain diseases and disorders, including, for example, autoimmune diseases and disorders. There are a number of diseases and disorders that can involve inflammation, both neoplastic and non-neoplastic or non-malignant (benign) diseases. Examples of such diseases and disorders include, but are not limited to, arteritis, arthritis, psoriasis, fibroproliferative disorders, restinosis, stenosis, neurodegenerative diseases, sepsis, appendicitis, myocarditis, nephritis, colitis, gastritis, atherosclerosis or arteriosclerosis, inflammatory bowel disease, systemic lupus erythematosis, multiple sclerosis, type 1 diabetes, Crohn's disease, and coronary artery disease.

As used herein, the term "wound" refers to a physical trauma to an organism that can damage cells, tissues, organs and systems of the organism. Wounds include open wounds, such as incisions, burns, lacerations, abrasions, puncture wounds and penetration wounds, which are exposed to the environment, and closed wounds, which are typically internal to the organism and include, for example, contusions, hematomas and crushing injuries.

As used herein, an anti-cancer agent or compound (used interchangeably with "anti-tumor or anti-neoplastic agent") refers to any agents, or compounds, used in anti-cancer treatment. These include any agents, when used alone or in combination with other compounds, that can alleviate, reduce, ameliorate, prevent, or place or maintain in a state of remission of clinical symptoms or diagnostic markers associated with neoplastic disease, tumors and cancer, and can be used in methods, combinations and compositions provided herein. Exemplary anti-neoplastic agents include, but are not limited to, the bacteria used in the methods provided herein used singly or in combination and/or in combination with other agents, such as alkylating agents, anti-metabolite, certain natural products, platinum coordination complexes (e.g., cisplatin, carboplatin, and oxaliplatinum), anthracenediones, substituted ureas, methylhydrazine derivatives, adrenocortical suppressants, certain hormones, antagonists and anti-cancer polysaccharides.

As used herein, a method for treating or preventing neoplastic disease means that any of the symptoms, such as the tumor, metastasis thereof, the vascularization of the tumors or other parameters by which the disease is characterized are reduced, ameliorated, prevented, placed in a state of remission, or maintained in a state of remission. It also means that the hallmarks of neoplastic disease and metastasis can be eliminated, reduced or prevented by the treatment. Non-limiting examples of the hallmarks include uncontrolled degradation of the basement membrane and proximal extracellular matrix, migration, division, and organization of the endothelial cells into new functioning capillaries, and the persistence of such functioning capillaries.

As used herein, therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that inhibit cell growth or promote cell death, that can be activated to inhibit cell growth or promote cell death, or that activate another agent to inhibit cell growth or promote cell death. Optionally, the therapeutic agent can exhibit or manifest additional properties, such as, properties that permit its use as an imaging agent, as described elsewhere herein. Exemplary therapeutic agents include, for example, cytokines, growth factors, photosensitizing agents, radionuclides, toxins, anti-metabolites, signaling modulators, anti-cancer antibiotics, anti-cancer antibodies, angiogenesis inhibitors, radiation therapy, chemotherapeutic compounds or a combination thereof.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound is regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392). Prodrugs include, but are not limited to, 5-fluorouracil, gancyclovir, and other as described elsewhere herein.

As used herein, a compound conjugated to a moiety refers to a complex that includes a compound bound to a moiety, where the binding between the compound and the moiety can arise from one or more covalent bonds or non-covalent interactions such as hydrogen bonds, or electrostatic interactions. A conjugate also can include a linker that connects the compound to the moiety. Exemplary compounds include, but are not limited to, nanoparticles and siderophores. Exemplary moieties, include, but are not limited to, detectable moieties and therapeutic agents.

As used herein, nanoparticle refers to a microscopic particle whose size is measured in nanometers. Often such particles in nanoscale are used in biomedical applications acting as drug carriers or imaging agents. Nanoparticles can be conjugated to other agents, including, but not limited to detectable/diagnostic agents or therapeutic agents.

As used herein, a detectable label or detectable moiety or diagnostic moiety (also imaging label, imaging agent, or imaging moiety) refers to an atom, molecule or composition, wherein the presence of the atom, molecule or composition can be directly or indirectly measured. As used herein, a detectable moiety or an imaging moiety refer to moieties used to image bacteria in any of the methods provided herein. Imaging (detectable) moieties include, for example, chemiluminescent moieties, bioluminescent moieties, fluorescent moieties, radionuclides and metals. Such a label can be detected, for example, by visual inspection, by fluorescence spectroscopy, by reflectance measurement, by flow cytometry, by X-rays, by a variety magnetic resonance methods such as magnetic resonance imaging (MRI) and magnetic resonance spectroscopy (MRS), and also include any of a variety of tomographic methods including computed tomography (CT), computed axial tomography (CAT), electron beam computed tomography (EBCT), high resolution computed tomography (HRCT), hypocycloidal tomography, positron emission tomography (PET), single-photon emission computed tomography (SPECT), spiral computed tomography and ultrasonic tomography. Direct detection of a detectable label refers to, for example, measurement of a physical phenomenon, such as energy or particle emission (e.g., PET or SPECT) or absorption of the moiety itself, such as by X-ray or MRI. Indirect detection refers to measurement of a physical phenomenon, such as energy or particle emission or absorption, of an atom, molecule or composition that binds directly or indirectly to the detectable moiety. In a non-limiting example of indirect detection, a detectable label can be biotin, which can be detected by binding to avidin. Non-labeled avidin can be administered systemically to block non-specific binding, followed by systemic administration of labeled avidin. Thus, included within the scope of a detectable label or detectable moiety is a bindable label or bindable moiety, which refers to an atom, molecule or composition, wherein the presence of the atom, molecule or composition can be detected as a result of the label or moiety binding to another atom, molecule or composition. Exemplary diagnostic agents include, for example, metals such as colloidal gold, iron, gadolinium, and gallium-67, fluorescent moieties and radionuclides. Exemplary fluorescent moieties and radionuclides are provided elsewhere herein.

As used herein, a radiolabeled compound is any compound that is attached to a radionuclide or includes one or more atoms that are radionuclides. For example, [$^{18}$F]-1-(2'deoxy-2'-fluoro-β-D-arabinofuranosyl)-5-ethyluracil ([$^{18}$F]-FEAU) is a radiolabeled compound that had the radionuclide $^{18}$F incorporated at the 2'-fluoro position of the molecule. Exemplary radiolabeled compounds include radiolabeled nucleoside analogs, such as, but not limited to, [$^{125}$I]-1-(2'deoxy-2'-fluoro-β-D-arabinofuranosyl)-5-iodouracil ([$^{125}$I]-FIAU), [$^{124}$I]-1-(2'deoxy-2'-fluoro-β-D-arabinofuranosyl)-5-iodouracil ([$^{124}$I]-FIAU), [$^{18}$F]-1-(2'deoxy-2'-fluoro-β-D-arabinofuranosyl)-5-iodouracil ([$^{18}$F]-FIAU), [$^{18}$F]-1-(2'deoxy-2'-fluoro-β-D-arabinofuranosyl)-5-ethyluracil ([$^{18}$F]-FEAU), [$^{18}$F]-1-(2'-deoxy-2'-fluoro-β-D-arabinofuranosyl)-5-methyluracil ([$^{18}$F]-FMAU), [$^{18}$F]-3'-deoxy-3'-fluorothymidine ([$^{18}$F]-FLT), [$^{18}$F]-9-[4'-fluoro-3'-(hydroxymethyl)butyl]guanine ([$^{18}$F]-FHBG) and [$^{18}$F]-9-[(3'-fluoro-1'-hydroxy-2'-propoxy)methyl]guanine ([$^{18}$F]-FHPG).

As used herein, a radionuclide, a radioisotope or radioactive isotope is used interchangeably to refer to an atom with an unstable nucleus. The nucleus is characterized by excess energy which is available to be imparted either to a newly-created radiation particle within the nucleus, or else to an atomic electron. The radionuclide, in this process, undergoes radioactive decay, and emits a gamma ray and/or subatomic particles. Such emissions can be detected in vivo by method such as, but not limited to, positron emission tomography (PET), single-photon emission computed tomography (SPECT) or planar gamma imaging. Radioisotopes can occur naturally, but can also be artificially produced. Exemplary radionuclides for use in vivo imaging include, but are not limited to, $^{11}$C, $^{11}$F, $^{13}$N, $^{15}$N, $^{15}$O, $^{18}$F, $^{19}$F, $^{32}$P, $^{52}$Fe, $^{51}$Cr, $^{55}$Co, $^{55}$Fe, $^{57}$Co, $^{57}$Ni, $^{59}$Fe, $^{60}$Co, $^{64}$Cu, $^{67}$Ga, $^{68}$Ga, $^{60}$Cu(II), $^{67}$Cu(II), $^{99}$Tc, $^{90}$Y, $^{99}$Tc, $^{103}$Pd, $^{106}$Ru, $^{111}$In, $^{117}$Lu, $^{123}$I, $^{124}$I, $^{125}$I, $^{131}$I, $^{137}$Cs, $^{153}$Gd, $^{153}$Sm, $^{186}$, $^{188}$Re, $^{192}$Ir, $^{198}$Au, $^{211}$At, $^{212}$Bi, $^{213}$Bi and $^{241}$Am. Radioisotopes can be incorporated into or attached to a compound, such as a metabolic compound. Exemplary radionuclides that can be incorporated or linked to a metabolic compound, such as nucleoside analog, include, but are not limited to, $^{123}$I, $^{124}$I, $^{125}$I, $^{131}$I, $^{18}$F, $^{19}$F, $^{11}$C, $^{13}$C, $^{14}$C, $^{75}$Br, $^{76}$Br, and $^{3}$H.

As used herein a metabolic compound refers to any compound that is utilized in or is a product of a metabolic pathway (e.g., glycolysis, glycogen synthesis, DNA synthesis). The metabolic compounds for use in the methods provided herein are synthetic analogs or derivatives of natural metabolic products. Such compounds can be taken up by a cell or microorganism, such as a bacterium that is localized to a site of proliferation. The metabolic compounds for use in the methods provided herein typically interact with one or more endogenous enzymes of the cell or microorganism. Exemplary metabolic compounds for use in the method provided herein include nucleoside analogs. Such analogs, when taken up by a microorganism such as a bacteria, can interact with one or more endogenous enzymes, such as a bacterial thymidine kinase. In some examples, the bacterial thymidine kinase, phosphorylates the nucleoside analog. Exemplary nucleoside analogs include, but are not limited to, 1-(2'deoxy-2'-fluoro-β-D-arabinofuranosyl)-5-iodouracil (FIAU), 1-(2'deoxy-2'-fluoro-β-D-arabinofuranosyl)-5-ethyluracil (FEAU), 1-(2'-deoxy-2'-fluoro-β-D-arabinofuranosyl)-5-methyluracil (FMAU), 3'-deoxy-3'-fluorothymidine (FLT), 9-[4'-fluoro-3'-(hydroxymethyl)butyl]guanine (FHBG) and 9-[(3'-fluoro-1'-hydroxy-2'-propoxy)methyl]guanine (FHPG). The nucleoside analogues can be synthesized to incorporate a radioactive label, such as, for example, $^{123}$I, $^{124}$I, $^{125}$I, $^{131}$I, $^{18}$F, $^{19}$F, $^{11}$C, $^{13}$C, $^{14}$, $^{75}$Br, $^{76}$Br, and $^{3}$H, at one or more positions in the molecule.

As used herein, accumulation of a radiolabeled compound in vivo refers the accumulation of one or more molecules of the radiolabeled compound at a particular site in the subject to whom the radiolabeled compound was administered. For the methods provided herein, the radiolabeled compound typically accumulates at sites of bacterial accumulation, including, for example, sites of cellular proliferation, such as tumors, tumor tissues, metastases, areas of inflammation, immunoprivileged sites or tissues, wounds or infections.

As used herein, an in vivo method refers to a method performed within the living body of a subject.

As used herein, a subject includes any organism, including an animal, for whom diagnosis, screening, monitoring or treatment is contemplated. Animals include mammals such as primates and domesticated animals. An exemplary primate is human. A patient refers to a subject such as a mammal, primate, human or livestock subject afflicted with a disease condition or for which a disease condition is to be determined or risk of a disease condition is to be determined.

As used herein, treatment means any manner in which the symptoms of a condition, disorder or disease are ameliorated or otherwise beneficially altered. Treatment also encompasses any pharmaceutical use of the bacteria used in the methods provided herein.

As used herein, amelioration of the symptoms of a particular disorder such as by administration of a particular pharmaceutical composition refers to any lessening, whether permanent or temporary, lasting or transient that can be attributed to or associated with administration of the composition.

As used herein, an effective amount of bacteria or compound for treating a particular disease is an amount that is sufficient to ameliorate, or in some manner reduce the symptoms associated with the disease. Such an amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms. As used herein, administration of a bacterium to a subject is understood to include administration of a plurality of a particular bacterium to the subject.

As used herein, nucleic acids include DNA, RNA and analogs thereof, including peptide nucleic acids (PNA) and mixtures thereof. Nucleic acids can be single or double-stranded. Gene can encode, for example, DNA, DNA encoding regulatory RNAs, siRNAs or functional RNAs. When referring to probes or primers, which are optionally labeled, such as with a detectable label, such as a fluorescent or radiolabel, single-stranded molecules are provided. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 5, 6, 7, 8, 9, 10 or more, 20 or more, 30 or more, 50 or more, 100 or more nucleic acids long.

As used herein, operative linkage of heterologous nucleic acids to regulatory and effector sequences of nucleotides, such as promoters, enhancers, transcriptional and translational stop sites, and other signal sequences refers to the relationship between such nucleic acid, such as DNA, and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA. Thus, operatively linked or operationally associated refers to the functional relationship of a nucleic acid, such as DNA, with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or transcription, it can be necessary to remove, add or alter 5' untranslated portions of the clones to eliminate extra, potentially inappropriate alternative translation initiation (i.e., start) codons or other sequences that can interfere with or reduce expression, either at the level of transcription or translation. In addition, consensus ribosome binding sites can be inserted immediately 5' of the start codon and can enhance expression (see, e.g., Kozak *J. Biol. Chem.* 266: 19867-19870 (1991); Shine and Dalgarno *Nature* 254(5495): 34-38 (1975)). The desirability of (or need for) such modification can be empirically determined.

As used herein, a promoter region or promoter element or regulatory region refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences can be cis acting or can be responsive to trans acting factors. Promoters, depending upon the nature of the regulation, can be constitutive or regulated. Exemplary promoters contemplated for use in prokaryotes include, but are not limited to, the bacteriophage T7 and T3 promoters, *E. coli* araBAD promoter, *E. coli* ompA promoter, *E. coli* lac promoter (Schnetz (1995) *Embo J.* 14(11):2545-2550), *E. coli* trp promoter (de Boer et al. (1983) *PNAS USA* 80(1):21), *E. coli* tac promoter (deBoer et al. (1983) *PNAS USA* 80(1):21-25), *Bacillus subtilis* rpsJ promoter and *Bacillus megaterium* xylA promoter.

As used herein, production by recombinant means by using recombinant DNA methods means the use of the well known methods of molecular biology for expressing proteins encoded by cloned DNA.

As used herein, vector (or plasmid) refers to discrete elements that are used to introduce heterologous nucleic acid into cells for either expression or replication thereof. The vectors typically remain episomal, but can be designed to effect stable integration of a gene or portion thereof into a chromosome of the genome. Also contemplated are vectors that are artificial chromosomes, such as yeast artificial chromosomes and mammalian artificial chromosomes. Selection and use of such vectors are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Exemplary vectors include, but are not limited to the plasmid vectors ColE1, pBR322, p15A, pEM-BLex2, pMAL-p2, pUC18A2 (a pUC18-derived plasmid containing the fin gene), pUC118, pGS281, pMK4, pUNK1, pAMβ1 and pTA1060.

Methods for modifying vectors (or plasmids) to affect replication and maintenance of the vector in bacteria are well known to one skilled in the art based on the early characterization of the molecule, including its nucleotide sequence, replication and maintenance mechanisms, and determination of its coding regions (Balbas and Bolivar. *Methods Mol. Biol.* 267: 77-90 (2004); Grabherr and Bayer. *Trends Biotechnol.* 20(6): 257-260 (2002); Jung and Lee. Mol. Biol. Rep. 22(2-3): 195-200 (1995-996)).

As used herein, production by recombinant means by using recombinant DNA methods means the use of the well known methods of molecular biology for expressing proteins encoded by cloned DNA.

As used herein, an amplifiable signaling nucleic acid refers to a nucleic acid that can be amplified using known amplification methods such as polymerase chain reaction (PCR).

As used herein, a heterologous nucleic acid (or an exogenous nucleic acid) refers to a nucleic acid that is not normally produced in vivo by the bacteria from which it is expressed or that is produced by the bacteria but is at a different locus or expressed differently or that mediates or encodes mediators that alter expression of endogenous nucleic acid, such as DNA, by affecting transcription, translation, or other regulatable biochemical processes. Heterologous nucleic acid is often not endogenous to the cell into which it is introduced, but has been obtained from another cell or prepared synthetically. Heterologous nucleic acid, however, can be endogenous, but is nucleic acid that is expressed from a different locus or altered in its expression or sequence (e.g., a plasmid). Generally, although not necessarily, such nucleic acid encodes RNA and proteins that are not normally produced by the cell or in the same way in the cell in which it is expressed. Heterologous nucleic acid, such as DNA, also can be referred to as foreign nucleic acid, such as DNA. Thus, heterologous nucleic acid or foreign nucleic acid includes a nucleic acid molecule not present in the exact orientation or position as the counterpart nucleic acid molecule, such as DNA, is found in a genome. It also can refer to a nucleic acid molecule from another organism or species (i.e., exogenous). Any nucleic acid, such as DNA, that one of skill in the art would recognize or consider as heterologous or foreign to the cell in which the nucleic acid is expressed is herein encompassed by heterologous nucleic acid; heterologous nucleic acid includes exogenously added nucleic acid that also is expressed endogenously. Examples of heterologous nucleic acid include, but are not limited to, nucleic acid that encodes exogenous peptides/proteins (e.g., cell surface receptors, siderophores or ferritins), nucleic acid that encodes traceable marker proteins (e.g., a protein that confers drug resistance), nucleic acid that encodes therapeutically effective substances (e.g., anti-cancer agents, enzymes and hormones), and nucleic acid, such as DNA, that encodes other types of proteins, such as antibodies. Antibodies that are encoded by heterologous nucleic acid can be secreted or expressed on the surface of the cell in which the heterologous nucleic acid has been introduced.

As used herein, the terms overproduce or overexpress when used in reference to a substance, molecule, compound or composition made in a bacterium refers to production or expression at a level that is greater than a baseline, normal or usual level of production or expression of the substance, molecule, compound or composition by the cell bacterium. A baseline, normal or usual level of production or expression includes no production/expression or limited, restricted or regulated production/expression. Such overproduction or overexpression is typically achieved by modification of a bacterium. For example, a bacterium can be modified or supplemented to contain extra or additional components, such as nucleic acids, that are involved in the production or expression of the substance, molecule, compound or composition. A bacterium can be modified such that any existing production/expression systems are altered to increase production/expression, such as, for example, eliminating or reducing repression of the expression of an existing gene or altering the timing of expression of a gene. Such modifications can be achieved, for example, using standard methods of recombinant DNA technologies known to those of skill in the art. Such modification is referred to as heterologous overproduction or overexpression and the bacterium is referred to as one that heterologously overproduces or overexpresses. Modification of a bacterium to obtain overproduction or overexpression can be also be achieved by mutagenesis, for example, by subjecting bacterium to conditions, such as growth under particular selective or mutagenic conditions followed by identification of a modified bacterium that overproduces or overexpresses.

As used herein, a therapeutically effective product for gene therapy is a product that is encoded by heterologous nucleic acid, typically DNA, or an RNA product such as dsRNA, RNAi, including siRNA, that upon introduction of the nucleic acid into a host, a product is expressed that ameliorates or eliminates the symptoms, manifestations of an inherited or acquired disease or that cures the disease. Also included are biologically active nucleic acid molecules, such as RNAi and antisense.

As used herein, an agent or compound that modulates the activity of a protein or expression of a gene or nucleic acid either decreases or increases or otherwise alters the activity of the protein or, in some manner, up- or down-regulates or otherwise alters expression of the nucleic acid in a cell.

As used herein, bind, bound and binding refer to the binding between atoms or molecules with a $K_d$ in the range of $10^{-2}$ to $10^{-15}$ mole/L, generally, $10^{-6}$ to $10^{-15}$, $10^{-7}$ to $10^{-15}$ and typically $10^4$ to $10^{-15}$ (and/or a $K_a$ of $10^5$-$10^{12}$, $10^7$-$10^{12}$, $10^8$-$10^{12}$ L/mole).

As used herein, luminescence refers to the detectable electromagnetic (EM) radiation, generally, ultraviolet (UV), infrared (IR) or visible EM radiation that is produced when the excited product of an exergic chemical process reverts to its ground state with the emission of light. Chemiluminescence is luminescence that results from a chemical reaction. Bioluminescence is chemiluminescence that results from a chemical reaction using biological molecules (or synthetic versions or analogs thereof) as substrates and/or enzymes. Fluorescence is luminescence in which light of a visible color is emitted from a substance under stimulation or excitation by light or other forms radiation such as ultraviolet (UV), infrared (IR) or visible EM radiation.

As used herein, chemiluminescence refers to a chemical reaction in which energy is specifically channeled to a molecule causing it to become electronically excited and subsequently to release a photon thereby emitting visible light. Temperature does not contribute to this channeled energy. Thus, chemiluminescence involves the direct conversion of chemical energy to light energy.

As used herein, bioluminescence, which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein (luciferase) that is an oxygenase that acts on a substrate luciferin (a bioluminescence substrate) in the presence of molecular oxygen and transforms the substrate to an excited state, which, upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives such as, for example, click beetle luciferase or firefly luciferase.

As used herein, luciferase refers to oxygenases that catalyze a light emitting reaction. For instance, bacterial luciferases catalyze the oxidation of flavin mononucleotide (FMN) and aliphatic aldehydes, which reaction produces light. Another class of luciferases, found among marine arthropods, catalyzes the oxidation of Cypridina (Vargula) luciferin and another class of luciferases catalyzes the oxidation of Coleoptera luciferin.

Thus, luciferase refers to an enzyme or photoprotein that catalyzes a bioluminescent reaction (a reaction that produces bioluminescence). The luciferases, such as firefly and *Gaussia* and *Renilla luciferases*, are enzymes which act catalytically and are unchanged during the bioluminescence generating reaction. The luciferase photoproteins, such as the aequorin photoprotein to which luciferin is non-covalently bound, are changed, such as by release of the luciferin, during bioluminescence generating reaction. The luciferase is a protein, or a mixture of proteins (e.g., bacterial luciferase), that occurs naturally in an organism or a variant or mutant thereof, such as a variant produced by mutagenesis that has one or more properties, such as thermal stability, that differ from the naturally-occurring protein. Luciferases and modified mutant or variant forms thereof are well known. For purposes herein, reference to luciferase refers to either the photoproteins or luciferases.

Thus, reference, for example, to *Renilla* luciferase refers to an enzyme isolated from member of the genus *Renilla* or an equivalent molecule obtained from any other source, such as from another related copepod, or that has been prepared synthetically. It is intended to encompass *Renilla* luciferases with conservative amino acid substitutions that do not substantially alter activity. Conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224).

As used herein, bioluminescence substrate refers to the compound that is oxidized in the presence of a luciferase and any necessary activators and generates light. These substrates are referred to as luciferins herein, are substrates that undergo oxidation in a bioluminescence reaction. These bioluminescence substrates include any luciferin or analog thereof or any synthetic compound with which a luciferase interacts to generate light. Typical substrates include those that are oxidized in the presence of a luciferase or protein in a light-generating reaction. Bioluminescence substrates, thus, include those compounds that those of skill in the art recognize as luciferins. Luciferins, for example, include firefly luciferin, Cypridina (also known as Vargula) luciferin (coelenterazine), bacterial luciferin, as well as synthetic analogs of these substrates or other compounds that are oxidized in the presence of a luciferase in a reaction the produces bioluminescence.

As used herein, capable of conversion into a bioluminescence substrate refers to being susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide ($FMNH_2$) by a flavin reductase enzyme. The reduced flavin mononucleotide (substrate) then reacts with oxygen (an activator) and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, a bioluminescence generating system refers to the set of reagents required to conduct a bioluminescent reaction. Thus, the specific luciferase, luciferin and other substrates, solvents and other reagents that can be required to complete a bioluminescent reaction form a bioluminescence system. Thus a bioluminescence generating system refers to any set of reagents that, under appropriate reaction conditions, yield bioluminescence. Appropriate reaction conditions refer to the conditions necessary for a bioluminescence reaction to occur, such as pH, salt concentrations and temperature. In general, bioluminescence systems include a bioluminescence substrate, luciferin, a luciferase, which includes enzymes luciferases and photoproteins and one or more activators. A specific bioluminescence system can be identified by reference to the specific organism from which the luciferase derives; for example, the *Renilla* bioluminescence system includes a *Renilla* luciferase, such as a luciferase isolated from *Renilla* or produced using recombinant methods or modifications of these luciferases. This system also includes the particular activators necessary to complete the bioluminescence reaction, such as oxygen and a substrate with which the luciferase reacts in the presence of the oxygen to produce light.

As used herein, a fluorescent protein (FP) refers to a protein that possesses the ability to fluoresce (i.e., to absorb energy at one wavelength and emit it at another wavelength). For example, a green fluorescent protein (GFP) refers to a polypeptide that has a peak in the emission spectrum at 510 nm or about 510 nm. A variety of FPs that emit at various wavelengths are known in the art. Exemplary FPs include, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein. Extending the spectrum of available colors of fluorescent proteins to blue, cyan, orange yellow and red variants, provides a method for multicolor tracking of fusion proteins.

As used herein, *Aequorea* GFP refers to GFPs from the genus *Aequorea* and to mutants or variants thereof. Such variants and GFPs from other species, such as *Anthozoa* reef coral, *Anemonia* sea anemone, *Renilla* sea pansy, *Galaxea* coral, *Acropora* brown coral, *Trachyphyllia* and *Pectiniidae* stony coral and other species are well known and are available and known to those of skill in the art. Exemplary GFP variants include, but are not limited to BFP, CFP, YFP and OFP. Examples of fluorescent proteins and their variants include GFP proteins, such as Emerald (Invitrogen, Carlsbad, Calif.), EGFP (Clontech, Palo Alto, Calif.), Azami-Green (MBL International, Woburn, Mass.), Kaede (MBL International, Woburn, Mass.), ZsGreenl (Clontech, Palo Alto, Calif.) and CopGFP (Evrogen/Axxora, LLC, San Diego, Calif.); CFP proteins, such as Cerulean (Rizzo, *Nat. Biotechnol.* 22(4): 445-9 (2004)), mCFP (Wang et al., *PNAS USA*.101(48): 16745-9 (2004)), AmCyanl (Clontech, Palo Alto, Calif.), MiCy (MBL International, Woburn, Mass.), and CyPet (Nguyen and Daugherty, *Nat. Biotechnol.* 23(3):355-60 (2005)); BFP proteins such as EBFP (Clontech, Palo Alto, Calif.); YFP proteins such as EYFP (Clontech, Palo Alto, Calif.), YPet (Nguyen and Daugherty, *Nat. Biotechnol.* 23(3): 355-60 (2005)), Venus (Nagai et al., *Nat. Biotechnol.* 20(1): 87-90 (2002)), ZsYellow (Clontech, Palo Alto, Calif.), and mCitrine (Wang et al., *PNAS USA.* 101(48):16745-9 (2004)); OFP proteins such as cOFP (Strategene, La Jolla, Calif.), mKO (MBL International, Woburn, Mass.), and mOrange; and others (Shaner N C, Steinbach P A, and Tsien R Y. (2005) *Nat. Methods.* 2(12):905-9).

As used herein, red fluorescent protein, or RFP, refers to the *Discosoma* RFP (DsRed) that has been isolated from the corallimorph *Discosoma* (Matz et al. (1999) *Nature Biotechnology* 17: 969-973), and red or far-red fluorescent proteins from any other species, such as *Heteractis* reef coral and *Actinia* or Entacmaea sea anemone, as well as variants thereof. RFPs include, for example, *Discosoma* variants, such as mRFP1, mCherry, tdTomato, mStrawberry, mTangerine (Wang et al. (2004) *PNAS USA.* 101(48):16745-9), DsRed2 (Clontech, Palo Alto, Calif.), and DsRed-T1 (Bevis and Glick (2002) *Nat. Biotechnol.*, 20: 83-87), *Anthomedusa* J-Red (Evrogen) and *Anemonia* AsRed2 (Clontech, Palo Alto, Calif.). Far-red fluorescent proteins include, for example, *Actinia* AQ143 (Shkrob et al. (2005) *Biochem J.* 392(Pt 3):649-54), Entacmaea eqFP611 (Wiedenmann et al. (2002) *PNAS USA.* 99(18):11646-51), *Discosoma* variants such as mPlum and mRasberry (Wang et al. (2004) *PNAS USA.* 101 (48): 16745-9), and *Heteractis* HcRed1 and t-HcRed (Clontech, Palo Alto, Calif.).

As used herein the term assessing or determining is intended to include quantitative and qualitative determination in the sense of obtaining an absolute value for the activity of a product, and also of obtaining an index, ratio, percentage, visual or other value indicative of the level of the activity. Assessment can be direct or indirect.

As used herein, activity refers to the in vivo activities of a compound or bacteria on physiological responses that result following in vivo administration thereof (or of a composition or other mixture). Activity, thus, encompasses resulting therapeutic effects and pharmaceutical activity of such compounds, compositions and mixtures. Activities can be observed in vitro and/or in vivo systems designed to test or use such activities.

As used herein, sample refers to anything that can contain an analyte for which an analyte assay is desired. The sample can be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, complex refers generally to an association between two or more species regardless of the nature of the interaction between the species (i.e., ionic, covalent, or electrostatic).

As used herein, a combination refers to any association between two or among more items.

As used herein, a composition refers to any mixture. It can be a solution, a suspension, an emulsion, liquid, powder, a paste, aqueous, non-aqueous or any combination thereof.

As used herein, a kit is a packaged combination, optionally, including instructions for use of the combination and/or other reactions and components for such use.

For clarity of disclosure, and not by way of limitation, the detailed description is divided into the subsections that follow.

B. Methods And Compositions For Detection And Therapy

Provided herein are methods of administering a non-pathogenic bacterium, such as a probiotic bacterium, that expresses an endogenous thymidine kinase to a subject and detecting sites of accumulation of the probiotic bacteria in the subject. In the methods provided, the non-pathogenic bacteria and a detectable compound that interacts with the endogenous bacterial thymidine kinase are administered to the subject, resulting in accumulation of the detectable compound within the bacterium. A signal emitted by or induced by the detectable compound is then detected, thereby detecting the site of bacterial accumulation.

Generally, the bacteria used in the methods are systemically administered to the subject and can accumulate at sites of cellular proliferation, including tumors, tumor tissues, metastases, areas of inflammation, immunoprivileged sites or tissues, wounds and/or infections. Hence, the methods can be used, for example, to detect or image sites of cellular proliferation, including tumors, tumor tissues, metastases, areas of inflammation, immunoprivileged sites or tissues, wounds and infections. By detecting the accumulation of a radiolabeled compound at sites of bacterial accumulation, the sites of cellular proliferation, including tumors, tumor tissues, metastases, areas of inflammation, immunoprivileged sites or tissues, wounds and/or infections can be detected and/or imaged. Such methods find applications in, for example, detection and diagnosis of diseases and disorders, evaluating the efficacy of a treatment or therapy for a disease or disorder, evaluating the optimal time of induction of therapeutic gene expression for a bacterial-mediated treatment or therapy for a disease or disorder, developing non-human animal models for diseases and disorders, assaying or screening compositions for potential use as therapeutic agents for the treatment of diseases and disorders and in tracking or monitoring delivery of compositions to cells and tissues, including, sites of cellular proliferation, tumors, tumor tissues, metastases, areas of inflammation, wounds and infections. In one example, the methods for determining the presence or absence of a bacterium in a subject for detection of a disease or disorder, involve monitoring a subject or patient to whom a bacterium has been administered for detection of the bacterium. Such bacteria can be monitored for detection using a number of techniques, including, but not limited to techniques capable of detecting a radiolabeled compound in a subject. Particular detection techniques that can be used in such methods can be, for example, positron emission tomography (PET) or single positron emission computed tomography (SPECT).

Typically, the detectable compound that is administered to the subject is phosphorylated by the endogenous bacterial thymidine kinase. Addition of the charged phosphate group to the compound prevents the efflux of the compound across the bacterial membrane, thus allowing accumulation of the compound within the cell. The detectable compound generally is not phosphorylated by or has low affinity for kinases expressed by cells of the subject, which results in specific accumulation of the compound at sites of bacterial accumulation and not in normal tissues. As such, the signal emitted by or induced by the detectable compound is limited to the sites of bacterial accumulation, thus increasing the specificity of the signal. Exemplary of detectable compounds for use in the methods are radiolabeled compounds. Such compounds can be detected by quantifying emissions from radioactive decay of the label. For example, detection of gamma emissions produced by gamma emitting radioisotopes or by annilation of a positron and an electron from positron decay of a radioisotope can be performed. Exemplary of such isotopes include, but are not limited to, isotopes of fluorine, carbon, nitrogen and oxygen (positron emitters) and iodine (gamma emitter). Detection of gamma emissions can be performed using appropriate detection instruments, such as positron emission tomography (PET) scanners or single positron emission computed tomography (SPECT) scanners or a gamma camera. Exemplary radiolabeled compounds are nucleoside analogs, labeled with a radioisotope (e.g., iodine or fluorine). Examples of such radiolabeled nucleoside analogs, include, but are not limited to, 2'-fluoro-2'deoxy-1-β-D-arabinofuranosyl-5-[$^{125}$I]iodouracil ([$^{125}$I]-FIAU), 2'-fluoro-2'deoxy-1-β-D-arabinofuranosyl-5-[$^{124}$I]iodo-uracil ([$^{124}$I]-FIAU), 9-[4-[$^{18}$F]fluoro-3-(hydroxymethyl)butyl]guanine ([$^{18}$F]-FHBG), 9-[(3-[$^{18}$F]fluoro-1-hydroxy-2-propoxy)methyl]guanine ([$^{18}$F]-FHPG), 2'-deoxy-2'-[$^{18}$F]fluoro-β-D-5-methyl-1-β-D-arabinofuranosyluracil ([$^{18}$F]-FMAU), 3'-deoxy-3'-[$^{18}$F]-fluorothymidine ([$^{18}$F]-FLT), 2'-[$^{18}$F]fluoro-2'deoxy-1 β-D-arabinofuranosyl-5-ethyl-uracil ([$^{18}$F]-FEAU) and 2'-deoxy-2'-[$^{18}$F]fluoro-5-iodo-1-β-D-arabinofuranosyluracil ([$^{18}$F]-FIAU).

Also provided herein are methods of treating diseases and disorders and compositions for use in such methods. Such methods can be used in combination with the diagnostic methods provided. Such diseases and disorders include, for example, proliferative conditions, neoplastic diseases, tumors, tumor tissue, cancer, metastasis, inflammation, wounds and infections. The methods include administering a non-pathogenic bacterium, such as a probiotic bacterium, to a subject or patient having, at risk of having or suspected of having a disease or disorder, such as a proliferative condition, neoplastic disease, tumor, tumor tissue, cancer, metastasis, inflammation, wounds or infection. In one example, the bacteria are administered simultaneously, sequentially or intermittently with one or more agents for the treatment of a proliferative condition, a neoplastic disease, a tumor, a tumor tissue, cancer, a metastasis, an inflammation, a wound or infection. In another example, the bacteria contain nucleic acid that encodes or provides for the production of a therapeutic composition. In one example, the bacteria express an endogenous gene useful for treatment of a disease or disorder. For example, the bacteria can express an endogenous enzyme such as a thymidine kinase, a cytosine deaminase or a purine nucleoside phosphorylase, that is useful for the conversion of a prodrug into a compound that is toxic to surrounding tumor cells within a tumor (e.g., acyclovir, penciclovir, ganciclovir, valacyclovir, zidovidine). In other examples the bacteria can express one or more heterologous genes useful for the treatment of a disease or disorder. Examples of therapeutic compositions that can be used in such methods include, but are not limited to, compositions that are deleterious to a tumor or cancer cell, antiproliferative agents, prodrug conversion enzymes, anti-inflammatory compositions, antibiotics and compositions that promote wound healing. In another example, the bacteria heterologously overproduce one or more of an iron storage, metabolism, binding or transport molecule. In a further example, such bacteria are administered to the subject together or separately with a metal-binding or metal-chelating molecule for treatment of a disease or disorder.

The bacteria and compositions of bacteria can be used in the preparation of a composition for detection, diagnosis or treatment of a disease or disorder, including, for example, proliferative conditions, neoplastic diseases, tumors, tumor tissue, cancer, metastasis, inflammation, wounds and infections. Such uses of the bacteria and compositions, which contain an amount effective for detection, diagnosis or treatment, are provided herein.

C. Bacteria For Use In The Methods

1. Non-Pathogenic

Generally, the bacteria used in the methods are attenuated or non-pathogenic. Particular microorganisms that can be used in the methods provided herein include, for example, mutual, commensal and/or probiotic strains of bacteria. For example the bacteria for use in the methods include strains of bacteria that coexist in a commensal or mutualistic relationship with a subject such as, for example, an animal, including human and non-human animals. Exemplary bacteria for use in the methods include mutual, commensal and/or probiotic strains of *Escherichia coli, Bacteroides, Eubacterium, Streptococcus, Actinomyces, Veillonella, Nesseria, Prevotella, Campylobacter, Fusobacterium, Eikenella, Porphyromonas* and Priopionibacteria. Exemplary of probiotic bacteria are *Escherichia* Nissle 1917. Other exemplary probiotic strains include, but are not limited to, *Bacillus cereus, Bacillus licheniformis, Bacillus pumilus, Bacillus clausii, Bacillus coagulans, Bacillus polyfermenticus, Brevibacillus laterosporus, Lactococcus, Lactobacillus reuteri, Lactobacillus amylovorus, Lactobacillus crispatus, Lactobacillus gallinarum, Lactobacillus gasseri, Lactobacillus johnsonii, Lactobacillus bifidum, Lactobacillus helveticus, Bifidobacterium lactis, Bifidobacterium breve, Leuconostoc mesenteroides, Enterococcus faecium, Pediococcus* and *Sporolactobacillus inulinu*.

2. Accumulation in Tumors and Other Immunoprivileged Sites

The bacteria used in the methods tend to accumulate in a certain area or areas of a subject to whom the bacteria are administered. Bacteria used in the methods of detecting and/or treating a site of proliferation of a proliferative condition (e.g., a tumor, tumor tissue, cancer, metastasis, neoplasm, neoplastic disease, site of inflammation, wound, wound tissue and infection) are capable of selectively accumulating in such sites or in immunoprivileged sites relative to other locations in a subject. Accumulation is selective in that the bacteria tend to accumulate at such sites to at least an equal and typically detectably greater extent than they accumulate at other locations in a subject. The degree of selective accumulation can be demonstrated in a number ways describe herein such as, for example, by evaluating and comparing the extent of accumulation of the bacteria in different locations in a subject after systemic, e.g., intravenous, administration of the bacteria to a subject having a site of proliferation or proliferative condition as described herein. Accordingly, detection of the bacteria provides for detection and evaluation of such sites. Furthermore, because such bacteria selectively accumulate at such sites, they can be used to specifically deliver substances and compositions to the sites, including therapeutic substances and compositions for use in treating diseases, disorders and conditions associated with proliferation sites and conditions, including, for example, tumors, cancers, neoplasms, neoplastic diseases, inflammation, wounds and other diseases, conditions and disorders as described herein. Also provided are examples of the treatment methods in which the bacteria themselves provide a therapeutic benefit in the treatment of diseases, disorders and/or conditions without providing for delivery of a separate therapeutic substance or composition.

A factor in the selective accumulation of the bacteria may be that they tend to be cleared from most of the body of the subject to whom they are administered by the activity of the subject's immune system, indicative of recognition of bacteria by the subject's immune system. However, in the environment of a proliferative site or condition (including, for example, a tumor, tumor tissue, cancer, metastasis, neoplasm, neoplastic disease, site of inflammation, wound, wound tissue and infection) the bacteria can nevertheless survive, replicate, proliferate and accumulate. Accordingly, for enhanced accumulation, the bacteria in particular examples are replication competent. The selective accumulation of such bacteria is thus not attributable to a targeting moiety, such as a heterologous protein that binds to a molecule that is particular to the targeted site in the subject, that has been incorporated into the bacteria to direct it to a particular site. Rather, in this case the selective accumulation can be viewed as a result of the conditions of the environment at the site of proliferation or of a proliferative condition. In some examples, however, the selective accumulation of bacteria at a target site can be enhanced through the incorporation of a targeting moiety into the bacteria.

3. Expression of Endogenous Proteins for Detection

The non-pathogenic bacteria for use in the methods provided express one or more endogenous gene products for use in detection. Such gene products can interact with a detectable compound. The detectable compound can be administered to a subject that has been administered the non-pathogenic bacterium for detection of the site(s) of bacterial accumulation. Exemplary of such gene products is a thymidine kinase. Non-pathogenic bacteria that express an endogenous thymidine kinase can be used to target radiolabeled compounds to the sites of bacterial accumulation where the radiolabeled compound interacts with the bacterial thymidine kinase. Use of an endogenous gene product, such as a bacterial thymidine kinase, allows quantitative measurement of bacterial accumulation at the sites of cellular proliferation, tumors, tumor tissues, metastases, areas of inflammation, immunoprivileged sites or tissues, wounds and/or infections. For example, the signal emitted by the radiolabeled compound can be measured following administration to the subject and correlated with a specific bacterial concentration at the accumulation site (e.g., see Example 4).

D. Modifications Of Bacteria For Use In The Methods

The probiotic bacteria for use in the methods provided herein can be modified from their wild-type form. Modifications can include any of a variety of changes, and typically include changes to the genome or nucleic acid molecules of the bacteria. For example, modifications of bacteria can include one or more modifications of the bacterial genome to add, delete or replace nucleic acid. Such modifications can alter one or more properties of the bacteria including, but not limited to, pathogenicity, toxicity, ability to preferentially accumulate in tumor, ability to lyse cells or cause cell death, replication competence, increased capacity to capture iron or other metals, increased capacity to transport iron, increased capacity to store iron, bind a ligand, or a combination thereof. Exemplary modifications include, but are not limited to deletion of one or more endogenous genes, addition of one or more exogenous genes, mutation of one or more endogenous gene products or alteration of gene expression or one or more endogenous genes.

The modified bacteria can be formed by standard methodologies well known in the art for modifying bacteria. Briefly, the methods include introducing into the bacteria one or more genetic modification(s), followed by screening the bacteria for properties reflective of the modification(s) or for other desired properties. Exemplary nucleic acid molecular modifications include truncations, insertions, deletions and mutations. In an exemplary modification, bacteria can be modified by truncation, insertion, deletion or mutation of one or more genes. In an exemplary insertion, an exogenous gene such as, for example, a ferritin, can be inserted into the genome of the bacterium or provided on a plasmid. In some examples, nucleic acid carrying multiple genes can be inserted into the genome of the bacterium or provided on a plasmid. For example, a bacterium can be modified to carry the lux operon for the production of bacterial luciferase and proteins for the generation of the bacterial luciferase substrate. In an exemplary modification, an endogenous gene, an exogenous gene or a combination thereof can be inserted into a plasmid which is inserted into the bacteria using any of the methods known in the art. In an exemplary deletion/mutation, a gene, such as, for example, the fur repressor consensus sequence, can be inactivated by homologous recombination techniques in combination with any of the other methods provided herein. Methods for optimizing expression genes are known in the art and include, for example, modification of copy number, promoter strength, deletion of genes that encode inhibitory proteins, or movement of essential genes to a plasmid in order to maintain the plasmid in the transformed bacteria. The modifications can be directed to any of a variety of regions of the bacterial genome or endogenous plasmids, including, but not limited to, a regulatory sequence, to a gene-encoding sequence, or to a sequence without a known role. Any of a variety of regions of bacterial genomes that are available for modification are readily known in the art for many bacteria, including the bacteria specifically listed herein.

Standard techniques in molecular biology can be used to generate the modified bacteria for use in the methods provided. Such techniques include various nucleic acid manipulation techniques, nucleic acid transfer protocols, nucleic acid amplification protocols, and other molecular biology techniques known in the art. For example, point mutations can be introduced into a gene of interest through the use of oligonucleotide mediated site-directed mutagenesis. Alternatively, homologous recombination techniques can be used to introduce a mutation or exogenous sequence into a target sequence of interest; or can be used to inactivate a target sequence of interest. Nucleic acid transfer protocols include calcium chloride transformation/transfection, transduction, electroporation, liposome mediated nucleic acid tramsfer and others. In an alternative mutagenesis protocol, point mutations in a particular gene can also be selected for using a positive selection pressure. See, e.g., *Current Protocols in Molecular Biology*, Ed. Ausubel et al John Wiley & Sons, Inc. Cambridge, Mass., 1995. Nucleic acid amplification proocols include but are not limited to the Polymerase chain reaction (PCR). Use of nucleic acid tools such as plasmids, vectors, promoters and other regulating sequences, are well known in the art for a large variety of organisms for use in bacterial expression systems. Plasmids can be created to carry genes using methods known to one skilled in the art. High copy plasmids can be used to cause over-expression of endogenous or heterologous proteins in a bacterium. Futher, a large variety of nucleic acid tools are available from many different sources including the American Type Culture Collection (ATCC), and various commercial sources. One skilled in the art will be readily able to select the appropriate tools and methods for genetic modifications of any particular bacterium according to the knowledge in the art and design choice.

1. Expression of Exogenous Genes

In some examples, the bacterium can be modified to express one or more exogenous genes. Exemplary exogenous gene products include proteins and RNA molecules. The modified bacteria can express gene products that are useful for diagnostic or therapeutic uses. Such diagnostic and therapeutic uses can be combined with any of the methods provided herein. For example, modified bacteria that express a detectable gene product or a gene product that induces a detectable signal can be used in conjunction with the methods for PET imaging of a radiolabeled compound that binds to an endogenous gene product, such as a bacterial thymidine kinase, to allow dual imaging of the accumulation site.

Exemplary exogenous gene products that can be expressed by the modified bacteria include, but are not limited to, a detectable gene product (e.g., fluorescent proteins, luminescent proteins), a gene product that induces a detectable signal (e.g. luciferases, ferritin, siderophore), a reporter protein (e.g., galactosidase, □glucuronidase or xanthineguanine phosphoribosyl-transferase), a therapeutic gene product, a protein that serves as a binding site for a ligand (e.g., receptors (e.g., transferrin receptor) or other transmembrane or membrane associated proteins), proteins useful for tumor therapy (e.g., *Pseudomonas* A endotoxin, diphtheria toxin, p53, Arf, Bax, tumor necrosis factor alfa, HSV TK, *E. coli* purine nucleoside phosphorylase and derivatives thereof, cytosine deaminases, uracil, phosphoribosyltransferase and fusions thereof (e.g. FCU1), angiostatin, endostatin, different cytokines) and many other proteins. For example, bacteria can be recombinantly engineered with a peptide inserted into a permissible site of an endogenous protein (e.g., OmpA) or can be recombinantly engineered with an exogenous receptor (e.g., the her2/neu receptor) or other transmembrane or membrane-bound protein that attracts therapeutic and/or diagnostic agents or ligands bound to therapeutic and/or diagnostic agents to the bacteria (e.g. siderophores, nanoparticles or cytotoxic agents). Additional systems for cell surface expression include, but are not limited to, lipoprotein, ice nucleation protein, Fimbrial, LamB PhoE, TolCand FliC systems.

Expression of exogenous genes can be controlled by a constitutive promoter, or by an inducible promoter. Expression can also be influenced by one or more proteins or RNA molecules expressed by the bacteria. Genes can be encoded in a bacterial chromosome or on a plasmid. Over-expression of a gene or gene product can be achieved by insertion of a gene into the bacterial chromosome under the control of a strong promoter. Plasmids can be created to carry genes using methods known to one skilled in the art. High copy plasmids can be used to cause over-expression of exogenous proteins in bacteria. Plasmids for expression of proteins include, but are not limited to ColE1, pBR322, p15A, pEMBLex2, pMAL-p2, pUC18A2 (a pUC18-derived plasmid containing the ftn gene), pUC118, pGS281, pMK4, pUNK1, pAMβ1 and pTA1060. Choice of a plasmid for expression at desired levels is well-known in the art as well as techniques to introduce genes into the plasmids (Sambrook et al. *Molecular Cloning: A Laboratory Manual.* $2^{nd}$ ed. Cold Spring Harbor Laboratory Press, New York, N.Y. 1989; *Current Protocols in Molecular Biology.* Ed. Ausubel et al. John Wiley & Sons, Inc. Cambridge, Mass., 1995).

In some examples of modifying a bacterium to express an exogenous gene, the modification can also contain one or more regulatory sequences to regulate expression of the exogenous gene. As is known in the art, regulatory sequences can permit constitutive expression of the exogenous gene or can permit inducible expression of the exogenous gene. Further, the regulatory sequence can permit control of the level of expression of the exogenous gene. In some examples, inducible expression can be under the control of cellular or other factors present in a tumor cell, present in a bacterially-infected tumor cell, or present in/on extracellular bacteria localized in a tumor environment. In other examples, inducible expression can be under the control of an administrable substance, including sugars such as arabinose, xylose, IPTG, RU486 or other known induction compounds. Any of a variety of regulatory sequences are available to one skilled in the art according to known factors and design preferences. In some examples, the regulatory sequence can result in constitutive, high levels of gene expression. In tumor therapy examples, a therapeutic protein can be under the control of an internally inducible promoter or an externally inducible promoter. In some examples, the inducible promoter is a sugar-inducible promoter, such as an arabinose- or xylose-inducible promoter. Recombinant bacteria that contain a sugar-inducible promoter for the expression of exogenous genes can be modified to decrease or abolish the metabolic breakdown of the inducing sugar. For example, bacteria, such as *E. coli*, can be modified such that the breakdown and/or utilization of arabinose in the bacteria is reduced or abolished, which allows for greater accumulation of arabinose in the cells leading to higher gene induction of and longer gene expression from arabinose-inducible promoters in the recombinant bacteria. In one example of the methods provided, inducible promoters can be used to initiate expression of a gene product once the bacteria have accumulated to a particular concentration at the accumulation. The diagnostic methods provided allow quantitative measurement of bacterial accumulation at the accumulation site and can be used to optimize the induction of gene products for therapy.

2. Inactivation of Genes

Methods to inactivate genes on a bacterial chromosome are known to one skilled in the art. Bacterial genes can be inactivated by replacing the chromosomal genes with disrupted derivatives containing antibiotic resistance cassettes or non-sense sequences in place of some or all of the corresponding coding regions. More than one gene can be inactivated (e.g., "knocked out") by these methods (Abdul-Tehrani et al. (1999) *J. Bacteriol.* 181(5): 1415-1428; Chen and Morse (1999) *Microbiology* 145: 2967-2975; Waidner et al. (2002) *Infec. Immun.* 70(7): 3923-3929). PCR analysis can be used to detect the resistance marker and confirm the mutagenesis (Beresswill et al. (1998) *Microbiology.* 144 (Pt 9): 2505-2516). Conditional inactivation of bacterial genes using phage-based *E. coli* homologous recombination systems has been developed making it possible to subclone or modify DNA cloned into plasmids, BACs, or PACs without using restriction enzymes or DNA ligases (Liu et al. (2003) *Genome Res.* 13(3): 476-484). Exemplary modifications to bacteria include, but are not limited to, inactivation of consensus sequences such as the 19-base pair DNA consensus sequence binding region of the Fur protein (5'-GATAATGATAATCAT-TATC-3'; SEQ ID NO: 2) that is found in the promoter region of many genes that are negatively regulated by iron, or inactivation of the msbB gene, which encodes a lipid acyl A transferase, that results in decreased virulence of the bacteria due to the synthesis of lipopolysaccharide (LPS) that lacks the myristic acid moiety of lipid A (Jung et al. (1998) *Enzyme Microb Technol.* 22(5):348-54 and U.S. Patent Application Publication No. 2005-0255088).

In some examples, the bacteria for use in the methods provided herein contain extrachromosomal plasmids that can be modified and/or removed. For example, *E. coli* Nissle 1917, contains two extrachromosomal plasmids, pMUT1 and pMUT2. Exemplary Nissle 1917 bacteria for use in the methods include Nissle 1917 that are modified to remove one or both of pMUT1 and pMUT2 (e.g., methods of curing bacteria of extrachromosomal plasmids are described, for example, in Altenhoefer et al. (2004) *FEMS Immunology and Medical Microbiology* 20:223-229).

E. Imaging

Provided herein are methods of detecting and/or imaging sites of cellular proliferation, tumors, tumor tissues, metastases, areas of inflammation, immunoprivileged sites or tissues, wounds and infections, using a radiolabeled compound that interacts with an endogenously expressed gene product. Accordingly, any method known in the art for detecting such compounds in a subject can be employed for detecting and/or imaging the sites of accumulation of the compound in a subject. In a particular example, the compounds used for detection and/or imaging are metabolic compounds (e.g., nucleoside analogs). The metabolic compounds can be labeled with an isotope, such as a gamma emitter or a positron emitter, which produces gamma emissions upon decay. Such radiolabeled compounds can be detected in vivo by a variety of methods, including, for example, planar gamma imaging, positron emission tomography (PET) or single positron emission computed tomography (SPECT).

In an exemplary imaging method, non-pathogenic bacteria that express an endogenous thymidine kinase and a radiolabeled metabolic compound that binds to the thymidine kinase are administered, simultaneously, sequentially or intermittently, to a subject. The bacteria localize to sites of cellular proliferation, tumors, tumor tissues, metastases, areas of inflammation, immunoprivileged sites or tissues, wounds or infections, and the radiolabeled compound is taken up by the bacteria in vivo. The radiolabeled compound is then imaged externally to the subject thereby indicating the sites of bacterial accumulation and thereby detecting the sites of cellular proliferation, tumors, tumor tissues, metastases, areas of inflammation, immunoprivileged sites or tissues, wounds or infections. In a particular example, a tumor or metastasis is imaged.

In some examples, the amount of signal emitted in vivo by the administered radiolabeled compound is quantitatively measured. In such examples, the amount of signal emitted by the radiolabeled compound that has accumulated at a particular site in vivo can be measured. For the methods provided herein, the radiolabeled compound typically accumulates within bacteria that are administered to the subject. Thus, the radiolabeled compound accumulates at sites of bacterial accumulation, including, for example, sites of cellular proliferation, such as tumors, tumor tissues, metastases, areas of inflammation, immunoprivileged sites or tissues, wounds or infections. The amount of signal emitted by the radiolabeled compound in vivo can be correlated with a particular amount of bacteria. In some examples, the amount is an estimate of the concentration of bacteria at the accumulation site. In other examples, the amount is a relative amount, such as the relative amount of bacteria accumulated at the site of proliferation (e.g., tumor or metastasis) compared to a normal tissue. Thus, the magnitude of the signal emitted by the accumulated radiolabeled compound can be employed to indicate the quantity of bacteria that has accumulated at the proliferation site. Such information can be used, for example, to measure tumor size and to monitor the effects of administration of one or more therapeutic agents on tumor size, such as monitoring tumor growth inhibition and/or tumor shrinkage over time. In examples where the radiolabeled compound has a relatively short half-life, administration of the radiolabeled compound can be repeated to obtain an image for each time point that is monitored.

In some examples, the bacteria can express one or more therapeutic agents under the control of an inducible promoter. In such examples, the amount of signal emitted by the radiolabeled compound in vivo can be correlated with an amount of bacteria, and can be used to determine the optimal time to induce expression of the therapeutic agent by the bacteria. For example, the amount of bacteria that have accumulated at a site of proliferation (e.g., tumor or metastasis) can be monitored over time. Once the bacteria have reached a particular concentration at the desired site, an inducer molecule can be administered to the subject to induce expression of the therapeutic agent.

In some examples, the bacteria can express one or more gene products that can bind to a therapeutic agent or a ligand conjugated to a therapeutic agent. In such examples, the amount of signal emitted by the radiolabeled compound in vivo can be correlated with an amount of bacteria, and can be used to determine the optimal time to administer the therapeutic agent or ligand-therapeutic agent conjugate. For example, the amount of bacteria that have accumulated at a site of proliferation (e.g., tumor or metastasis) can be monitored over time. Once the bacteria have reached a particular concentration at the desired site, the therapeutic agent or ligand-therapeutic agent conjugate can be administered. In some examples, the expression of a gene product that can bind to a therapeutic agent or a ligand can be under the control of an inducible promoter, and an inducer molecule can be administered at the desired time to induce expression of the gene product.

Also provided are methods of imaging accumulation of bacteria in a subject, using two or more imaging methods (e.g., dual imaging). For example, bacteria can be imaged by two or more methods simultaneously or sequentially. Bacteria can be detected, imaged and/or monitored by any of a variety of methods known in the art. Exemplary detection, imaging and/or monitoring methods include any of a variety magnetic resonance methods such as magnetic resonance imaging (MRI) and magnetic resonance spectroscopy (MRS), other tomographic methods, including computed tomography (CT), computed axial tomography (CAT), electron beam computed tomography (EBCT), high resolution computed tomography (HRCT), hypocycloidal tomography, spiral computed tomography and ultrasonic tomography. Other exemplary imaging methods include low-light imaging, X-rays, ultrasound signal, fluorescence and absorption.

In an exemplary dual-imaging method, non-pathogenic bacteria that express an endogenous thymidine kinase and an exogenous detectable gene product or a gene product that induces a detectable signal are administered to a subject. Accumulation of such bacteria in the subject can be imaged by detecting the accumulation of a radiolabeled compound in the bacteria as described herein and can also be imaged by detection of the detectable gene product or a gene product that induces a detectable signal using the appropriate detection method. In one non-limiting example, expression of an iron transport protein or a protein that induces bacterial accumulation of iron can be employed to image the bacteria by magnetic resonance imaging (MRI).

In another exemplary dual-imaging method, a tumor is imaged using gamma imaging or positron emission tomography and another tomographic method, such as, but not limited to, computed tomography (CT), computed axial tomography (CAT), electron beam computed tomography (EBCT), high resolution computed tomography (HRCT), hypocycloidal tomography, spiral computed tomography or ultrasonic tomography. In such methods, non-pathogenic bacteria that express an endogenous thymidine kinase and a radiolabeled metabolic compound that binds to the thymidine kinase are administered, simultaneously, sequentially or intermittently, to a subject. The bacteria localize to sites of the tumor or metastasis, and the radiolabeled compound is taken up by the bacteria in vivo. The radiolabeled compound is then imaged externally to the subject thereby indicating the sites of the tumor or metastasis. The tumor can also be imaged by a tomographic image to confirm or refine the image of the tumor or metastasis in the subject.

1. Administration for Detection, Imaging and/or Monitoring Treatment

For methods of detecting or imaging sites of cellular proliferation, tumors, tumor tissues, metastases, areas of inflammation, immunoprivileged sites or tissues, wounds and infections, any mode of administration of bacteria to a subject can be used, provided the mode of administration permits the bacteria to accumulate at sites of cellular proliferation, tumors, tumor tissues, metastases, areas of inflammation, immunoprivileged sites or tissues, wounds and infections. Typically, for methods of detection where the site of cellular proliferation, tumor, tumor tissue, metastasis, area of inflammation, immunoprivileged site or tissue, wound or infections is unknown, the bacteria and/or the radiolabeled compound are administered systemically. For methods of monitoring a therapeutic treatment where the such sites is known, systemic or localized administration of the bacteria and/or the radiolabeled compound can be selected.

For monitoring a tumor therapy, any mode of administration of bacteria to a subject can be used, provided the mode of administration permits the bacteria to accumulate in the tumor or metastasis. Modes of administration can include, but are not limited to, subcutaneous, intravenous, intraperitoneal, intramuscular, topical, intratumoral, inhalation, intranasal, oral, intracavity (e.g., administering to the bladder via a catheter, administering to the gut by suppository or enema), aural, ocular, transdermal, subcutaneous, intra-arterial (e.g. hepatic artery infusion), intravesicular perfusion, or intrapleural administration. One skilled in the art can select any mode of administration compatible with the subject and the bacteria, and that also is likely to result in the bacteria reaching tumors and/or metastases. The route of administration can be selected by one skilled in the art according to any of a variety of factors, including the nature of the disease, the kind of tumor, and the particular bacteria contained in the pharmaceutical composition. Administration to the target site can be performed, for example, by ballistic delivery, as a colloidal dispersion system, or systemic administration can be performed by injection into an artery, such as the hepatic artery.

2. Dosages for Detection, Imaging and/or Monitoring Treatment

The dosage regimen can be any of a variety of methods and amounts, and can be determined by one skilled in the art according to known clinical factors. Dosages for detection, imaging and/or monitoring of a therapeutic treatment can be determined empirically by the amount needed to produce a detectable signal. As is known in the medical arts, dosages for any one patient can depend on many factors, including the subject's species, size, body surface area, age, sex, immunocompetence, and general health, the particular bacteria to be administered, duration and route of administration, the kind and stage of the disease, for example, tumor size, and other compounds such as drugs being administered concurrently. Exemplary routes of administration, such as topical, local, or systemic administration can differ in the dosage given. For example, dosages for injections intravenously, intraperitoneally, or intratumorally can differ. Thus, dosages delivered directly into a tumor (i.e. intratumoral injection) can be administered at lower effective dosages. In addition to the above factors, such levels can be affected by the infectivity of the bacteria, and the nature of the bacteria, as can be determined by one skilled in the art. In the present methods, appropriate minimum dosage levels of bacteria can be levels sufficient for the bacteria to survive, grow and replicate in a tumor or metastasis. Appropriate maximum dosage levels of bacteria can be levels that are not toxic to the host, levels that do not cause splenomegaly of 3× or more, levels that do not result in colonies in normal tissues or organs after about 1 day or after about 3 days or after about 7 days. Exemplary levels for administering a bacterium to a 65 kg human can include $1\times10^3$ or about $1\times10^3$ cfu colony forming units (cfu), $1\times10^4$ or about $1\times10^4$ cfu, $1\times10^5$ or about $1\times10^5$ cfu, $1\times10^6$ or about $1\times10^6$ cfu, $1\times10^7$ or about $1\times10^7$ cfu, $5\times10^7$ or about $5\times10^7$ cfu, $1\times10^8$ or about $1\times10^8$ cfu, $1\times10^9$ or about $1\times10^9$ cfu, $1\times10^{10}$ or about $1\times10^{10}$ cfu, $5\times10^{10}$ or about $5\times10^{10}$ cfu, $1\times10^{11}$ or about $1\times10^{11}$ cfu, $5\times10^{11}$ or about $5\times10^{11}$ cfu, or more cfu.

A suitable dosage range for administration of a nucleoside analog for detection in a human is less than 50.0 mg/kg/day. Typically, the dosage range of the nucleoside analog is from 0.05 or about 0.05 mg/kg/day to 30.0 or about 30.0 mg/kg/day. For a 70 kg adult, for example, the dosage range typically ranges from about or 3.5 mg to about or 2100 mg. In some examples the dosage of the nucleoside analog is about or 0.05 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg 15 mg/kg, 20 mg/kg or 30 mg/kg per day. In some examples, dosage formulations and combinations containing the nucleoside analog for administration can contain about or 1 mg, about or 10 mg, about or 50 mg, about or 100 mg, about or 200 mg, about or 300 mg, about or 400 mg, about or 500 mg, about or 600 mg, about or 700 mg, about or 800 mg, about or 900 mg, about or 1000 mg, about or 1500 mg, about or 2000 mg, about or 2500 mg or more of the nucleoside analog. Suitable doses for the halogenated pyrimidines in general, are less than for FEAU because of their greater toxicity. For detection, specific activities of radiolabel nucleoside analogs typically range from about or 0.1 Ci/umol to 100 Ci/umol.

f. Therapy

The diagnostic methods provided herein can be employed in conjunction with therapeutic methods, including methods of treating, delaying progression of immunoprivileged cells or tissue, or preventing immunoprivileged cells or tissue, including cancerous cells, tumors and metastases. The therapeutic methods include administering bacteria to a subject containing one or more tumor(s) and/or metastases. The bacteria can be administered to kill tumor cells, decrease the tumor size, or prevent or delay expansion of the tumor. The therapeutic methods also include administering bacteria to a subject containing one or more tumor(s) and/or metastases and utilizing the bacteria to monitor a therapeutic treatment, such as administration of one or more therapeutic agents or expression of one or more therapeutic agents by the bacteria or a combination thereof.

Tumors that can be treated using the methods provided herein include, but are not limited to, bladder tumors, breast tumors, prostate tumors, glioma tumors, adenocarcinomas, ovarian carcinomas, and pancreatic carcinomas, liver tumors and skin tumors. In one example, the human malignancy treated is a cancer such as, but not limited to, pancreatic cancer, non-small cell lung cancer, multiple myeloma, or leukemia. In addition, other metastatic diseases can be treated by the methods provided herein. Cancers can also be cancer-forming solid tumors, such as lung and bronchus, breast, colon and rectum, kidney, stomach, esophagus, liver and intrahepatic bile duct, urinary bladder, brain and other nervous system, head and neck, oral cavity and pharynx, cervix, uterine corpus, thyroid, ovary, testes, prostate, malignant melanoma, cholangiocarcinoma, thymoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

The administered bacteria for use in the diagnostic and therapeutic methods provided herein typically express an endogenous gene product (e.g., an endogenous thymidine kinase) that interacts with a detectable compound for use in imaging. In addition, the administered bacteria for use in the diagnostic and therapeutic methods provided herein can posses one or more characteristics including, but not limited to, attenuated pathogenicity, low toxicity, preferential accumulation in tumors, increased ability to capture, transport and or store iron, immunogenicity, an ability to express or over-express exogenous genes, an ability to over-express endogenous genes and an ability to bind ligands. The bacteria can be administered to a subject without causing disease in the subject.

In some examples, the bacteria can accumulate at a site of proliferation that is a tumor or metastases. In some examples, the bacteria can elicit an anti-tumor response in the subject, where typically the bacteria-mediated anti-tumor response can develop over several days, such a week or more, 10 days or more, two weeks or more, or a month or more. In some exemplary methods, the bacteria can be present in the tumor, and can cause an anti-tumor response without the bacteria itself causing tumor cell death. An anti-tumor response induced as a result of tumor or metastases-accumulated bacteria can result in inhibition of tumor growth, shrinkage, and/or elimination of the tumor.

Therapeutic methods for delaying or inhibiting growth or formation of a tumor and/or metastasis in a subject, decreasing the size of a tumor and/or metastasis in a subject, and/or eliminating a tumor and/or metastasis from a subject, include administering the bacteria to a subject where the bacteria accumulates in a tumor and/or metastasis and causes or enhances an anti-tumor response. The anti-tumor response induced as a result of tumor or metastasis-accumulated bacteria can result in inhibition of metastasis growth or formation, decrease in the size of the tumor and/or metastasis and/or elimination of the tumor and/or metastasis from the subject.

Therapeutic methods of reducing inhibiting tumor growth, inhibiting metastasis growth and/or formation, decreasing the size of a tumor or metastasis, eliminating a tumor or metastasis, or other tumor therapeutic methods can include causing or enhancing an anti-tumor response in the host, depleting a vital nutrient (e.g., iron) from the tumor environment or delivering a therapeutic agent to the tumor. The response of the host, being anti-tumor in nature, can be mounted against tumors and/or metastases in which bacteria have accumulated and also can be mounted against tumors and/or metastases in which the bacteria have not accumulated, including tumors and/or metastases that form after administration of the bacteria to the subject. Accordingly, a tumor and/or metastasis whose growth or formation is inhibited, or whose size is decreased, or that is eliminated, can be a tumor and/or metastasis in which the bacteria have accumulated, or also can be a tumor and/or metastasis in which the bacteria or cells have not accumulated, including tumors and/or metastases that form after administration of the bacteria to the subject. Accordingly, therapeutic methods of reducing inhibiting tumor growth, inhibiting metastasis growth and/or formation, decreasing the size of a tumor or metastasis, eliminating a tumor or metastasis or other tumor therapeutic methods can include a method administering to a subject bacteria, where the bacteria accumulates in at least one tumor or metastasis and causes or enhances an anti-tumor response in the subject, and the response also is mounted against a tumor and/or metastasis in which the bacteria did not accumulate. In another example, therapeutic methods for inhibiting or preventing recurrence of a neoplastic disease or inhibiting or preventing new tumor growth include methods of administering to a subject a bacterium that can accumulate in a tumor and/or metastasis, and can cause or enhance an anti-tumor response, and the anti-tumor response can inhibit or prevent recurrence of a neoplastic disease or inhibit or prevent new tumor growth.

Therapeutic methods, such as methods of reducing inhibiting tumor growth, inhibiting metastasis growth and/or formation, decreasing the size of a tumor or metastasis, eliminating a tumor or metastasis, or other tumor therapeutic methods, can include administering to a subject a bacteria that can cause tumor cell lysis or tumor cell death, that can bind a ligand that causes tumor cell lysis or tumor cell death or deplete a vital nutrient from the tumor environment. The anti-tumor immune response induced as a result of lysed tumor components can result in, or enhance, inhibition of tumor growth, shrinkage, and/or elimination of the tumor. Such bacteria can be the same bacteria as the bacteria that can cause or enhance an anti-tumor response in the subject. Bacteria, such as the bacteria used in the methods provided herein, can cause cell lysis or tumor cell death. Additionally, the bacteria used in the methods provided herein, can cause cell lysis or tumor cell death, for example, as a result of expression of iron sequestration or binding of a compound that sequesters iron or carries a therapeutic agent (e.g., expression of a toxin, enzyme or other therapeutic gene product).

The bacteria for use in the diagnostic methods provided herein can be used to image or monitor the therapeutic efficacy of the therapeutic methods, such as reducing inhibiting tumor growth, inhibiting metastasis growth and/or formation, decreasing the size of a tumor or metastasis, eliminating a tumor or metastasis, or other tumor therapeutic methods. In some examples, the bacteria that are used to image or monitor the tumor or metastasis can be the same bacteria that are administered to cause lysis or tumor cell death can be the same. In other examples, the bacteria that are used to image or monitor the tumor or metastasis can be a different from the bacteria that are administered to cause lysis or tumor cell death (i.e., two or more strains of bacteria can be administered for imaging and/or therapeutic purposes).

Bacteria used in the anti-tumor therapies can be modified using any of the techniques described herein. Modified bacteria exhibit one or more enhanced characteristics relative to the wild-type bacteria. Such characteristics can include, but are not limited to, attenuated pathogenicity, decreased or increased toxicity, preferential accumulation in tumor, increased of increased ability to capture, transport or store iron, increased or decreased replication competence, enhanced or reduced capacity to express endogenous polypeptides, ability to express exogenous proteins, ability to induce expression of target genes with an exogenous signal, and combinations thereof. In other examples, the bacteria can be further modified to express one or more detectable gene products, including gene products that can be used for imaging. Such bacteria can be used in combination with the imaging methods provided herein. For example, bacteria can be imaged by two methods simultaneously or sequentially using the expressed detectable gene product for one imaging method and the radiolabeled compound that binds to an endogenous gene product for another imaging method.

The tumor-colonizing capability of a variety of bacteria can be directly measured by injecting bacteria into appropriate tumor-bearing animal models and the tumors assessed for colonization. Additionally, specificity of the bacteria to localize to the tumors compared to non-tumorous tissues can be measured.

1. Administration In performing the methods provided herein, bacteria can be administered to a subject, including a subject having a site of cellular proliferation or a proliferative condition, including tumors, tumor tissues, metastases, areas of inflammation, immunoprivileged sites or tissues, wounds and/or infections. In a particular example, the bacteria are administered to a subject with a tumor or a metastasis.

a. Steps Prior to Administering the Bacteria

In some examples, one or more steps can be performed prior to administration of the bacteria to the subject. Any of a variety of preceding steps can be performed, including, but not limited to, diagnosing the subject with a condition appropriate for bacterial administration, determining the immunocompetence of the subject, immunizing the subject, treating the subject with a chemotherapeutic agent, treating the subject with radiation, or surgically treating the subject.

For examples that include administering bacteria to a tumor-bearing subject for therapeutic purposes, the subject has typically been previously diagnosed with a neoplastic condition. Diagnostic methods also can include determining the type of neoplastic condition, determining the stage of the neoplastic conditions, determining the size of one or more tumors in the subject, determining the presence or absence of metastatic or neoplastic cells in the lymph nodes of the subject, or determining the presence of metastases of the subject. Some examples of therapeutic methods for administering bacteria to a subject can include a step of determination of the size of the primary tumor or the stage of the neoplastic disease, and if the size of the primary tumor is equal to or above a threshold volume, or if the stage of the neoplastic disease is at or above a threshold stage, bacteria is administered to the subject. In a similar example, if the size of the primary tumor is below a threshold volume, or if the stage of the neoplastic disease is at or below a threshold stage, the bacteria is not yet administered to the subject; such methods can include monitoring the subject until the tumor size or neoplastic disease stage reaches a threshold amount, and then administering the bacteria to the subject. Threshold sizes can vary according to several factors, including rate of growth of the tumor, ability of the bacteria to infect a tumor, and immunocompetence of the subject. Generally the threshold size will be a size sufficient for bacteria to accumulate and replicate in or near the tumor without being completely removed by the host's immune system, and will typically also be a size sufficient to sustain a bacterial infection for a time long enough for the host to mount an immune response against the tumor cells, typically about one week or more, about ten days or more, or about two weeks or more. Threshold neoplastic disease stages also can vary according to several factors, including specific requirement for staging a particular neoplastic disease, aggressiveness of growth of the neoplastic disease, ability of the bacteria to infect a tumor or metastasis, and immunocompetence of the subject. Generally the threshold stage will be a stage sufficient for bacteria to accumulate and replicate in a tumor or metastasis without being completely removed by the host's immune system, and will typically also be a size sufficient to sustain a bacterial infection for a time long enough for the host to mount an immune response against the neoplastic cells, typically about one week or more, about ten days or more, or about two weeks or more. Exemplary threshold stages are any stage beyond the lowest stage (e.g., Stage I or equivalent), or any stage where the primary tumor is larger than a threshold size, or any stage where metastatic cells are detected.

In another example, the subject can have administered thereto bacteria without any previous steps of cancer treatment such as chemotherapy, radiation therapy or surgical removal of a tumor and/or metastases. The methods provided herein take advantage of the ability of the bacteria to enter or localize near a tumor, where the tumor cells can be protected from the subject's immune system; the bacteria can then proliferate in such an immunoprotected region and can deplete the tumor of iron, or bind a ligand conjugated to a therapeutic agent. Provided herein are methods of treating a tumor, metastases or neoplastic disease in which bacteria are administered to a subject with a tumor or neoplastic disease without removing the primary tumor, or to a subject with a tumor or neoplastic disease in which at least some tumors or neoplastic cells are intentionally permitted to remain in the subject.

In some cancer treatment methods, such as chemotherapy or radiation therapy, such methods typically have a side effect of weakening the subject's immune system. This treatment of a subject by chemotherapy or radiation therapy can reduce the subject's ability to mount an anti-tumor immune response. Thus, for example, provided herein are methods of treating a tumor or neoplastic disease in which bacteria are administered to a subject with a tumor or neoplastic disease without treating the subject with an immune system-weakening therapy, such as chemotherapy or radiation therapy.

In an alternative example, prior to administration of bacteria to the subject, the subject can be treated in one or more cancer treatment steps that do not remove the primary tumor or that do not weaken the immune system of the subject. A variety of more sophisticated cancer treatment methods are being developed in which the tumor can be treated without surgical removal or immune-system weakening therapy. Exemplary methods include administering a compound that decreases the rate of proliferation of the tumor or neoplastic cells without weakening the immune system (e.g., by administering tumor suppressor compounds or by administering tumor cell-specific compounds) or administering an angiogenesis-inhibiting compound. Thus, combined methods that include administering bacteria to a subject can further improve cancer therapy. Thus, provided herein are methods of administering bacteria to a subject, along with prior to or subsequent to, for example, administering a compound that slows tumor growth without weakening the subject's immune system or a compound that inhibits vascularization of the tumor.

b. Mode of Administration Any mode of administration of bacteria to a subject can be used, provided the mode of administration permits the bacteria to enter a tumor or metastasis. Modes of administration can include, but are not limited to, intravenous, intraperitoneal, subcutaneous, intramuscular, topical, intratumoral, inhalation, intranasal, oral, intracavity (e.g., administering to the bladder via a catheter, administering to the gut by suppository or enema), aural, ocular, transdermal, subcutaneous, intra-arterial (e.g. hepatic artery infusion), intravesicular perfusion, or intrapleural administration. One skilled in the art can select any mode of administration compatible with the subject and the bacteria, and that also is likely to result in the bacteria reaching tumors and/or metastases. The route of administration can be selected by one skilled in the art according to any of a variety of factors, including the nature of the disease, the kind of tumor, and the particular bacteria contained in the pharmaceutical composition. Administration to the target site can be performed, for example, by ballistic delivery, as a colloidal dispersion system, or systemic administration can be performed by injection into an artery, such as the hepatic artery.

c. Dosage

The dosage regimen can be any of a variety of methods and amounts, and can be determined by one skilled in the art according to known clinical factors. Dosages can be determined empirically by the amount needed to produce a detectable signal or amount to effect a physiological response. As is known in the medical arts, dosages for any one patient can depend on many factors, including the subject's species, size, body surface area, age, sex, immunocompetence, and general health, the particular bacteria to be administered, duration and route of administration, the kind and stage of the disease, for example, tumor size, and other compounds such as drugs being administered concurrently. Exemplary routes of administration, such as topical, local, or systemic administration can differ in the dosage given. For example, dosages for injections intravenously, intraperitoneally, or intratumorally can differ. Thus, dosages delivered directly into a tumor (i.e. intratumoral injection) can be administered at lower effective dosages. In addition to the above factors, such levels can be affected by the infectivity of the bacteria, and the nature of the bacteria, as can be determined by one skilled in the art. In the present methods, appropriate minimum dosage levels of bacteria can be levels sufficient for the bacteria to survive, grow and replicate in a tumor or metastasis. Appropriate maximum dosage levels of bacteria can be levels that are not toxic to the host, levels that do not cause splenomegaly of 3× or more, levels that do not result in colonies in normal tissues or organs after about 1 day or after about 3 days or after about 7 days. Exemplary levels for administering a bacterium to a 65 kg human can include $1\times10^3$ or about $1\times10^3$ cfu colony forming units (cfu), $1\times10^4$ or about $1\times10^4$ cfu, $1\times10^5$ or about $1\times10^5$ cfu, $1\times10^6$ or about $1\times10^6$ cfu, $1\times10^7$ or about $1\times10^7$ cfu, $5\times10^7$ or about $5\times10^7$ cfu, $1\times10^8$ or about $1\times10^8$ cfu, $1\times10^9$ or about $1\times10^9$ cfu, $1\times10^{10}$ or about $1\times10^{10}$ cfu, $5\times10^{10}$ or about $5\times10^{10}$ cfu, $1\times10^{11}$ or about $1\times10^{11}$ cfu, $5\times10^{11}$ or about $5\times10^{11}$ cfu, or more cfu. Dosages injected intratumorally can be lower, for example, 100 cfu or more.

d. Number of Administrations

The methods provided herein can include a single administration of bacteria to a subject or multiple administrations of bacteria to a subject. In some examples, a single administration is sufficient to establish growth of bacteria in a tumor, where the bacteria can proliferate and can cause or enhance an anti-tumor response in the subject; such methods do not require additional administrations of bacteria in order to cause or enhance an anti-tumor response in a subject, which can result, for example in inhibition of tumor growth, inhibition of metastasis growth or formation, reduction in tumor or metastasis size, elimination of a tumor or metastasis, inhibition or prevention of recurrence of a neoplastic disease or new tumor formation, or other cancer therapeutic effects. In other examples, bacteria can be administered on different occasions, separated in time, typically, by at least one day. Separate administrations can increase the locations on a tumor or metastasis where the bacterial proliferation can occur or can otherwise increase the titer of bacteria accumulated in the tumor, and also can, optionally, increase the level of tumor cell death. Separate administrations of bacteria can further extend a subject's immune response against bacterial antigens, which can extend the host's immune response to tumors or metastases in which bacteria have accumulated, and can increase the likelihood a host mounting an anti-tumor immune response.

When separate administrations are performed, each administration can be a dosage amount that is the same or different relative to other administration dosage amounts. In one example, all administration dosage amounts are the same. In other examples, a first dosage amount can be a larger dosage amounts than one or more subsequent dosage amounts, for example, at least 10× larger, at least 100× larger, or at least 1000× larger than subsequent dosage amounts. In one example of a method of separate administrations in which the first dosage amount is greater than one or more subsequent dosage amounts, all subsequent dosage amounts can be the same, smaller amount relative to the first administration.

Separate administrations can include any number of two or more administrations, including two, three, four, five or six administrations. One skilled in the art can readily determine the number of administrations to perform or the desirability of performing one or more additional administrations according to methods known in the art for monitoring therapeutic methods and other monitoring methods provided herein. Accordingly, the methods provided herein include methods of providing to the subject one or more administrations of bacteria, where the number of administrations can be determined by monitoring the subject, and, based on the results of the monitoring, determining whether or not to provide one or more additional administrations. Deciding of whether or not to provide one or more additional administrations can be based on a variety of monitoring results, including, but not limited to, indication of tumor growth or inhibition of tumor growth, appearance of new metastases or inhibition of metastasis, the subject's anti-bacteria antibody titer, the subject's anti-tumor antibody titer, the overall health of the subject, the weight of the subject, the presence of bacteria solely in tumor and/or metastases or the presence of bacteria in normal tissues or organs.

The time period between administrations can be any of a variety of time periods. The time period between administrations can be a function of any of a variety of factors, including monitoring steps, as described in relation to the number of administrations, the time period for a subject to mount an immune response, the time period for a subject to clear bacteria from normal tissue, or the time period for bacterial proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear bacteria from normal tissue; for example, the time period can be more than the time period for a subject to clear bacteria from normal tissue, such as more than about a day, more than about two days, more than about three days, more than about five days, or more than about a week. In another example, the time period can be a function of the time period for bacterial proliferation in the tumor or metastasis; for example, the time period can be more than the amount of time for a detectable signal to arise in a tumor or metastasis after administration of bacteria expressing a detectable marker, such as about 3 days, about 5 days, about a week, about ten days, about two weeks, or about a month.

2. Co-Administrations

Also provided are methods in which an additional therapeutic substance, such as a different therapeutic microorganism or cell or a therapeutic compound is administered. In some examples, the additional therapeutic substance is, for example, a siderophore, an antibody, a peptide, a protein (e.g., lactoferrin or transferrin), a molecule for induction of gene expression (e.g., arabinose), a nanoparticle, another therapeutic microorganism or cell or any other compound provided herein that can be administered as a therapeutic composition. These can be administered simultaneously, sequentially or intermittently with the first microorganism. The additional therapeutic substance can interact with the microorganism or a gene product thereof, or the additional therapeutic substance can act independently of the microorganism. Any mode of administration of a microorganism to a subject can be used, provided the mode of administration permits the microorganism to enter a tumor or metastasis.

Modes of administration for a co-administered substance can be the same mode of administration as the microorganism or can be via a different mode of administration. Modes of administration can include, but are not limited to, intravenous, intraperitoneal, subcutaneous, intramuscular, topical, intratumor, inhalation, intranasal, oral, intracavity (e.g., administering to the bladder via a catheter, administering to the gut by suppository or enema), aural, ocular, transdermal, subcutaneous, intra-arterial (e.g. hepatic artery infusion), intravesicular perfusion, or intrapleural administration. One skilled in the art can select any mode of administration compatible with the subject and the microorganism or cell, and that also is likely to result in the co-administered substance reaching the microorganism or cell or tumors and/or metastases. The route of administration can be selected by one skilled in the art according to any of a variety of factors, including the nature of the disease, the kind of tumor, and the particular microorganism or cell contained in the pharmaceutical composition. Administration to the target site can be performed, for example, by ballistic delivery, as a colloidal dispersion system, or systemic administration can be performed by injection into an artery, such as the hepatic artery. In one non-limiting example provided herein a co-administered molecule, such as arabinose for the induction of gene expression, is administered by intravenous injection or provided orally.

a. Other Therapeutic Agents, Compounds and Gene Products

The methods can include administering one or more therapeutic compounds to the subject in addition to administering a microorganism or plurality thereof to a subject. Therapeutic compounds can act independently, or in conjunction with the microorganism, for tumor therapeutic affects. Therapeutic compounds that can act independently include any of a variety of known chemotherapeutic compounds that can inhibit tumor growth, inhibit metastasis growth and/or formation, decrease the size of a tumor or metastasis, eliminate a tumor or metastasis, without reducing the ability of a microorganism to accumulate in a tumor, replicate in the tumor, and cause or enhance an anti-tumor immune response in the subject.

Therapeutic compounds that act in conjunction with the bacteria include, for example, compounds that alter the gene expression of the bacteria or compounds that can interact with a bacterially-expressed gene and/or gene product, or compounds that can inhibit bacterial proliferation, including compounds toxic to the bacteria. Therapeutic compounds that can act in conjunction with the bacteria include, for example, therapeutic compounds that increase the proliferation, toxicity, tumor cell killing, or immune response eliciting properties of the bacteria, and also can include, for example, therapeutic compounds that decrease the proliferation, toxicity, immune response-eliciting, or cell killing properties of the bacteria. Thus, provided herein are methods of administering to a subject one or more therapeutic compounds that can act in conjunction with the bacteria to increase the proliferation, toxicity, tumor cell killing, or immune response eliciting properties of the bacteria. Also provided herein are methods of administering to a subject one or more therapeutic compounds that can act in conjunction with the bacteria to decrease the proliferation, toxicity, immune response-eliciting, or cell killing properties of the bacteria.

Also provided herein are pharmaceutical compositions containing bacteria as described above, wherein the bacteria furthermore contains one or more expressible DNA sequence(s) encoding (a) protein(s) or a functional RNA suitable for tumor therapy and/or elimination of metastatic tumors, such as a cytotoxic protein, a cytostatic protein, a protein inhibiting angiogenesis, or a protein stimulating apoptosis. Such proteins are well-known to the person skilled in the art. Exemplary therapeutic proteins or products include, but are not limited to, a cell-surface receptor, a cytokine, a chemokine, an apoptotic protein, an antimitotic oligopeptide, a toxin, a tumor antigen, a prodrug converting enzyme), an RNA (e.g., ribozyme, RNAi, siRNA), or a compound that is generated by an encoded polypeptide and, in some examples, the cellular machinery of the tumor or immunoprivileged tissue or cells (e.g., a metabolite, a converted prodrug).

Therapeutic agents that can be administered to the subject in addition to administering a bacterium or plurality thereof to a subject can be, for example, an anti-cancer agents including, but are not limited to, cytokines, growth factors, photosensitizing agents, radionuclides, toxins, anti-metabolites, signaling modulators, anti-cancer antibiotics, anti-cancer antibodies, angiogenesis inhibitors, radiation therapy, chemotherapeutic compounds, or a combination thereof.

Exemplary cytokines and growth factors include, for example, interleukins, such as interleukin-1, interleukin-2, interleukin-6 and/or interleukin-12, tumor necrosis factors, such as tumor necrosis factor alpha (TNF-α), interferons such as interferon gamma (IFN-γ), granulocyte macrophage colony stimulating factor (GM-CSF), angiogenins, and a tissue factors.

Exemplary photosensitizing agents include, for example, indocyanine green, toluidine blue, aminolevulinic acid, texaphyrins, benzoporphyrins, phenothiazines, phthalocyanines, porphyrins, such as sodium porfimer, chlorins, such as tetra (m-hydroxyphenyl)chlorin or tin(IV) chlorin e6, purpurins, such as tin ethyl etiopurpurin, purpurinimides, bacteriochlorins, pheophorbides, a pyropheophorbides and cationic dyes.

Exemplary radionuclides include, for example, $^{11}$Carbon, $^{11}$Fluorine, $^{13}$Carbon, $^{13}$Nitrogen, $^{15}$Nitrogen, $^{15}$Oxygen, $^{18}$Fluorine, $^{19}$Fluorine, $^{24}$Sodium, $^{32}$Phosphate, $^{42}$Potassium, $^{51}$Chromium, $^{52}$Iron, $^{55}$Iron, $^{59}$Iron, $^{57}$Cobalt, $^{58}$Cobalt, $^{60}$Cobalt, $^{57}$Nickle, $^{64}$Copper, $^{60}$Copper(II), $^{67}$Copper(II), $^{67}$Gallium, $^{68}$Gallium, $^{75}$Selenium, $^{81}$Krypton, $^{82}$Rubidium, $^{89}$Strontium, $^{92}$Strontium, $^{90}$Yttirum, $^{99}$Technetium, $^{103}$Palladium, $^{106}$Ruthenium, $^{111}$Indium, $^{117}$Lutetium, $^{123}$Iodine, $^{125}$Iodine, $^{131}$Iodine, $^{133}$Xenon, $^{137}$Cesium, $^{153}$Samarium, $^{153}$Gadolinium, $^{165}$Dysprosium, $^{166}$Holmium, $^{169}$Ytterbium, $^{177}$Leutium, $^{186}$Rhenium, $^{188}$Rhenium, $^{192}$Iridium, $^{198}$Gold, $^{201}$Thallium, $^{211}$Astatine, $^{212}$Bismuth or $^{213}$Bismuth.

Exemplary toxins include, for example, 5-fluorouridine, calicheamicin and maytansine.

Exemplary anti-metabolites include, for example, methotrexate, 5-fluorouracil, 6-mercaptopurine, cytosine arabinoside, hydroxyurea, and 20-chlorodeoxyadenosine.

Exemplary signaling modulators include, for example, an inhibitors of macrophage inhibitory factor, a toll-like receptor agonists and stat 3 inhibitors.

Exemplary anti-cancer antibiotics include, for example, anthracyclines, pleomycins, such as pleomycin and peplomycin sulfate, mitomycins such as mitomycin C, actinomycins such as actinomycin D, zinostatinstimalamer, polypeptides such as neocarzinostatin, and anthracyclines, such as doxorubicin hydrochloride (adriamycin), idarubicin hydrochloride, daunorubicin hydrochloride, aclarubicin Hydrochloride, epirubicin hydrochloride, and pururubicin hydrochloride.

Exemplary anti-cancer antibodies include, for example, Rituximab (RITUXAN), ADEPT, Trastuzumab (HERCEPTIN), Tositumomab (BEXXAR), Cetuximab (ERBITUX), Ibritumomab (ZEVALIN), Alemtuzumab (Campath-1H), Epratuzumab (Lymphocide), Gemtuzumab ozogamicin (MYLOTARG), Bevacimab (AVASTIN), and Edrecolomab (PANOREX).

Exemplary angiogenesis inhibitors include, for example, collagenase inhibitors such as metalloproteinases and tetracyclines such as minocycline, naturally occurring peptides such as endostatin and angiostatin, fungal and bacterial derivatives, such as fumagillin derivatives like TNP-470, aptamer antagonist of VEGF batimastat, Captopril, cartilage derived inhibitor (CDI), genistein, interleukin 12 Lavendustin A, medroxyprogesterone acetate, recombinant human platelet factor 4(rPF4), taxol, D-gluco-D-galactan sulfate (Tecogalan(=SP-PG, DS-4152)), thalidomide, thrombospondin.

Exemplary radiation therapy includes, but is not limited to, photodynamic therapy, radionuclides, radioimmunotherapy and proton beam treatment. Exemplary chemotherapeutic compounds provided herein are alkylating agents such as thiotepa and cyclophosphamide; alkyl sulfonates such as busulfan, improsulfan and piposulfan; aziridines such as benzodopa, carboquone, meturedopa and uredopa; ethylenimines and methylamelamines including altretamine, triethylenemelamine, triethylenephosphoramide, triethylenethiophosphoramide and trimethylomelamine nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; NOVANTRONE; teniposide; daunomycin; aminopterin; XELODA; ibandronate; CPT11; topoisomerase inhibitor RFS 2000; difluoromethylornithine (DMFO); retinoic acid; esperamicins; capecitabine; Erlotinib (TARCEVA); sunitinib malate (SUTENT) and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone and toremifene (FARESTON); and antiandrogens such as flutamide, nilutamide, bicalutamide, leuprolide and goserelin; and pharmaceutically acceptable salts, acids or derivatives of any of the above. Such chemotherapeutic compounds that can be used herein include compounds whose toxicities preclude use of the compound in general systemic chemotherapeutic methods. Particular exemplary platinum coordination complexes include, but are not limited to, cisplatin, carboplatin and oxaliplatin.

In other examples, the bacteria can express a protein that converts a less active compound into a compound that causes tumor cell death. The protein can be an enzyme converting an inactive substance (pro-drug) administered to the organism into an active substance, i.e. toxin, which kills the tumor or metastasis. Exemplary methods of conversion of such a prodrug compound include enzymatic conversion and photolytic conversion. For example, the enzyme can be glucuronidase converting the less toxic form of the chemotherapeutic agent glucuronyldoxorubicin into a more toxic form. Exemplary prodrugs include, but are not limited to, 5-fluorouracil, gancyclovir, 6-methylpurine deoxyriboside, cephalosporin-doxorubicin, 4-[(2-chloroethyl)(2-mesuloxyethyl)amino]benzoyl-L-glutamic acid, indole-3-acetic acid, 7-ethyl-10-[4-(1-piperidino)-1-piperidino]carbonyloxycampotothecin, bis-(2-chloroethyl)amino-4-hydroxyphenylaminomethanone 28, 1-chloromethyl-5-hydroxy-1,2-dihyro-3H-benz[e]indole, epirubicin-glucoronide, 5'-deoxy-5-fluorouridine, cytosine arabinoside, and linamarin. A large variety of protein/prodrug compound pairs are known in the art, and include, but are not limited to, Herpes simplex virus thymidine kinase/gancyclovir, varicella zoster thymidine kinase/gancyclovir, cytosine deaminase/5-fluorouracil, purine nucleoside phosphorylase/6-methylpurine deoxyriboside, beta lactamase/cephalosporin-doxorubicin, carboxypeptidase G2/4-[(2-chloroethyl)(2-mesuloxyethyl)amino]benzoyl-L-glutamic acid, cytochrome P450/acetominophen, horseradish peroxidase/indole-3-acetic acid, nitroreductase/CB1954, rabbit carboxylesterase/7-ethyl-10-[4-(1-piperidino)-1-piperidino]carbonyloxycampotothecin, mushroom tyrosinase/bis-(2-chloroethyl)amino-4-hydroxyphenylaminomethanone 28, beta galactosidase/1-chloromethyl-5-hydroxy-1,2-dihyro-3H-benz[e]indole, beta glucuronidase/epirubicin-glucoronide, thymidine phosphorylase/5'-deoxy-5-fluorouridine, deoxycytidine kinase/cytosine arabinoside, beta-lactamase and linamerase/linamarin.

In a particular example, the gene encoding the prodrug converting enzyme is directed by a promoter which is inducible additionally ensuring that the conversion of the pro-drug into the toxin only occurs in the target tissue, i.e. tumor. Such promoters include, for example, IPTG-, antibiotic-, heat-, pH-, light-, metal-, aerobic-, host cell-, drug-, cell cycle-, sugar (e.g., arabinose or xylose) or tissue specific-inducible promoters.

Additional examples of suitable therapeutic proteins are human endostatin and the chimeric PE37/TGF-alpha fusion protein. Endostatin is a carboxyterminal peptide of collagen XVIII which has been characterized (Ding et al. (1998) *PNAS USA* 95: 10443). It has been shown that endostatin inhibits endothelial cell proliferation and migration, induces G1 arrest and apoptosis of endothelial cells in vitro, and has anti-tumor effect in a variety of tumor models. Intravenous or intramuscular injection of viral DNA and cationic liposome-complexed plasmid DNA encoding endostatin result in limited expression levels of endostatin in tumors. However intratumoral injection of purified endostatin shows remarkable inhibition of tumor growth. *Pseudomonas* exotoxin (PE) is a bacterial toxin secreted by *Pseudomonas aeruginosa*. PE elicits its cytotoxic effect by inactivating elongation factor 2 (EF-2), which results in blocking of protein synthesis in mammalian cells. Single chain PE is functionally divided into three domains: domain Ia is required for binding to cell surface receptor, domain II is required for translocating the toxin into the target cell cytosol, and domain III is responsible for cytotoxicity by inactivating EF-2. PE40 is derived from wild type *Pseudomonas* exotoxin that lacks the binding domain Ia. Other proteins such as antibody fragments or protein ligands can be inserted in place of the binding domain. This will render the PE40-ligand fusion protein specific to its receptor. One of the highly specific engineered chimeric toxins is the TGF alpha/PE40 fusion protein, where the C-terminus of TGF alpha polypeptide has been fused in frame with the N-terminus of the PE40 protein. TGF alpha is one of the ligands of epidermal growth factor receptor (EGFR), which has been shown to be preferentially expressed on the surface of a variety of tumor cells. TGF alpha-PE40 fusion protein has been shown to be highly toxic to tumor cells with elevated EGFRs on the cell surface and while it is less toxic to nearby cells displaying fewer numbers of surface EGFR. The toxicity of TGF'alpha-PE40 chimeric protein is dependent on a proteolytic processing step to convert the chimeric protein into its active form, which is carried out by the target. To overcome the requirement for proteolysis, a new chimeric toxin protein that does not require processing has been constructed by Theuer et al. (1992) *J. Biol. Chem.* 267: 16872. The novel fusion protein is termed PE37/TGF alpha, which exhibited higher toxicity to tumor cells than the TGF alpha-PE40 fusion protein. Thus, in one example of the pharmaceutical composition, the protein suitable for tumor therapy is endostatin (for inhibition of tumor growth) or recombinant chimeric toxin PE37/transforming growth factor alpha (TGF-alpha) (for cytotoxicity to tumor cells).

Moreover, the delivery system of the present application even allows the application of compounds which could so far not be used for tumor therapy due to their high toxicity when systemically applied. Such compounds include proteins inhibiting elongation factors, proteins binding to ribosomal subunits, proteins modifying nucleotides, nucleases, proteases or cytokines (e.g., IL-2 or IL-12), since experimental data suggest that the local release of cytokines might have a positive effect on the immunosuppressive status of the tumor.

b. Therapeutic Gene Product Expression

The bacteria for use in the methods provided herein can express one or more genes whose products cause cell death or whose products cause an anti-tumor immune response; such genes can be considered therapeutic genes. A variety of therapeutic gene products, such as toxic or apoptotic proteins, or siRNA, are known in the art, and can be used with the bacteria in the methods provided herein. The therapeutic gene products can act by directly killing the surrounding tumor cells, inducing apoptosis, inhibiting one or more essential cellular processes, inducing an immune response against the cell, or by interacting with a compound that induces an immune response or cell death (e.g., an enzyme that converts a less active compound to a cytotoxic compound). A large number of therapeutic proteins that can be expressed for tumor treatment are known in the art, including, but not limited to, tumor suppressors, toxins, cytostatic proteins, and costimulatory molecules such as cytokines and chemokines. Costimulatory molecules for the methods provided herein include any molecules which are capable of enhancing immune responses to an antigen/pathogen in vivo and/or in vitro. Costimulatory molecules also encompass any molecules which promote the activation, proliferation, differentiation, maturation, or maintenance of lymphocytes and/or other cells whose function is important or essential for immune responses. An exemplary, non-limiting list of therapeutic proteins includes WT1, p53, p16, Rb, BRCA1, cystic fibrosis transmembrane regulator (CFTR), Factor VIII, low density lipoprotein receptor, beta-galactosidase, alpha-galactosidase, beta-glucocerebrosidase, insulin, parathyroid hormone, alpha-1-antitrypsin, rsCD40L, Fas-ligand, TRAIL, TNF, antibodies, microcin E492, diphtheria toxin, *Pseudomonas exotoxin, Escherichia coli* Shig toxin, Escherichia coli Verotoxin 1, and hyperforin. Exemplary cytokines include, but are not limited to, chemokines and classical cytokines, such as the interleukins, including for example, interleukin-1, interleukin-2, interleukin-6 and interleukin-12, tumor necrosis factors, such as tumor necrosis factor alpha (TNF-α), interferons such as interferon gamma (IFN-γ), granulocyte macrophage colony stimulating factor (GM-CSF) and exemplary chemokines including, but not limited to CXC chemokines such as IL-8 GROα, GROβ, GROγ, ENA-78, LDGF-PBP, GCP-2, PF4, Mig, IP-10, SDF-1α/β, BUNZO/STRC33, I-TAC, BLC/BCA-1; CC chemokines such as MIP-1α, MIP-1β, MDC, TECK, TARC, RANTES, HCC-1, HCC-4, DC-CK1, MIP-3α, MIP-3β, MCP-1, MCP-2, MCP-3, MCP-4, Eotaxin, Eotaxin-2/MPIF-2, 1-309, MIP-5/HCC-2, MPIF-1, 6Ckine, CTACK, MEC; lymphotactin; and fractalkine. Exemplary other costimulatory molecules include immunoglobulin superfamily of cytokines, such as B7.1, B7.2.

In other examples, the bacteria can express a protein that converts a less active compound into a compound that causes tumor cell death. Exemplary methods of conversion of such a prodrug compound include enzymatic conversion and photolytic conversion. A large variety of protein/compound pairs are known in the art, and include, but are not limited to, Herpes simplex virus thymidine kinase/ganciclovir, Herpes simplex virus thymidine kinase/(E)-5-(2-bromovinyl)-2'-deoxyuridine (BVDU), varicella zoster thymidine kinase/ganciclovir, varicella zoster thymidine kinase/BVDU, varicella zoster thymidine kinase/(E)-5-(2-bromovinyl)-1-beta-D-arabinofuranosyluracil (BVaraU), cytosine deaminase/5-fluorouracil, cytosine deaminase/5-fluorocytosine, purine nucleoside phosphorylase/6-methylpurine deoxyriboside, beta lactamase/cephalosporin-doxorubicin, carboxypeptidase G2/4-[(2-chloroethyl)(2-mesuloxyethyl)amino]benzoyl-L-glutamic acid (CMDA), carboxypeptidase A/methotrexate-phenylamine, cytochrome P450/acetominophen, cytochrome P450-2B1/cyclophosphamide, cytochrome P450-4B1/2-aminoanthracene, 4-ipomeanol, horseradish peroxidase/indole-3-acetic acid, nitroreductase/CB1954, rabbit carboxylesterase/7-ethyl-10-[4-(1-piperidino)-1-piperidino]carbonyloxycamptothecin (CPT-11), mushroom tyrosinase/bis-(2-chloroethyl)amino-4-hydroxyphenylaminomethanone 28, beta galactosidase/1-chloromethyl-5-hydroxy-1,2-dihyro-3H-benz[e]indole, beta glucuronidase/epirubicin glucuronide, thymidine phosphorylase/5'-deoxy-5-fluorouridine, deoxycytidine kinase/cytosine arabinoside, and linamerase/linamarin.

In another example, the therapeutic gene product can be a protein ligand, such as antitumor oligopeptide. Antitumor oligopeptides are short protein peptides with high affinity and specificity to tumors. Such oligopeptides could be enriched and identified using tumor-associated phage libraries (Akita et al. (2006) *Cancer Sci.* 97(10):1075-1081). These oligopeptides have been shown to enhance chemotherapy (U.S. Pat. No. 4,912,199). The oligopeptides can be expressed by the bacteria provided herein. Expression of the oligopeptides can elicit anticancer activities on their own or in combination with other chemotherapeutic agents. An exemplary group of antitumor oligopeptides is antimitotic peptides, including, but not limited to, tubulysin (Khalil et al. (2006) *Chembiochem.* 7(4): 678-683), phomopsin, hemiasterlin, taltobulin (HTI-286, 3), and cryptophycin. Tubulysin is from myxobacteria and can induce depletion of cell microtubules and trigger the apoptotic process. The antimitotic peptides can be expressed by the bacteria provide herein and elicit anticancer activities on their own or in combination with other therapeutic modalities.

In one example, the therapeutic gene product can be controlled by a regulatory sequence. Suitable regulatory sequences which, for example, are functional in a mammalian host cell are well known in the art. In one example, the regulatory sequence can contain a natural or synthetic promoter. Such promoters include, for example, IPTG-, antibiotic-, heat-, pH-, light-, metal-, aerobic-, host cell-, drug-, cell cycle-, sugar (e.g., arabinose or xylose) or tissue specific-inducible promoters.

3. State of Subject

In another example, the methods provided herein for administering a bacterium to a subject can be performed on a subject in any of a variety of states, including an anesthetized subject, an alert subject, a subject with elevated body temperature, a subject with reduced body temperature or other state of the subject that is known to affect the accumulation of bacterium in the tumor. It has been determined that a subject that is anesthetized can have a decreased rate of accumulation of a bacterium in a tumor relative to a subject that is not anesthetized. Accordingly, provided herein are methods of administering a bacterium to a subject, where the methods can include administering a bacterium to a subject where the subject is not under general anesthesia. For example, the subject can be under local anesthesia, or can be unanesthetized. It has been determined that a subject with decreased body temperature can have a decreased rate of accumulation of a bacterium in a tumor relative to a subject with a normal body temperature. Accordingly, provided herein are methods of administering a bacterium to a subject, where the methods can include administering a bacterium to a subject with altered body temperature, where the alteration of the body temperature can influence the ability of the bacterium to accumulate in a tumor; typically, a decrease in body temperature can decrease the ability of a bacterium to accumulate in a tumor. Thus, in one exemplary example, a method is provided for administering a bacterium to a subject, where the method includes elevating the body temperature of the subject to a temperature above normal, and administering a bacterium to the subject, where the bacterium can accumulate in the tumor more readily in the subject with higher body temperature relative to the ability of the bacterium to accumulate in a tumor of a subject with a normal body temperature.

4. Monitoring Tumor Size

Provided herein are methods of monitoring tumor and/or metastasis size and location, including the methods of imaging as described elsewhere herein. Tumor and or metastasis size can be monitored by any of a variety of methods known in the art, including external assessment methods or tomographic or magnetic imaging methods. In addition to the methods known in the art, methods provided herein, for example, monitoring the localization of radiolabeled compounds that bind to endogenous bacterial thymidine kinase, can be used for monitoring tumor and/or metastasis size.

Monitoring size over several time points can provide information regarding the increase or decrease in size of a tumor or metastasis, and can also provide information regarding the presence of additional tumors and/or metastases in the subject. Monitoring tumor size over several time points can provide information regarding the development of a neoplastic disease in a subject, including the efficacy of treatment of a neoplastic disease in a subject.

5. Monitoring General Health Diagnostics

The methods provided herein also can include methods of monitoring the health of a subject. Some of the methods provided herein are therapeutic methods, including neoplastic disease therapeutic methods. Monitoring the health of a subject can be used to determine the efficacy of the therapeutic method, as is known in the art. The methods provided herein also can include a step of administering a bacterium to a subject. Monitoring the health of a subject can be used to determine the pathogenicity of a bacterium administered to a subject. Any of a variety of health diagnostic methods for monitoring disease such as neoplastic disease, infectious disease, or immune-related disease can be monitored, as is known in the art. For example, the weight, blood pressure, pulse, breathing, color, temperature or other observable state of a subject can indicate the health of a subject. In addition, the presence or absence or level of one or more components in a sample from a subject can indicate the health of a subject. Typical samples can include blood and urine samples, where the presence or absence or level of one or more components can be determined by performing, for example, a blood panel or a urine panel diagnostic test. Exemplary components indicative of a subject's health include, but are not limited to, white blood cell count, hematocrit, c-reactive protein concentration.

g. Pharmaceutical compositions, combinations and kits

1. Pharmaceutical Compositions

Provided herein are pharmaceutical compositions, combinations and kits containing any of the bacteria for use in the methods provided herein. Pharmaceutical compositions provided herein can be used for in vivo for diagnostic or therapeutic purposes and can be formulated in any conventional manner by mixing a selected amount of the bacteria with one or more physiologically/pharmaceutically acceptable carriers or excipients. Selection of the carrier or excipient is within the skill of the administering individual/professional and can depend upon a number of parameters. These include, for example, the mode of administration (e.g., systemic, intraperitoneal, subcutaneous, oral, nasal, pulmonary, local, topical or any other mode) and disorder treated. The pharmaceutical compositions provided herein can be formulated for single dosage or multiple dosage administration or for dilution or other modification. The concentrations of the compounds in the formulations are effective for delivery of an amount, upon administration, that is effective for the intended treatment and individual. The compositions can be formulated for single dosage administration or for a plurality of dose administrations. Administrations can be concomitant or sequential. To formulate a composition, the weight fraction of a compound or mixture thereof is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

Examples of suitable pharmaceutical carriers are known in the art and include phosphate buffered saline solutions, water, emulsions, such as oil/water emulsions, various types of wetting agents and sterile solutions. Such carriers can be formulated by conventional methods and can be administered to the subject at a suitable dose.

In an exemplary example, bacteria for use in the methods provided herein are formulated as pharmaceutical compositions and can, optionally, include a variety of pharmaceutically acceptable excipients or pharmaceutically suitable pharmaceutical carriers. Radiolabeled compounds for imaging, siderophores, antibodies, peptides, proteins, molecules for induction of gene expression (e.g., arabinose), and nanoparticles provided herein also can be formulated as pharmaceutical compositions, and can be formulated in the same or different pharmaceutical composition as the bacteria.

The bacteria can be formulated as the sole pharmaceutically active ingredient in the composition or can be combined with other ingredients. The active compound is included in the pharmaceutically acceptable carrier in an amount sufficient to exert a therapeutically useful effect in the absence of undesirable side effects on the subject treated; or to be present in sufficient amounts to allow for detection using the methods described herein. The therapeutically effective concentration can be determined empirically by testing the compounds in known in vitro and in vivo systems, such as the assays provided herein. The active compounds can be administered by any appropriate route, for example, intraperitoneal, parenteral, intravenous, intradermal, subcutaneous or topical administration, in liquid, semi-liquid or solid form and are formulated in a manner suitable for each route of administration.

The concentration of active compound in the composition depends on absorption, inactivation and excretion rates of the active compound, the dosage schedule, and amount administered as well as other factors known to those of skill in the art. As described further herein, dosages can be determined empirically using dosages known in the art for administration of bacteria.

The compositions, if desired, can be presented in a package, in a kit or dispenser device, that can contain one or more unit dosage forms containing the active ingredient. The pack or dispenser device can be accompanied by instructions for administration. The compositions containing the active agents can be packaged as articles of manufacture containing packaging material, an agent provided herein, and a label that indicates the disorder for which the agent is provided.

2. Combinations

Combinations can include two or more agents provided herein. For example, a combination can include a bacteria for use in the methods provided herein that expresses an endogenous gene that binds a radiolabeled compound, the radiolabeled compound and a pharmaceutically acceptable carrier. For example, a combination can include bacteria for use in the methods provided herein expressing an exogenous gene that is regulated by an inducible promoter, a molecule that induces the promoter (e.g., arabinose) and a pharmaceutically acceptable carrier.

A detectable compound can include a ligand or substrate or other compound that can interact with and/or bind specifically to a bacterially expressed protein or RNA molecule, and can provide a detectable signal, such as a signal detectable by any of the imaging techniques provided herein or otherwise known in the art. Exemplary detectable compounds can be, or can contain, an imaging agent such as a magnetic resonance, ultrasound or tomographic imaging agent, including a radionuclide. Particular detectable compounds for use in the PET imaging methods provided herein include, but are not limited to, radiolabeled metabolic compounds. Exemplary of such compounds are 2'-fluoro-2'deoxy-1-β-D-arabinofuranosyl-5-[$^{125}$I]iodo-uracil ([$^{125}$I]-FIAU), 2'-fluoro-2'deoxy-1-β-D-arabinofuranosyl-5-[$^{124}$I]iodo-uracil ([$^{124}$I]-FIAU), 9-[4-[$^{18}$F]fluoro-3-(hydroxymethyl)butyl]guanine ([$^{18}$F]-FHBG), 9-[(3-[$^{18}$F]-fluoro-1-hydroxy-2-propoxy)methyl]guanine ([$^{18}$F]-FHPG), 2'-deoxy-2'-[$^{18}$F]fluoro-β-D-5-methyl-β-D-arabinofuranosyluracil ([$^{18}$F]-FMAU), 3'-deoxy-3'-[$^{18}$F]fluorothymidine ([$^{18}$F]-FLT), 2'-[$^{18}$F]fluoro-2'deoxy-1 β-D-arabinofuranosyl-5-ethyl-uracil ([$^{18}$F]-FEAU) and 2'-deoxy-2'-[$^{18}$F]fluoro-5-iodo-1-β-D-arabinofuranosyluracil ([$^{18}$F]-FIAU).

The detectable compound can include any of a variety of compounds as provided elsewhere herein or are otherwise known in the art. Typically, the detectable compound included with the bacteria in the combinations provided herein will be a compound that is a substrate, a ligand, or can otherwise specifically interact with, a protein or RNA encoded by the bacteria; in some examples, the protein or RNA is an exogenous protein or RNA. Typically, the detectable compound included with the bacteria in the combinations provided herein will be a ligand that interacts with the bacteria. In a non-limiting example, a radiolabeled compound, such as radiolabeled metabolic compound, will be administered to an individual concomitant with, or subsequent to, bacteria that express an endogenous thymidine kinase that interacts and phosphorylates the compound. Any combination of elements provided herein can be combined to image a tumor. In addition elements used in the imaging provided herein can be combined with other methods known in the art for imaging tumors.

Therapeutic compounds can include therapeutic compounds provided herein or known in the art to act in concert with the bacteria. Typically, the therapeutic compound included with the bacteria in the combinations provided herein will be a compound that can act in concert with the bacteria, such as described elsewhere herein. In a non-limiting example, a siderophore conjugated to a therapeutic agent will be administered to an individual concomitant with, or subsequent to, bacteria having a receptor that recognizes and transports the siderophore. In another non-limiting example, an antibody conjugated to a therapeutic agent will be administered to an individual concomitant with, or subsequent to, bacteria having a receptor that specifically binds the antibody. Any combination of elements provided herein can be combined to for therapeutic treatment.

3. Kits

Kits can include the pharmaceutical compositions and/or combinations provided herein, and one or more components such as instructions for use, one or more other microorganisms or cells, a device for detecting a microorganism or cell in a subject, a device for administering a compound to a subject, and a device for administering a compound to a subject.

Kits are packaged combinations that, optionally, include other reagents or devices, or instructions for use. Exemplary kits can include the microorganisms or cells provided herein and can, optionally, include one or more components such as instructions for use, a device for detecting a microorganism or cell in a subject and a device for administering a compound/composition to a subject.

In one example, a kit can contain instructions. Instructions typically include a tangible expression describing the microorganism or cell and, optionally, other components included in the kit, and methods for administration, including methods for determining the proper state of the subject, the proper dosage amount, and the proper administration method, for administering the bacteria. Instructions can also include guidance for monitoring the subject over the duration of the treatment time.

In another example, a kit can contain a device for detecting a microorganism or cell in a subject. Devices for detecting a microorganism or cell in a subject can include a tomographic scanner, such as a PET, CT, CAT, SPECT or other related scanner, a low light or fluorescence imaging device for detecting light, for example emitted from luciferase or fluoresced from GFP, RFP, BFP, CFP, YFP, OFP, far-red fluorescent protein or near-infrared fluorescent protein, a magnetic resonance measuring device such as an MRI or NMR device, an ultrasound device, or other device that can be used to detect a protein expressed by the bacteria within the subject. Typically, the device of the kit will be able to detect one or more proteins expressed by the bacteria of the kit. Any of a variety of kits containing bacteria and detection devices can be included in the kits provided herein, for example, bacteria expressing luciferase and a low light imager, or a bacteria expressing green fluorescence protein and a low light imager or fluorescence imager.

Kits provided herein also can include a device for administering the bacteria to a subject. Any of a variety of devices known in the art for administering compositions can be included in the kits provided herein. Exemplary devices include a hypodermic needle, an intravenous needle, a catheter, a needle-less injection device, an inhaler, and a liquid dispenser such as an eyedropper. Typically, the device for administering the bacteria of the kit will be compatible with the bacteria of the kit; for example, a needle-less injection device such as a high pressure injection device can be included in kits with the bacteria not damaged by high pressure injection, but is typically not included in kits with the bacteria damaged by high pressure injection.

Kits provided herein also can include a device for administering a compound/composition (e.g., siderophore, antibody, nanoparticle, peptide or protein) to a subject. Any of a variety of devices known in the art for administering medications to a subject can be included in the kits provided herein. Exemplary devices include a hypodermic needle, an intravenous needle, a catheter, a needle-less injection an inhaler, and a liquid dispenser. Typically the device for administering the compound of the kit will be compatible with the desired method of administration of the compound. For example, a compound to be delivered subcutaneously can be included in a kit with a hypodermic needle and syringe.

H. EXAMPLES

The following examples are included for illustrative purposes only and are not intended to limit the scope of the examples provided herein.

Example 1

In vitro [$^{18}$F]-FDG and [$^{18}$F]-FEAU Uptake into *E. coli* Nissle

The in vitro uptake of 2'-[$^{18}$F]fluoro-2'deoxy-D-glucose ([$^{18}$F]-FDG) and 2'-[$^{18}$F]fluoro-2'deoxy-1-β-D-arabinofuranosyl-5-ethyl-uracil ([$^{18}$F]-FEAU) by the probiotic bacterial strain *Escherichia coli* Nissle 1917 (EcN) were compared. EcN is a tumor-colonizing strain that lacks protein toxin expression. The EcN strain used in the study can specifically colonize tumors and harbors a luxABCDE encoding plasmid, pBR322DEST P$_{BAD}$-DUAL-term (SEQ ID NO: 1), which enables the bacteria to be detected with bioluminescence imaging when induced with L-arabinose (Stritzker et al. (2007) *Int. J. Med. Microbiol.* 297:51-62). Light is emitted from the bacteria as a result of expression of a heterodimeric luciferase (encoded by luxAB), which catalyzes the oxidation of reduced flavin mononucleotide and a long-chain fatty aldehyde, synthesized by a fatty acid reductase complex encoded by luxCDE (Francis et al. (2000) *Infect. Immun.* 68:3594-600).

Clinical grade [$^{18}$F]-FDG was obtained from IBA Molecular (Somerset, N.J.) with a specific activity >41 MBq/μmol (>11 mCi/μmol) and a radiochemical purity of 99% by TLC and 98% by HPLC. [$^{18}$F] FEAU was synthesized by coupling the radiolabeled fluoro sugar with the silylated pyrimidine derivatives following a procedure previously described (Serganova et al. (2004) *Cancer Res.* 64:6101-8). The specific activity of the [$^{18}$F]-FDG product was ~37 GBq/μmol (~1 Ci/μmol) and radiochemical purity was >95% following purification by HPLC.

An overnight culture of EcN was diluted 1:50 into 5 ml fresh LB-broth, supplemented with 0.925 MBq (25 μCi) of [$^{18}$F]-FDG or [$^{18}$F]-FEAU. The cultures were grown at 37° C. for 4 hours. The bacteria were harvested by centrifugation, washed twice with PBS and the radioactivity in the pelleted bacteria and medium was measured in a gamma counter (Packard, United Technologies, Downers Grove, Ill.). A 120-fold enrichment of [$^{18}$F]-FDG and a 6.5-fold enrichment of [$^{18}$F]-FEAU radioactivity within EcN-bacteria compared to the radioactivity in the remaining LB-broth was observed.

Example 2

In vivo PET Imaging of *E. coli* Nissle Distribution in Tumor-bearing Mice

The in vivo uptake of [$^{18}$F]-FDG and [$^{18}$F]-FEAU by administered EcN bacteria was studied using a mouse tumor model and imaged by positron emission tomography (PET) scanning. A murine mammary carcinoma cell line 4T1 (ATCC-No: RL-2539) was cultured in RPMI containing 10% FCS. The cells were maintained at 37° C. with 5% $CO_2$ in air and subcultured twice weekly. For tumor cell implantation six to eight week old athymic nu/nu mice (NCI, MD) were used. The mice were housed five per cage and allowed food and water ad libitum for 1 week prior to tumor cell implantation. On the day of implantation, the 4T1 cells were removed from cell culture by trypsinization and washed in PBS. $3.3 \times 10^4$ cells, resuspended in 50 μl PBS, were subcutaneously implanted into the right and left shoulders of the mice.

For bacterial administration, EcN bacteria were grown in LB-broth supplemented with 100 μg/ml ampicillin to an $OD_{600nm}$ of 0.4, corresponding to $2 \times 10^8$ CFU/ml. The cells were washed twice in PBS and resuspended. The suspension was diluted to $4 \times 10^7$ CFU/ml and 100 μl was used for the injections. At two weeks post tumor cell implantation (tumor diameter >5 mm), the EcN bacteria ($4 \times 10^6$ CFU in 100 μl PBS) were administered systemically by lateral tail vein injection into the tumor bearing mice. Control mice were injected with 100 μl PBS via tail vein.

Following EcN injection, most bacteria (>99%) are quickly cleared from the animals and only a small percentage of the administered bacteria initially colonize the tumor (Stritzker et al. (2007) *Int. J. Med. Microbial.* 297:51-62). The tumor-colonizing bacteria grow exponentially for about 24 h before reaching a plateau of about $1 \times 10^9$ CFU/g of tumor tissue. During the growth phase, the bacteria are metabolically active and rapidly proliferate. For the imaging studies, two time points, 16 h and 72 h following EcN administration to tumor-bearing mice, were selected for administration of the tracer imaging agent, [$^{18}$F]-FDG or [$^{18}$F]-FEAU. At 16 h, the EcN is at a lower CFU/g of tumor tissue but is in rapid growth phase (i.e., more metabolically active). At 72 h the EcN is at a higher CFU/g of tumor tissue, but is in a more stationary phase. The number of bacteria per g tumor tissue at 16 h and 72 h post injection is approximately $1.8 \times 10^8$ and $1.6 \times 10^9$, respectively.

Prior to tracer administration, [$^{18}$F]-FDG or [$^{18}$F]-FEAU, the animals were starved 12 h and kept under anesthesia between tracer injection and imaging. In the [$^{18}$F]-FDG experimental group of mice (n=6 for each time point), each animal was injected intravenously by tail vein with 9.25 MBq (250 μCi) of [$^{18}$F]-FDG at either 16 or 72 hours after administration of EcN. Control mice received 9.25 MBq (250 μCi) of [$^{18}$F]-FDG following administration of PBS. [$^{18}$F]-FDG FDG PET scanning was performed 1 h after tracer administration using a 10 minute list mode acquisition.

In the [$^{18}$F]-FEAU experimental group of mice (n=8 for each time point), each animal was injected intravenously by tail vein with 9.25 MBq (250 μCi) of [$^{18}$F]-FEAU at either 16 or 72 hours after administration of EcN. Control mice received 9.25 MBq (250 μCi) of [$^{18}$F]-FEAU following administration of 100 μl PBS. [$^{18}$F]-FDG PET scanning was performed 2 h after tracer administration using a 10 minute list mode acquisition.

Imaging was performed using a Focus 120 microPET™ dedicated small-animal PET scanner (Concorde Microsystems Inc, Knoxyille, Tenn.). Mice were maintained under 2% isofluorane anesthesia with an oxygen flow rate of 2 l/min during the entire scanning period. Three-dimensional (3D) list-mode data were acquired using an energy window of 350-700 keV for $^{18}$F and 410-580 keV for $^{124}$I, respectively and a coincidence timing window of 6 ns. These data were then sorted into two-dimensional (2D) histograms by Fourier re-binning using a span of 3 and a maximum ring difference of 47. Transverse images were reconstructed by filtered back-projection using a ramp filter with a cut-off frequency equal to the Nyquist frequency in a 128×128×94 matrix comprised of 0.866×0.866×0.866-mm voxels. The image data were corrected for (a) non-uniformity of scanner response using a uniform cylinder source-based normalization, (b) dead time count losses using a singles count rate-based global correction, (c) physical decay to the time of injection, and (d) the $^{124}$I branching ratio. There was no correction applied for attenuation, scatter or partial-volume averaging. The count rates in the reconstructed images were converted to activity concentration (% of injected dose per gram of tissue, % ID/g) using a system calibration factor (μCi/ml/cps/voxel) derived from imaging of a rat-size phantom filled with a uniform aqueous solution of $^{18}$F. Axial and coronal views of the treated mice were imaged.

PET image analysis was performed using ASIPro™ software (Concorde Microsystems Inc., Knoxyille, Tenn.). For each PET scan, regions of interest (ROIs) were manually drawn over tumor, liver, skeletal muscle and heart. For each tissue and time point post-injection, the measured radioactivity was expressed as % ID/g. The maximum pixel value was recorded for each tissue and tumor-to-organ ratios for liver, skeletal muscle and heart were then plotted versus time. A two-tailed unpaired t-test was applied to determine the significance of differences between values using the MS Office 2003 Excel 11.0 statistical package (Microsoft, Redmond, Wash., USA).

The [$^{18}$F]-FDG tumor-to-organ ratios prior to injection of EcN bacteria were high in liver: (1.6±0.4) and muscle: (3.3±0.7) and low in heart (0.23±0.12). At 16 h after EcN injection, tumor-to-organ ratios were significantly increased for liver, muscle and heart (2.6±0.5, 5.4±1.1 and 0.31±0.8, respectively). At 72 h after EcN injection, the tumor-to-organ ratios were lower for the same tissues (2.2±0.8, 4.3±1.2 and 0.31±0.17, respectively). The data thus represents a ~1.7-fold enhancement of the tracer signal at 16 h (p<0.0001 for liver and muscle, p<0.06 for heart) and a ~1.4-fold enhancement at 72 h (p<0.05 for liver, muscle and heart). Although the post-EcN ratios were significantly higher than the pre-EcN ratios at 16 h and 72 h, the magnitude of this change and contrast in the images was relatively small. The decrease in the radioactivity ratio from 16 to 72 h did not correspond to the increase in bacteria over this time period.

The uptake of [$^{18}$F]-FEAU in tumors was much lower than that of [$^{18}$F]-FDG in the absence of EcN injection and the tumor-to-organ ratios (except for heart) were lower than those obtained with [$^{18}$F]-FDG, ranging from 1.4±0.3 for liver, 1.4±0.3 for heart and 1.7±0.4 for muscle. After injection of EcN bacteria, the tumor-to-organ ratios were substantially higher, reaching values of 2.0±0.7 at 16 h and 2.4±0.8 at 72 h for liver, 2.6±0.8 at 16 h and 3.0±1.3 at 72 h for muscle and 2.1±0.6 at 16 h and 2.9±0.8 at 72 h for heart, respectively. This represents a ~1.6-fold enhancement at 16 h (p<0.001) and a ~2.1-fold enhancement at 72 h (p<0.0002). The enhancement ratio after EcN injection was significantly higher (p<0.05) for [$^{18}$F]-FEAU compared to [$^{18}$F]-FDG at the 72 h time point. The greater enhancement in the tumor-to-organ ratios corresponded to a greater contrast observed in the PET images.

Example 3

Measurement of [$^{18}$F]-FEAU Uptake by Tissue Sampling

In vivo uptake of [$^{18}$F]-FEAU was measured in a separate experiment by measurement of tumor-to-organ (liver, spleen, heart and lung) [$^{18}$F]-FEAU radioactivity ratios via tissue sampling. The experiment was performed as described in Example 2 for administration of 4T1 mammary carcinoma cells, EcN bacteria and [$^{18}$F]-FEAU to the mice. Euthanized mice were rinsed with 100% ethanol prior to tissue removal. Organs, including liver, lung, spleen and heart, were sampled and weighed before radioactivity was measured. Tumor tissue was weighed and homogenized in 1 ml PBS. Serial dilutions of the homogenized sample were plated on L-arabinose containing LB-agar plates. Growing colonies were counted and confirmed to be EcN, harboring the pBR322DEST P$_{BAD}$-DUAL-term by bioluminescence imaging using an IVIS 100 Imaging system (Caliper, Hopkinton, Mass.). The remaining tumor suspension and organ samples were assayed for radioactivity in a gamma counter (Packard, United Technologies, Downers Grove, Ill.). [$^{18}$F]-FEAU radioactivity (% ID/g) in the samples was determined and tumor-to-organ ratios calculated. To assess the correlation between radioactivity and scintillation counter measurements, the Pearson correlation coefficient was computed.

In all tested tissues, the tumor to organ ratio increased significantly (p<0.02) after EcN administration. The higher tumor-to organ ratios at 72 h compared to 16 h corresponded with higher numbers of bacteria in the tumors at 72 h compared to 16 h.

Example 4

Analysis of In vivo Bacterial Concentration Versus [$^{18}$F]-FEAU Uptake

Using the data obtained in Example 2 for in vivo [$^{18}$F]-FEAU uptake, tumor radioactivity (% ID/g), corrected for background radioactivity, was plotted against the number of bacterial colony forming units per gram for each of the tumors imaged. A linear correlation was found between [$^{18}$F]-FEAU radioactivity and the number of colony forming units in the tumor (Linear fit: EcN cfu/g=1.1±0.1*10$^{10}$×% ID/g−2.0±1.3*10$^{8}$; Pearson coefficient, R$^2$=0.909). The results indicate that background-corrected [$^{18}$F]-FEAU uptake (% ID/g) reflects the number of EcN bacteria that have colonized the 4T1 xenografts. By contrast, Salmonella VNP20009, which overexpress HSV-TK (Soghomonyan et al. (2005) Cancer Gene Ther. 12:101-8), do not exhibit a strong correlation between [$^{18}$F]-FEAU uptake and bacterial number. Although Salmonella VNP20009 accumulates more radioactive tracer per bacterium due to overexpression of the thymidine kinase, a combined plot and fit of EcN bacteria versus [$^{18}$F]-FEAU radioactivity and the data from Salmonella VNP20009 bacteria in large and small tumors versus [$^{124}$I]-FIAU radioactivity published in Soghomonyan et al. (2005) Cancer Gene Ther. 12:101-8 revealed a stronger correlation between signal strength and bacterial number for EcN. A power equation was used to fit the previously published Salmonella VNP20009 data. EcN cfu/g=(1.78 e+10)×% ID/g^(1.39), R$^2$=0.913; Salmonella VNP20009 cfu/g=(2.74 e+10)×% ID/g^(3.78), R$^2$=0.491.

In addition, analysis of in vivo uptake of [$^{18}$F]-FDG showed that there was no correlation between the level of [$^{18}$F]-FDG uptake and number of viable bacteria in the tumors, and the signal-to-background ratio was not as high with [$^{18}$F]-FDG compared to that with [$^{18}$F]-FEAU and [$^{124}$I]-FIAU injected mice. This reflects the high base-line uptake (% ID/g) of [$^{18}$F]-FDG by the tumor compared to that of [$^{18}$F]-FEAU and FIAU. The lack of correlation between number of viable bacteria and [$^{18}$F]-FDG uptake also can be due to the presence of necrosis induced by the bacteria, or to the presence of high glucose-metabolizing macrophages in the tumors, which can contribute to alteration of [$^{18}$F]-FDG uptake in the tumor region (Stritzker et al. (2007) Int. J. Med. Microbiol. 297:51-62). For example, on day 1 after bacterial injection a high number of metabolically active bacteria were present, and only very small patches of necrosis were observed. Two days later, the number of bacteria increased, but the number of living cells in the tumor decreases dramatically since the necrotic region takes up 30-50% of the tumor volume. It was also observed that 4T1 xenografts in the absence of bacteria accumulate [$^{124}$I]-FIAU to low levels above background in comparison to the near background levels of [$^{18}$F]-FEAU accumulation in non-bacteria treated animals, suggesting higher specificity of [$^{18}$F]-FEAU for bacterial imaging. This observation is consistent with similar observations in other tumor systems (Serganova et al. (2004) Cancer Res. 64:6101-8; Tjuvajev et al. (1998) Cancer Res. 58:4333-41; Tjuvajev et al. (2002) J Nucl. Med. 43:1072-83; Buursma et al. (2006) Nucl. Med. Commun. 27:25-30; Bennett et al. (2001) Nature Medicine 7:859-863.).

Example 5

Measurement of In vivo [$^{124}$I]-FIAU Distribution Over Time

In vivo uptake of [$^{124}$I]-FIAU (5-iodo-2'-fluoro-2'deoxy-1-β-D-arabino-furanosyl-uracil) by EcN was selected for study in order to show that other thymidine analogs can be used to image bacteria. A time-course of [$^{124}$I]-FIAU uptake was performed to demonstrate the advantage of "later time imaging" with [$^{124}$I]-FIAU in order to achieve good target-to-background images. $^{124}$I has a radioactive half-life of 4 days, whereas $^{18}$F has a half-life of 110 minutes.

[$^{124}$I]-FIAU was synthesized by reacting the precursor of 5-Trimethylstannyl-1-(2-deoxy-2-fluoro-β-D-arabinofuranosyl)uracil (FTAU) with carrier free [$^{124}$I]NaI. $^{124}$I was produced on a 19 MeV cyclotron (Ebco Technologies, Inc.) using the $^{124}$Te(p,n) $^{124}$I nuclear reaction on an enriched $^{124}$TeO$_2$/Al$_2$O$_3$ solid target. Radiosynthesis was performed as previously described (Tjuvajev et al. (1998) Cancer Res. 58:4333-41; Tjuvajev et al. (2002) J. Nucl. Med. 43:1072-83). The specific activity of the product was >1000 GBq/μmol (>27 Ci/μmol). Radiochemical purity was >95%, as determined by radio-thin-layer chromatography using silica gel plates eluent: ethyl acetate/acetone/water (14:8:1, v/v/v) RF 0.7.

Mice bearing 4T1 xenografts were generated as described in Example 2. Prior to intravenous administration of [$^{124}$I]-FIAU, three mice were injected with EcN-bacteria and 3 mice with PBS (control). 37 MBq (1000 μCi) of [$^{124}$I]-FIAU was injected into each animal intravenously 72 h after bacterial injection. Potassium iodide was used to block the uptake of radioactive iodine by the thyroid. Imaging of [$^{124}$I]-FIAU uptake by PET was obtained 4, 8, 12, 24, 48 and 72 h after tracer administration with 10 minute list acquisition at the 4 h and 8 h imaging time points, 15 minute at the 12 h time point, 30 minute at 24 h time point and 60 minute at the 48 h and 72 h time points. After tracer administration and between imaging time points, the animals were allowed to awake and maintain normal husbandry.

PET images of [$^{124}$I]-FIAU uptake from the 4 and 8 h acquisition time points showed a very high background radioactivity. By 48 and 72 h, however, background [$^{124}$I]-FIAU radioactivity has cleared substantially and the tumor/background ratios were greater than 5 in the EcN-treated animals. The control (non-EcN-treated) animals also show some [$^{124}$I]-FIAU retention in the 4T1 xenografts. This represents a 2.5-fold enrichment of [$^{124}$I]-FIAU in the bacteria-treated tumors.

Example 6

In vivo Co-Localization of Bioluminescence and [$^{124}$I]-FIAU Uptake

In order to further verify that the increased [$^{124}$I]-FIAU PET signal reflected bacterial localization in 4T1 xenografts, bioluminescence imaging was also performed. The EcN used in the imaging experiments described in the Examples herein contains an L-arabinose inducible luciferase reporter plasmid, pBR322DEST P$_{BAD}$-DUAL-term (Stritzker et al. (2007) Int. J. Med. Microbiol. 297:51-62; SEQ ID NO:1). The pBR322DEST P$_{BAD}$-DUAL-term plasmid contains a fusion of the gene encoding GFP and the bacterial lux operon (lux-ABCDE). As described in Example 1, the plasmid enables the bacteria to be detected with bioluminescence imaging when induced with L-arabinose. Light is emitted from the bacteria as a result of expression of a heterodimeric luciferase, encoded by luxAB, which catalyzes the oxidation of reduced flavin mononucleotide and a long-chain fatty aldehyde, synthesized by a fatty acid reductase complex, encoded by luxCDE.

The animals described in Example 5 were imaged for localization of bioluminescence following the 72 h [$^{124}$I]-FIAU PET scans. Each animal was injected with 200 µl L-arabinose (25% w/v) to induce transcriptional expression of the luciferase reporter for bioluminescence imaging. Photon collection was performed 4 h later when the expression of luciferase was at its maximum (Stritzker et al. (2007) *Int J. Med. Microbiol.* 297:51-62). Images were acquired for 60 seconds, using an IVIS 100 Imaging System (Caliper, Hopkinton, Mass.). The photon emission (photons/cm²/s/steradian) from the animals and cell samples were analyzed using the LIVINGIMAGE 2.5 software (Caliper, Hopkinton, Mass.).

The L-arabinose-induced bioluminescence signal was readily detected and localized to the site of the 4T1 xenografts. Tumors in control mice (no EcN injection) did not show any light emission. No bioluminescence signal was observed in other tissues of the EcN-treated mice, indicating little or no bacterial presence in other tissues of the mice.

The invention claimed is:

1. A combination, comprising:
   a composition containing an *Escherichia coli* Nissle strain bacterium, wherein the only thymidine kinase (TK) expressed by the *Escherichia coli* Nissle strain bacterium is the endogenous thymidine kinase; and
   a composition containing a radiolabeled nucleoside analog compound.

2. The combination of claim 1, wherein the bacteria strain is Nissle 1917.

3. The combination of claim 1, wherein each composition is formulated for systemic administration.

4. The combination of claim 1, wherein the composition containing an *Escherichia coli* Nissle strain bacterium contains $1\times10^3$ or about $1\times10^3$ cfu colony forming units (cfu), $1\times10^4$ or about $1\times10^4$ cfu, $1\times10^5$ or about $1\times10^5$ cfu, $1\times10^6$ or about $1\times10^6$ cfu, $1\times10^7$ or about $1\times10^7$ cfu, $5\times10^7$ or about $5\times10^7$ cfu, $1\times10^8$ or about $1\times10^8$ cfu, $1\times10^9$ or about $1\times10^9$ cfu, $1\times10^{10}$ or about $1\times10^{10}$ cfu, $5\times10^{10}$ or about $5\times10^{10}$ cfu, $1\times10^{11}$ or about $1\times10^{11}$ cfu or $5\times10^{11}$ or about $5\times10^{11}$ cfu of the bacterium.

5. The combination of claim 1, wherein the composition containing a radiolabeled nucleoside analog contains an amount of the nucleoside analog sufficient to produce a detectable signal.

6. The combination of claim 1, wherein the composition containing the radiolabeled nucleoside analog compound contains about or 1 mg, about or 10 mg, about or 50 mg, about or 100 mg, about or 200 mg, about or 300 mg, about or 400 mg, about or 500 mg, about or 600 mg, about or 700 mg, about or 800 mg, about or 900 mg, about or 1000 mg, about or 1500 mg, about or 2000 mg or about or 2500 mg of the radiolabeled nucleoside analog compound.

7. The combination of claim 1, wherein the radiolabeled nucleoside analog comprises a radioisotope selected from among $^{123}$I, $^{124}$I, $^{125}$I, $^{131}$I, $^{18}$F, $^{19}$F, $^{11}$C, $^{13}$C, $^{14}$C, $^{75}$Br, $^{76}$Br and $^{3}$H.

8. The combination of claim 1, wherein the radiolabeled nucleoside analog compound is selected from among 1-(2'deoxy-2'-fluoro-β-D-arabinofuranosyl)-5-iodouracil (FIAU), 1-(2'deoxy-2'-fluoro-β-D-arabinofuranosyl)-5-ethyluracil (FEAU), 1-(2'-deoxy-2'-fluoro-β-D-arabinofuranosyl)-5-methyluracil (FMAU), 3'-deoxy-3'-fluorothymidine (FLT), 9-[4'-fluoro-3'-(hydroxymethyl)butyl]guanine (FHBG) and 9[(3'-fluoro-1'-hydroxy-2'-propoxy)methyl]guanine (FHPG).

9. The combination of claim 1, wherein the radiolabeled nucleoside analog compound is selected from among [$^{125}$I]-1-(2'deoxy-2'-fluoro-β-D-arabinofuranosyl)-5-iodouracil ([$^{125}$I]-FIAU), [$^{124}$I]-1-(2'deoxy-2'-fluoro-β-D-arabinofuranosyl)-5-iodouracil ([$^{124}$I]-FIAU), [$^{18}$F]-1-(2'deoxy-2'-fluoro-β-D-arabinofuranosyl)-5-iodouracil ([$^{18}$F]-FIAU), [$^{18}$F]-1-(2'deoxy-2'-fluoro-β-D-arabinofuranosyl)-5-ethyluracil ([$^{18}$F]-FEAU), [$^{18}$F]-1-(2'-deoxy-2'-fluoro-β-D-arabinofuranosyl)-5-methyluracil ([$^{8}$F]-FMAU), [$^{18}$F]-3'-deoxy-3'-fluorothymidine ([$^{18}$F]-FLT), [$^{18}$F]-9-[4'-fluoro-3'-(hydroxymethy)butyl]guanine ([$^{18}$F]-FHBG) and [$^{18}$F]-9-[(3'-fluoro-1'-hydroxy-2'-propoxy)methyl]guanine([$^{18}$F]-FHPG).

10. A kit, comprising the combination of claim 1.

* * * * *

UNITED STATES PATENT AND TRADEMARK OFFICE
CERTIFICATE OF CORRECTION

PATENT NO. : 8,343,509 B2
APPLICATION NO. : 13/199567
DATED : January 1, 2013
INVENTOR(S) : Stritzker et al.

It is certified that error appears in the above-identified patent and that said Letters Patent is hereby corrected as shown below:

IN THE CLAIMS:

Column 66, line 64 to line 67 should read
7. The combination of claim 1, wherein the radiolabeled nucleoside analog comprises a radioisotope selected from among $^{123}I$, $^{124}I$, $^{125}I$, $^{131}I$, $^{18}F$, $^{19}F$, $^{11}C$, $^{13}C$, $^{14}C$, $^{75}Br$, $^{76}Br$ and $^{3}H$.

Column 67, line 9 to column 68, line 9 should read
9. The combination of claim 1, wherein the radiolabeled nucleoside analog compound is selected from among [$^{125}I$]-1-(2'deoxy-2'-fluoro-β-D-arabinofuranosyl)-5-iodouracil ([$^{125}I$]-FIAU), [$^{124}I$]-1-(2'deoxy-2'-fluoro-β-D-arabinofuranosyl)-5-iodouracil ([$^{124}I$]-FIAU), [$^{18}F$]-1-(2'deoxy-2'-fluoro-β-D-arabinofuranosyl)-5-iodouracil ([$^{18}F$]-FIAU), [$^{18}F$]-1-(2'deoxy-2'-fluoro-β-D-arabinofuranosyl)-5-ethyluracil ([$^{18}F$]-FEAU), [$^{18}F$]-1-(2'-deoxy-2'-fluoro-β-D-arabinofuranosyl)-5-methyluracil ([$^{18}F$]-FMAU), [$^{18}F$]-3'-deoxy-3'-fluorothymidine ([$^{18}F$]-FLT), [$^{18}F$]-9-[4'-fluoro-3'-(hydroxymethyl)butyl]guanine ([$^{18}F$]-FHBG) and [$^{18}F$]-9-[(3'-fluoro-1'-hydroxy-2'-propoxy)methyl]guanine ([$^{18}F$]-FHPG).

Signed and Sealed this
Ninth Day of April, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,343,509 B2  Page 1 of 1
APPLICATION NO. : 13/199567
DATED : January 1, 2013
INVENTOR(S) : Stritzker et al.

It is certified that error appears in the above-identified patent and that said Letters Patent is hereby corrected as shown below:

IN THE SPECIFICATION:

At column 27, line 9, please replace "pseudomonas A endotoxin" with --Pseudomonas exotoxin--

Signed and Sealed this
Twenty-fourth Day of September, 2013

Teresa Stanek Rea
*Deputy Director of the United States Patent and Trademark Office*